US008865673B2

(12) United States Patent
Detmar et al.

(10) Patent No.: US 8,865,673 B2
(45) Date of Patent: Oct. 21, 2014

(54) MONITORING AND MODULATING HGF/HGFR ACTIVITY

(75) Inventors: Michael Detmar, Boppelsen (CH); Kentaro Kajiya, Yokohama (JP)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 13/606,490

(22) Filed: Sep. 7, 2012

(65) Prior Publication Data

US 2013/0064833 A1    Mar. 14, 2013

Related U.S. Application Data

(63) Continuation of application No. 12/784,272, filed on May 20, 2010, now abandoned, which is a continuation of application No. 11/394,422, filed on Mar. 31, 2006, now abandoned.

(60) Provisional application No. 60/667,463, filed on Mar. 31, 2005.

(51) Int. Cl.
*A61K 48/00* (2006.01)
*C07K 14/475* (2006.01)
*G01N 33/50* (2006.01)
*A61K 38/18* (2006.01)

(52) U.S. Cl.
CPC ........ *A61K 38/1833* (2013.01); *G01N 33/5064* (2013.01); *G01N 2333/4753* (2013.01)
USPC ........................................ 514/44 R; 530/399

(58) Field of Classification Search
None
See application file for complete search history.

(56) References Cited

U.S. PATENT DOCUMENTS

| 5,316,921 | A | 5/1994 | Godowski et al. |
| 5,342,831 | A | 8/1994 | Nakamura et al. |
| 6,468,529 | B1 | 10/2002 | Schwall et al. |
| 2002/0102260 | A1 | 8/2002 | Achen et al. |
| 2005/0026830 | A1 | 2/2005 | Kawaguchi |
| 2005/0261231 | A1 * | 11/2005 | Kubo et al. ...................... 514/44 |

FOREIGN PATENT DOCUMENTS

| EP | 1 661 578 | 5/2006 |
| WO | WO 92/13097 | 8/1992 |
| WO | WO 93/15754 | 8/1993 |
| WO | WO 94/06909 | 3/1994 |
| WO | WO 98/00543 | 1/1998 |
| WO | WO 01/44294 | 6/2001 |
| WO | WO 02/29087 | 4/2002 |
| WO | WO 2004/026906 | 4/2004 |
| WO | WO 2005/023287 | 3/2005 |

OTHER PUBLICATIONS

Morishita et al. Safety Evaluation of Clinical Gene Therapy Using Hepatocyte Growth Factor to Treat Peripheral Arterial Disease, Hypertension vol. 44:203-209 (Aug. 2004).*
Saito et al. Transfection of Human Hepatocyte Growth Factor Gene Ameliorates Secondary Lymphedema via Promotion of Lymphangiogenesis. Circulation vol. 114:1177-1184 (2006).*
Jiang, et al; "Cellular, Molecular, and Tumor Biology 74: Regulators of Increased Angiogenesis, Abstract #3612"; Proc. Amer. Assoc. Cancer Res.; vol. 45 (2004); 2 pp.
Yoon, et al; "VEGF-C Gene Therapy Augments Postnatal Lymphangiogenesis and Ameliorates Secondary Lymphedema"; J. Clon. Invest. vol. 111 (2003); 717-725 pp.
Korean Notice of Preliminary Rejection; Korean Patent Application. No. 10-2007-7024730; Feb. 27, 2013; 6 pp.
The First Office Action; Chinese Patent Application. No. 200680019187.3; May 25, 2010; 4 pp.
The Second Office Action; Chinese Patent Application No. 200680019187.3; Apr. 18, 2012; 3 pp.
Communication Pursuant to Article 94(3) EPC; European Patent Application No. 06 749 190.2; Jun. 13, 2013; 6 pp.
Communication Pursuant to Article 94(3) EPC; European Patent Application No. 06 749 190.2; Nov. 22, 2012; 5 pp.
Notice of Reasons for Rejection; Chinese Patent Application No. 2008-504520; Oct. 11, 2011; 6 pp.
Decision of Final Rejection; Chinese Patent Application No. 2008-504520; Nov. 6, 2012; 4 pp.
Notice of Preliminary Rejection; Korean Patent Application No. 10-2007-7024730; Apr. 27, 2013; 6 pp.
Decision; Taiwan Patent Application No. 093126165; May 18, 2010; 12 pp.
International Preliminary Report on Patentability; International Patent Application No. PCT/US2006/012389; Mar. 31, 2005; 11 pp.
International Search Report and Written Opinion; International Patent Application No. PCT/US2006/012389; Mar. 30, 2006; 15 pp.
Office Action issued in U.S. Appl. No. 12/784,272; mailed on Sep. 17, 2010.
Fish & Richardson; Response to Office Action issued in U.S. Appl. No. 12/784,272; mailed Mar. 17, 2011.
Office Action issued in U.S. Appl. No. 12/784,272; mailed on May 31, 2011.
Fish & Richardson; Response to Office Action issued in U.S. Appl. No. 12/784,272; mailed Nov. 16, 2011.
Final Office Action issued in U.S. Appl. No. 12/784,272; mailed on Mar. 8, 2012.
Notice of Preliminary Rejection; Korean Patent Application No. 2007-7024730; Apr. 27, 2013; 7 pp.
Office Action; Taiwan Patent Application No. 95111167; Nov. 25, 2008; 4 pp.
Andriushin et al., "[Senile Changes in the Intraorganic Lymphatic Bed of Human Facial Skin]," Arkh. Anat. Gistol. Embriol., 71:114-117 (1996) English Abstract Only.

(Continued)

*Primary Examiner* — Elizabeth C Kemmerer
*Assistant Examiner* — Regina M Deberry
(74) *Attorney, Agent, or Firm* — Fish & Richardson P.C.

(57) ABSTRACT

Provided are methods and compositions for the modulation of hepatocyte growth factor activity to regulate lymphatic vessel development and function. Methods and composition for the monitoring and treatment of skin disorders, lymphedema, and metastatic cancers are disclosed. Also described are methods of identifying inhibitors of hepatocyte growth factor dependent lymphangiogenesis.

16 Claims, 10 Drawing Sheets

(56) References Cited

OTHER PUBLICATIONS

Bechara et al., "Morbihan's Disease: Treatment with $CO_2$ Laser Blepharoplasty," J. Dermatol., 31:113-115 (2004).
Bell et al., "The Upstream Regulatory Regions of the Hepatocyte Growth Factor Gene Promoter Are Essential for Its Expression in Transgenic Mice," J. Biol. Chem., 273:6900-08 (1998).
Bing et al., "Serum levels of Hepatocyte Growth Factor and Granulocyte Macrophage-Colony Stimulating Factor in Patients with Psoriasis," Abstract; Zhonghua Pifuke Zazhi, vol. 28, No. 3, 148-150 (2005).
Boehm et al., "Bilateral Upper Limb Lymphoedema Asociated with Psoriatic Arthritis: A Case Report and Review of the Literature," Br. J. Derm., 143:1297-1301 (2000).
Boehncke et al., "Animal models of psoriasis," Clinics in Dermatology 25:596-605 (2007).
Bottaro et al., "Identification of the Hepatocyte Growth Factor Receptor as the c-met Proto-Oncogene Product," Science, 251:802-804 (1991).
Buechner, "Rosacea: An Update," Dermatology, 210:100-108 (2005).
Cao et al., "Hepatocyte growth factor is a lymphangiogenic factor with an indirect mechanism of action," Blood 107:3531-6 (2006).
Chalmers, "Rosacea: recognition and management for the primary care provider," Nurse Pract., 22:18, 23-28, 30 (1997).
Chen and Crosby, "Periorbital edema as an initial presentation of rosacea," J. Am. Acad. Dermatol., 37:346-348 (1997).
Cliff et al., "An in Vivo Study of the Microlymphatics in Psoriasis Using Fluorescence Microlymphography," Br. J. Derm., 140:61-66 (1999).
Dahl, "Pathogenesis of Rosacea," Adv. Dermatol., 17:29-45 (2001).
Definition of "Dermatosis", Webster's Medical Desk Dictionary, p. 173, Merriam-Webster, Inc., Springfield, MA (1986).
Dunsmore et al., "Mechanisms of Hepatocyte Growth Factor Stimulation of Keratinocyte Metalloproteinase Production," The Journal of Biological Chemistry, vol. 271, No. 40, Issue of Oct. 4, 1996 24576-24582.
Fan et al., "Scatter Factor Protects Eipthelial and Carcinoma Cells Against Apoptosis Induced by DNA-damaging Agents," Oncogene, 17:131-141 (1998).
Gambarotta et al., "Structure and Inducible Regulation of the Human MET Promoter," J. Biol. Chem., 269:12852-57 (1994).
Gomaa et al., "Lymphangiogenesis and Angiogenesis in Nonphymatous Rosacea," J. Cutan. Pathol., 34:748-753 (2007) Abstract Only.
Hartmann et al., "A Functional Domain in the Heavy Chain of Scatter Factor/Hepatocyte Growth Factor Binds the c-Met Receptor and Induces Cell Dissociation but Not Mitogenesis," Proc. Natl. Acad. Sci. USA, 89:11574-78 (1992).
Harvey et al., "Rosaceous Lymphedema: A Rate Variant of a Common Disorder," Cutis, 61:321-324 (1998).
Jansen and Plewig, "The treatment of rosaceous lymphoedema," Clin. Exp. Dermatol., 22:57 (1997).
Jansen et al., "[Persistant Erythema and Edema of the Face Associated with Rosacea and Lymph Vessel Dysplasia]," Hautarzt, 49:932-935 (1998) English Abstract Only.
Jiang et al., "The potential lymphangiogenic effects of hepatocyte growth factor/scatter factor in vitro and in vivo," Int. J. Mol. Med. 16:723-8 (2005).
Kajiya et al., "Hepatocyte growth factor promotes lymphatic vessel formation and function," EMBO J. 24:2885-95 (2005).
Kirchhofer et al., "Structural and functional basis of the serine protease-like hepatocyte growth factor β-chain in Met binding and signaling," J. Biol. Chem., 279:39915-24 (2004).
Lokker and Godowski, "Generation and Characterization of a Competitive Antagonist of Human Hepatocyte Growth Factor, HGF/NK1," J. Biol. Chem., 268:17145-50 (1991).
Lokker et al., "Structure-function Analysis of Hepatocyte Growth Factor: Identification of Variants that Lack Mitogenic Activity Yet Retain High Affinity Receptor Binding," EMBO J., 11:2503-10 (1992).

Marzano et al., "Elephantoid oedema of the eyelids," J. Eur. Acad. Dermatol. Venereol., 18:459-462 (2004).
Matsumoto et al., "Deletion of Kringle Domains or the N-Terminal Hairpin Structure in Hepatocyte Growth Factor Results in Marked Decreases in Related Biological Activities," Biochem. Biophys. Res. Comm., 181:691-699 (1991).
Mazzatena et al., "Solid persisent facial oedema (Morbihan's disease) following rosacea, successfully treated with isotretinoin and ketotifen," Br. J. Dermatol., 137:1020-21 (1997).
Mildner et al., "Hepatocyte Growth Factor/Scatter Factor Inhibits UVB-induced Apoptosis of Human Keratinocytes but not of Keratinocyte-Derived Cell Lines via the Phosphatidylinositol 3-Kinase/AKT pathway," The Journal of Biological Chemistry, vol. 277/16: 14146-14152 (2002).
Mildner et al., "UV induced Hepatocyte Growth actor from Dermal Fibroblasts Protects Keratinocytes and Fibroblasts from UV-induced Apoptosis," J. Investigative Dermatology 123, No. 2 (2004), Meeting Info: 34th Annual Meeting of the European Society for Dermatological Research (ESDR). Viena, Austria, Sep. 9-11,20.
Morales-Burgos et al., "Persistent eyelid swelling in a patient with rosacea," P. R. Health Sci. J., 28:80-82 (2009).
Naldini et al., "Hepatocyte Growth Factor (HGF) Stimulates the Tyrosine Kinase Activity of the Receptor Encoded by the Proto-Oncogene c-MET," Oncogene, 6:501-504 (1991).
Park et al., "Sequence of Met Protooncogene cDNA has Features Characteristic of the Tyrosine Kinase Family of Growth-Factor Receptors," Proc. Natl. Acad. Sci. USA, 84:6379-83 (1987).
Pena et al., "Cutaneous Lymphangiectases Associated with Severe Photoaging and Topical Corticosteroid Application," J. Cutan. Pathol., 23:175-181 (1996) Abstract Only.
Scerri and Saiham, "Persistent facial swelling in a patient with rosacea," Arch. Dermatol., 131:1071, 1074 (1995).
Stamos et al., "Crystal structure of the HGF β-chain in complex with the Sema domain of the Met receptor," EMBO J., 23:2325-35 (2004).
Takayama et al., "Scatter Factor/Hepatocyte Growth Factor as a Regulator of Skeletal Muscle and Neural Crest Development," Proc. Natl. Acad. Sci. USA, 93:5866-71 (1996).
Uhara et al., "Solid Facial Edema in a Patient with Rosacea," J. Dermatol., 27:214-216 (2000).
Vlahakis et al., "The lymphangiogenic vascular endothelial growth factors VEGF-C and -D are ligands for the integrin α9β1," J. Biol. Chem. 280:4544-52 (2005).
Wohlrab et al., "Persistent Erythema and Edema of the Midthird and Upper Aspect of the Face (Morbus Morbihan): Evidence of Hidden Immunologic Contact Urticaria and Impaired Lymphatic Drainage," J. Am. Acad. Dermatol., 52:595-602 (2005) Abstract Only.
Zuber, "Rosacea," Primary Care, 27:309-318 (2000).
Restriction Requirement issued in U.S. Appl. No. 11/394,422, mailed on Oct. 19, 2007.
Fish & Richardson, Response to Restriction Requirement issued in U.S. Appl. No. 11/394,422, filed Nov. 19, 2007.
Office Action issued in U.S. Appl. No. 11/394,422, mailed on Feb. 13, 2008.
Fish & Richardson, Response to Office Action issued in U.S. Appl. No. 11/394,422, mailed Aug. 13, 2008.
Final Office Action issued in U.S. Appl. No. 11/394,422, mailed on Nov. 25, 2008.
Fish & Richardson, Response to Final Office Action, issued in U.S. Appl. No. 11/394,422, mailed Feb. 25, 2009.
Office Action issued in U.S. Appl. No. 11/394,422, mailed on Apr. 15, 2009.
Fish & Richardson, Response to Office Action, issued in U.S. Appl. No. 11/394,422, mailed Oct. 15, 2009.
Final Office Action issued in U.S. Appl. No. 11/394,422, mailed on Dec. 21, 2009.
International Search Report and Written Opinion of the International Searching Authority issued in International Application No. PCT/US2006/012389, mailed on Jan. 8, 2006.
Al-Rawi et al., "Molecular and cellular mechanisms of lymphangiogenesis," Eur. J. Surg. Oncol., 31:117-121(2004).
Kubo, "Special Topic II: Molecular Pathogenesis of Angiogenesis and Diseases associated with the Same Basics of Lymphatic Vessel

(56) References Cited

OTHER PUBLICATIONS

Formation and Diseases Caused by the Same," Inflammation and Immunity, 12:608-615 (2004) (with English translation).
Byzova et al., "Adenovirus encoding vascular endothelial growth factor-D induces tissue-specific vascular patterns in vivo"; Blood 99:4434-4442 (2002).
Alitalo et al., "Molecular mechanisms of lymphangiogenesis in health and disease," Cancer Cell, vol. 1:219-227 (2002).
Van De Veert et al., "Factors of importance of a successful delivery system for protein," Expert Opinion Drug Delivery 2:1029-1037 (2005).
Szuba et al., "Therapeutic lymphangiogenesis with human recombinant VEGF-C, The FASEB journal:official publication of the Federation of American Societies for Experimental Biology," Abstract, vol. 16, No. 14:1985-1987 (2002).
Jiang et al., "Is hepatocyte growth factor/scatter factor (HGF/SF) lymphangiogenic?" Abstract, Breast Cancer Research and Treatment, 82: 1:S64-S65 (2003).
Abounader et al., "In vivo targeting of SF/HGF and c-met expression via U1snRNA/ribozymes inhibits glioma growth and angiogenesis and promotes apoptosis," *FASEB J.* 16:108-110, 2002.
Baca-Estrada et al., "Effects of IL-12 on Immune Responses Induced by Transcutaneous Immunization with Antigens Formulated in a Novel Lipid-Based biphasic Delivery System," *Vaccine* 18:1847-1854, 2000 (Abstract only).
Cao et al., "Neutralizing Monoclonal Antibodies to Hepatocyte Grown Factor/Scatter Factor (HG/SF) display Antitumor Activity in Animal Models," *Proc. Nat. Acad. Sci. U.S.A.* 98:7443-7448, 2001.
Chinese First Office Action; Chinese Patent Appl. No. 201210536271.X; mailed Nov. 19, 2013; 5 pp.
Firon et al., "Dominant Negative Met Reduces Tumorigenicity-Metastasis and Increases Tubule Formation in Mammary Cells," *Oncogene* 19:2386-2397, 2000.
Furlong et al., "Comparison of Biologican and Immunochemical Properties Indicates that Scatter Factor and Hepatocyte Growth Factor are Indistinguishable," *J. Cell Sci.* 100:173-177, 1991.
Hirakawa et al., "Vascular Endothelial Growth Factor Promotes Sensitivity to Ultraviolet B-induced Cutaneous Photodamage," *Blood* 105:2392-2399, 2005.
Holzbeierlein et al., "Gene Expression Analysis of Human Prostate Carcinoma during Hormonal Therapy Identifies Androgen-Responsive Genes and Mechanisms of Therapy Resistance," *Am. J Pathol.* 164:217-227, 2004.
Humphrey et al., "Hepatocyte Growth Factor and Its Receptor (c-MET) in Prostatic Carcinoma." *Am. J Pathol.* 147:386-396, 1995.
Japanese Office Action (with English Translation); Japanese Patent Application No. 2012-090431; mailed Jun. 28, 2013; 7 pp.
Jiang et al., "The Potential Lymphagiogenic Effects of Hepatocyte Growth Factor/Scatter Factor in vitro and in vivo," *Int. J Mol. Med.* 16:723-728, 2005.
Karande et al., "Design Principles of Chemical Penetration Enhancers for Transdermal Drug Delivery," *Proc. Natl Acad. Sci. U.S.A.* 102:4688-4693, 2005 (Abstract only).
Korean Notice of Preliminary Rejection (with English Translation); Korean Patent Application No. 10-2013-7019978; mailed Oct. 25, 2013.
Michiel et al., "Targeting the Tumor and Its Microenvironment by a Dual-Function Decoy Met Receptor," *Cancer Cell* 6:61-73, 2004.
Nagy et al., "Vascular Permeability Factor/Vascular Endothelial Growth Factor Induces Lymphangiogenesis as well as Angiogenesis," *J. Exp. Med.* 196:1497-1506, 2002.
Parr et al., "Expression of Hepatocyte Growth Factor/Scatter Factor, its Activator, Inhibitors and the c-Met Receptor in Human Cancer Cells," *Int. J. Oncol.* 19:857-864, 2001 (Abstract only).
Tomioka et al , "Inhibition of Growth, Invasion, and Metastasis of Human Pancreatic Carcinoma Cells by NK4 in an Orthotopic Mouse Model," *Am. Assoc. Cancer Res.* 61:7518-7524, 2001.
Vavrova et al., "Amphiphilic Transdermal Permeation Enhancers: Structure-Activity Relationships," *Curr. Med. Chem.* 12:2273-2291, 2005 (Abstract only).
Wang, et al., "Digital Karyotyping Identifies Thymidylate Synthase Amplification as a Mechanism of Resistance to 5-fluorouracil in Metastatic Colorectal Cancer Patients," *Proc. Natl. Acad. Sci. U.S.A.* 101:3089-3094, 2004.
Korean Patent Application No. 10-2007-7024370; Notice of Result of Pre-trial Reexamination; mailed Mar. 25, 2014, 5 pp.
Japanese Notice of Reasons for Rejection; JP Appln. No. 2013-149577; mailed Jul. 15, 2014; 3 pp.
Korean Notice of Preliminary Rejection; KR Appln. No. 10-2014-7011245; mailed Jul. 29, 2014; 4 pp.
European Communication; EP Appln. No. 13172330.6; mailed Jun. 27, 2014; 9 pp.

* cited by examiner

MONITORING AND MODULATING HGF/HGFR ACTIVITY

CROSS-REFERENCE TO RELATED APPLICATIONS

This application is a continuation of U.S. application Ser. No. 12/784,272, filed on May 20, 2010, which is a continuation of U.S. application Ser. No. 11/394,422, filed on Mar. 31, 2006, which claims priority to U.S. Application Ser. No. 60/667,463, filed on Mar. 31, 2005. The contents of the foregoing applications are hereby incorporated by reference in their entirety.

GOVERNMENT SUPPORT

This invention was made with Government support under Grant No. CA069184 awarded by the National Institutes of Health. The Government has certain rights in this invention.

BACKGROUND

Hepatocyte growth factor (HGF) is a growth factor that can be found in human serum. The HGF receptor (HGFR) has been identified as the product of the c-Met proto-oncogene. See, e.g., Bottaro et al., Science, 251:802-804 (1991); Naldini et al., Oncogene, 6:501-504 (1991); WO 92/13097; and WO 93/15754.

SUMMARY

In one aspect, the disclosure features a method of treating a subject having an unwanted skin condition, e.g., a condition that impairs skin structure. The method includes administering, to the subject, a therapeutically effective amount of an HGF/HGFR modulator. In one aspect, the disclosure features the use of a therapeutically effective amount of an HGF/HGFR modulator (e.g., an agonist or antagonist) in the preparation of a medicament.

In one embodiment the modulator is an HGF/HGFR agonist. An HGF/HGFR agonist is an agent that directly or indirectly increases HGF/HGFR activity in the subject.

The agonist can be used to treat a condition or in the preparation of a medicament for the treatment of a condition in which increased lymphatic vessel formation is desired. Such conditions included lymphedema, e.g., acquired lymphedema. Examples of acquired lymphedema include lymphedema acquired after surgery or radiation therapy or lymphedema caused at least in part by an infection, e.g., by a pathogen, e.g., an infection such as filariasis. Other conditions in which increased lymphatic vessel formation is desired include aged skin or damaged skin, e.g., UVB-damaged skin. Still other conditions include those caused in part by a genetic or environmental factor, e.g., ultraviolet radiation. For example, the condition is epidermolysis, e.g., epidermolysis caused by aging or excessive exposure to ultraviolet light.

Many HGF/HGFR agonists increase HGFR signalling activity. Examples of HGF/HGFR agonists include a protein that includes a hepatocyte growth factor polypeptide (e.g., as modified into its mature heterodimeric form) or a biologically active fragment or analog thereof, a nucleic acid encoding a hepatocyte growth factor or a biologically active fragment or analog thereof. Other proteins and molecules, e.g., antibodies and small molecules, can also be used increase HGFR activity. For example, antibodies that bind, and optionally crosslink (e.g., dimerize) HGFR can be used to HGFR activity.

For example, the unwanted condition is an inflammatory or autoimmune skin disorder (e.g., psoriasis), or rosacea dermatosis. A therapeutically effective amount of an HGF/HGFR agonist can be used in the preparation of a medicament for the treatment of such an inflammatory or autoimmune skin disorder or rosacea dermatosis.

In one embodiment, the modulator is an HGF/HGFR antagonist. An HGF/HGFR antagonist is an agent that directly or indirectly decreases HGF/HGFR activity in a cell or in the subject. Antagonists include nucleic acids and proteins, e.g., antibodies or soluble HGF receptor fragments. For example, the antagonist can be a protein that interacts with HGF and, e.g., reduces HGF binding affinity to cell surface HGFR. For example, the protein can be (i) an antibody that recognizes HGF or HGFR, or (ii) a protein that includes a extracellular region of the HGFR, e.g., a soluble HGF receptor (e.g., fused to an Fc domain). Examples of antagonists include: a nucleic acid molecule that can bind or otherwise inhibit HGF mRNA, e.g., mRNA production, processing, or translation. Still other antagonists include: a dominant negative HGF protein or fragment thereof and an agent which decreases HGF nucleic acid expression (e.g., an artificial transcription factor or nucleic acid encoding an artificial transcription factor).

In some implementations, the modulator decreases the endogenous level of HGF or HGFR.

In one aspect, the disclosure features a method of treating a subject who has or is at risk for a neoplastic disorder, e.g., a metastatic cancer, particularly one that includes cell metastasis within lymph vessels or a cancer that has the potential to metastasize to lymph nodes. The method includes administering, to the subject, a therapeutically effective amount of an HGF/HGFR antagonist that decreases HGF/HGFR activity in the subject. A therapeutically effective amount of an HGF/HGFR antagonist can be used in the preparation of a medicament for the treatment of a subject who has or is at risk for a neoplastic disorder, e.g., a metastatic cancer.

Antagonists include nucleic acids and proteins, e.g., antibodies or soluble HGF receptor fragments. For example, the antagonist can be a protein or other agent that interacts with HGF and, e.g., reduces HGF binding affinity to cell surface HGFR. For example, the protein can be an antibody HGF or a extracellular region of the HGFR, e.g., a soluble HGF receptor. Examples of antagonists include: a nucleic acid molecule that can bind or otherwise inhibit HGF mRNA, e.g., mRNA production, processing, or translation. Still other antagonists include: a dominant negative HGF protein or fragment thereof and an agent which decreases HGF nucleic acid expression (e.g., an artificial transcription factor or nucleic acid encoding an artificial transcription factor).

In another aspect, the disclosure features a method of treating a subject who has or is at risk for a neoplastic disorder, e.g., a metastatic cancer, particularly one that includes cell metastasis within lymph vessels or a cancer that has the potential to metastasize to lymph nodes. The method includes administering, to the subject, a therapeutically effective amount of an $\alpha 9$ integrin antagonist that decreases $\alpha 9$ integrin activity in the subject. For example, the antagonist is a protein or other agent that interacts with $\alpha 9$ integrin or a counterpart integrin beta subunit and, e.g., reduces integrin binding affinity to cells. For example, the protein can be an antibody to $\alpha 9$ integrin or a counterpart integrin beta subunit or a extracellular region of an $\alpha 9$ integrin receptor. A therapeutically effective amount of an $\alpha 9$ integrin antagonist can be used in the preparation of a medicament for the treatment of a subject who has or is at risk for a neoplastic disorder, e.g., a metastatic cancer.

Examples of antagonists include: a nucleic acid molecule that can bind or otherwise inhibit α9 integrin mRNA, e.g., mRNA production, processing, or translation. Still other antagonists include: a dominant negative α9 integrin protein or fragment thereof and an agent which decreases α9 integrin nucleic acid expression (e.g., an artificial transcription factor or nucleic acid encoding an artificial transcription factor).

In still another aspect, the disclosure features a method of evaluating a cell or a subject (e.g., using cells obtained from the subject). The method includes evaluating integrin α9 and stanniocalcin 1 mRNA or protein expression in the cell or in cells from the subject. The method can be used to evaluate HGF activity in the subject. For example, the cell or cells obtained from the subject include endothelial cells, e.g., lymph endothelial cells (LEC). The cell or subject can be treated, e.g., before, during, or after the evaluating, with an agent described herein, e.g., an agonist or antagonist of HGF/HGFR. The method can be used to monitor a subject who has or is at risk for a disorder described herein and who may be treated with an agent described herein.

In another aspect, the disclosure features a method of identifying a compound that modulates lymphatic endothelial cell activity, e.g., proliferation or migration. The method includes: providing a cell or organism in which HGF/HGFR activity can be monitored; contacting the cell or organism with a test compound; and evaluating HGF/HGFR activity in the cell or organism. For example, the cell includes a reporter of HGF/HGFR activity or an organism that comprises such a cell. HGF/HGFR activity can be evaluated by assaying, e.g., protein or mRNA expression or reporter activity. A change in reporter activity or other relevant parameter, for example, indicates a change in HGF/HGFR activity. The method can further include evaluating the effect of the test compound on cell proliferation or cell migration, e.g., lymphatic endothelial cell proliferation or migration.

In one embodiment, the reporter is a gene that comprises a sequence encoding a detectable protein and an operably linked promoter that includes a region of the promoter of the HGF or HGF-R gene, e.g. region from the transcription start site to a position at least 100, 200, 300, 500, 800, 1000, 2000, or 5000 bases upstream, from the initiator MET codon to a position at least 100, 200, 300, 500, 800, 1000, 2000, or 5000 bases upstream, or from the TATA box to a position at least 100, 200, 300, 500, 800, 1000, 2000, or 5000 bases upstream.

The cell or organism is generally mammalian, e.g., human or non-human, e.g., mouse, rat, hamster, guinea pig, monkey and so forth.

In another aspect, the disclosure features a method of identifying a compound that modulates endothelial cell activity, for example, a compound that inhibits hepatocyte growth factor-dependent lymphatic endothelial cell proliferation or migration. The method includes: providing an endothelial cell (e.g., a lymphatic endothelial cell) expressing a hepatocyte growth factor receptor; contacting the endothelial cell with hepatocyte growth factor and a test compound; and evaluating the cell, e.g., for a property, e.g., a property regulated by HGF/HGFR, such as proliferation or migration. For example, the method can include determining whether proliferation or migration of the lymphatic endothelial cell is altered in the presence of the test compound. A decrease in proliferation or migration can indicate that the test compound inhibits hepatocyte growth factor-dependent lymphatic endothelial cell proliferation.

The endothelial cell can be a mammalian cell, e.g., a mouse, rat, rabbit, hamster, or human cell. The cell can be cultured or isolated; for example, the cell is from a cell line or a primary cell. In one embodiment, the cell expresses Prox 1 and the hyaluronan receptor LYVE-1.

The method can include evaluating the test compound in the presence of another HGF/HGFR pathway modulator, e.g., in the presence of a protein that includes soluble HGF, a protein that includes a soluble extracellular domain of HGFR, or antibody to HGF or HGFR.

The method can include evaluating tyrosine phosphorylation of the hepatocyte growth factor receptor, e.g., to determine if the test compound causes a decrease. In one embodiment, the lymphatic endothelial cell expresses a recombinant hepatocyte growth factor receptor or a mutant thereof.

The method can further include administering the test compound to an organism, e.g., a human or non-human mammal. The method can further include formulating a test compound or a modified test compound that retains the biological activity of the test compound as a pharmaceutical composition, e.g., by combining the compound with a pharmaceutically acceptable carrier.

In still another aspect, the disclosure features a method for evaluating a test compound, e.g., a compound that is topically applied to a test organism, e.g., a transgenic organism that includes a reporter of HGF/HGFR pathway activity. The method includes contacting a test compound to the test organism and evaluating HGF/HGFR pathway activity. For example, the evaluating can include evaluating protein or mRNA expression of HGF, HGFR, or a gene or gene product that is regulated by HGFR, e.g., α9 integrin or stanniocalcin 1. The method can also include evaluating the test compound in the presence of another HGF/HGFR pathway modulator, e.g., in the presence of a protein that includes soluble HGF, a protein that includes a soluble extracellular domain of HGFR, or antibody to HGF or HGFR.

In one embodiment, the reporter is a gene that includes a sequence encoding a detectable protein and an operably linked promoter that includes a region of the promoter of the HGF, HGFR, α9 integrin or stanniocalcin 1 gene, e.g. region from the transcription start site to a position at least 100, 200, 300, 500, 800, 1000, 2000, or 5000 bases upstream, from the initiator MET codon to a position at least 100, 200, 300, 500, 800, 1000, 2000, or 5000 bases upstream, or from the TATA box to a position at least 100, 200, 300, 500, 800, 1000, 2000, or 5000 bases upstream. The method can also include evaluating two or more such reporters.

The method can include selecting a test compound (e.g., from a library of test compounds), if it increases or decreases HGF/HGFR pathway activity. A selected test compound can formulated, e.g., a pharmaceutical composition, e.g., suitable for topical administration or other route of administration. The method can further include administering the pharmaceutical composition to a subject, e.g., a subject having or at risk for a disorder described herein.

The details of one or more embodiments of the invention are set forth in the accompanying drawings and the description below. Other features, objects, and advantages of the invention will be apparent from the description and drawings, and from the claims. All cited patents, applications, and references are incorporated herein by reference.

DETAILED DESCRIPTION

Figure 1:
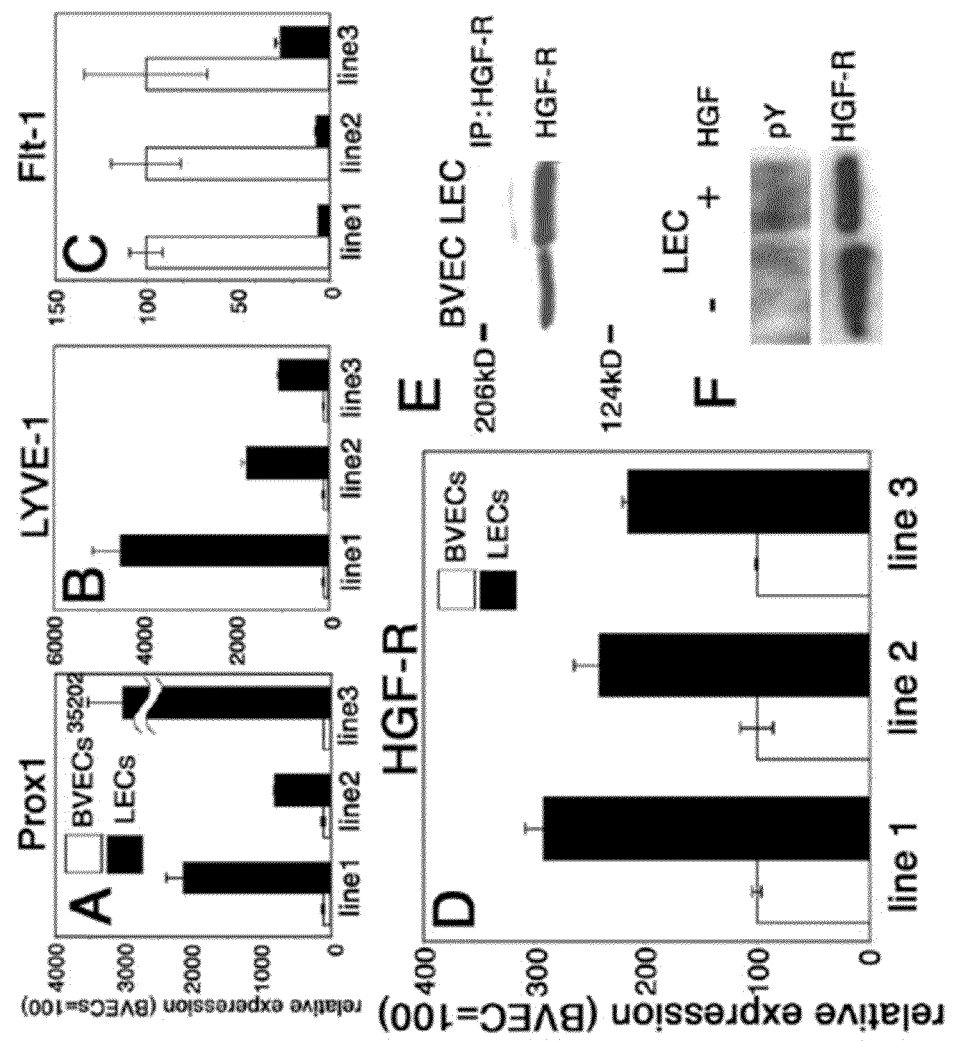
FIG. 1 shows quantitative RT-PCR data for lymphatic cell lineage marker mRNA levels (A-C), quantitative RT-PCR for HGFR mRNA (D), and immunoblot assays for HGFR protein (E and F).

We have found that, among other things, the hepatocyte growth factor receptor (HGFR) is highly expressed in lymphatic endothelial cells (LEC) of the lymphatic system. Treatment of LEC with HGF promotes proliferation, migration, and organization of LECs into vessels. In addition, administration of HGF to mice potently promoted new lymphatic vessel formation. Furthermore, induction of LEC migration was largely mediated via α9 integrin.

Accordingly, it is possible to treat pathologies affected by the lymphatic system by modulating HGF/HGFR activity. A subject can also be diagnosed by evaluating a parameter that assesses HGF/HGFR activity. Agents that modulate HGF/HGFR activity can be identified, e.g., using the assay and screening methods described herein.

I. HGF and HGFR

The mature form of human HGF (hHGF), corresponding to the major form purified from human serum, is a disulfide linked heterodimer derived by proteolytic cleavage of the human pro-hormone between amino acids R494 and V495. This cleavage process generates a molecule composed of an α subunit of 440 amino acids (M.W. 69 kDa) and a β subunit of 234 amino acids (M.W. 34 kDa). The α and the β chains are produced from a single open reading frame coding for a pre-pro precursor protein. In the predicted primary structure of an exemplary mature hHGF, an interchain S—S bridge is formed between Cys 487 of the α chain and Cys 604 in the β chain (see, e.g., Nakamura et al., Nature 342:440-443, (1989)). The N-terminus of the α chain is preceded by 54 amino acids, starting with a methionine group. This segment includes a characteristic hydrophobic leader (signal) sequence of 31 residues and the prosequence. The α chain starts at amino acid (aa) 55, and contains four Kringle domains. The Kringle 1 domain extends from about aa 128 to about aa 206, the Kringle 2 domain is between about aa 211 and about aa 288, the Kringle 3 domain is defined as extending from about aa 303 to about aa 383, and the Kringle 4 domain extends from about aa 391 to about aa 464 of the α chain. An exemplary HGF contains four putative glycosylation sites, which are located at positions 294 and 402 of the α-chain and at positions 566 and 653 of the β-chain.

The HGF receptor (HGFR) has been identified as the product of the c-Met proto-oncogene, Bottaro et al., Science, 251:802-804 (1991); Naldini et al., Oncogene, 6:501-504 (1991); WO 92/13097 published Aug. 6, 1992; WO 93/15754 published Aug. 19, 1993. The receptor (AKA c-Met) typically comprises, in its native form, a 190-kDa heterodimeric (a disulfide-linked 50-kDa α-chain and a 145-kDa β-chain) membrane-spanning tyrosine kinase protein (Park et al., Proc. Natl. Acad. Sci. USA, 84:6379-6383 (1987)).

The binding activity of HGF to its receptor is believed to be conveyed by a functional domain located in the N-terminal portion of the HGF molecule, including the first two Kringle domains (Matsumoto et al., Biochem. Biophys. Res. Commun., 181:691-699 (1991); Hartmann et al. Proc. Natl. Acad. Sci., 89:11574-11578 (1992); Lokker et al., EMBO J., 11:2503-2510 (1992); Lokker and Godowski, J. Biol. Chem., 268:17145-17150 (1991)). Upon HGF binding, the c-Met protein becomes phosphorylated on tyrosine residues of the 145-kDa β-subunit.

With respect to the methods disclosed herein, HGF can be produced as a purified polypeptide, for which the amino acid sequence can be at least 80% identical (i.e., 85%, 87%, 89%, 90%, 92%, 94%, 96%, 98%, 99%, or 100% identical) to any of SEQ ID NOs:1-4 listed below or other naturally occurring variants of HGF. The receptor for HGF (HGFR) can be produced as a purified polypeptide, for which the amino acid sequence can be at least 80% identical (i.e., 85%, 87%, 89%, 90%, 92%, 94%, 96%, 98%, 99%, or 100% identical) to any of SEQ ID NOs:5-8 listed below or other naturally occurring variants of HGFR.

Human HGF (SEQ ID NO: 1)

```
  1 MWVTKLLPAL LLQHVLLHLL LLPIAIPYAE GQRKRRNTIH EFKKSAKTTL

51 IKIDPALKIK TKKVNTADQC ANRCTRNKGL PFTCKAFVFD KARKQCLWFP

101 FNSMSSGVKK EFGHEFDLYE NKDYIRNCII GKGRSYKGTV SITKSGIKCQ

151 PWSSMIPHEH SFLPSSYRGK DLQENYCRNP RGEEGGPWCF TSNPEVRYEV

201 CDIPQCSEVE CMTCNGESYR GLMDHTESGK ICQRWDHQTP HRHKFLPERY

251 PDKGFDDNYC RNPDGQPRPW CYTLDPHTRW EYCAIKTCAD NTMNDTDVPL

301 ETTECIQGQG EGYRGTVNTI WNGIPCQRWD SQYPHEHDMT PENFKCKDLR
```

-continued

```
351 ENYCRNPDGS ESPWCFTTDP NIRVGYCSQI PNCDMSHGQD CYRGNGKNYM

401 GNLSQTRSGL TCSMWDKNME DLHRHIFWEP DASKLNENYC RNPDDDAHGP

451 WCYTGNPLIP WDYCPISRCE GDTTPTIVNL DHPVISCAKT KQLRVVNGIP

501 TRTNIGWMVS LRYRNKHICG GSLIKESWVL TARQCFPSRD LKDYEAWLGI

551 HDVHGRGDEK CKQVLNVSQL VYGPEGSDLV LMKLARPAVL DDFVSTIDLP

601 NYGCTIPEKT SCSVYGWGYT GLINYDGLLR VAHLYIMGNE KCSQHHRGKV

651 TLNESEICAG AEKIGSGPCE GDYGGPLVCE QHKMRMVLGV IVPGRGCAIP

701 NRPGIFVRVA YYAKWIHKII LTYKVPQS
```

Chimpanzee HGF (SEQ ID NO: 2)

```
  1 MWVTKLLPAL LLQHVLLHLL LLPIAIPYAE GQRKRRNTIH EFKKSAKTTL

51 IKIDPALKIK TKKVNTADQC ANRCTRNKGL PFTCKAFVFD KARKQCLWFP

101 FNSMSSGVKK EFGHEFDLYE NKGHETFGRF LPSSYRGKDL QENYCRNPRG

151 EEGGPWCFTS NPEVRYEVCD IPQCSEVECM TCNGESYRGL MDHTESGKIC

201 QRWDHQTPHR HKFLPERYPD KGFDDNYCRN PDGQPRPWCY TLDPHTRWEY

251 CAIKTCADNT MNDTDVPLET TECIQGQGEG YRGTVNTIWN GIPCQRWDSQ

301 YPHEHDMTPE NFKCKDLREN YCRNPDGSES PWCFTTDPNI RVGYCSQIPN

351 CDMSHGQDCY RGNGKNYMGN LSQTRSGLTC SMWDKNMEDL HRHIFWEPDA

401 SKLNENYCRN PDDDAHGPWC YTGNPLIPWD YCPISRCEGD TTPTIVNLDH

451 PVISCAKTKQ LRVVNGIPTR TNVGWMVSLR YRNKHICGGS LIKESWVLTA

501 RQCFPSRDLK DYEAWLGIHD VHGRGDEKCK QVLNVSQLVY GPEGSDLVLM

551 KLARPAVLDD FVSTIDLPNY GCTIPEKTSC SVYGWGYTGL INYDGLLRVA

601 HLYIMGNEKC SQHHRGKVTL NESEICAGAE KIGSGPCEGD YGGPLVCEQH

651 KMRMVLGVIV PGRGCAIPNR PGIFVRVAYY AKWIHKIILT YKVPQS
```

Mouse HGF (SEQ ID NO: 3)

```
  1 MMWGTKLLPV LLLQHVLLHL LLLHVAIPYA EGQKKRRNTL HEFKKSAKTT

51 LTKEDPLLKI KTKKVNSADE CANRCIRNRG FTFTCKAFVF DKSRKRCYWY

101 PFNSMSSGVK KGFGHEFDLY ENKDYIRNCI IGKGGSYKGT VSITKSGIKC

151 QPWNSMIPHE HSFLPSSYRG KDLQENYCRN PRGEEGGPWC FTSNPEVRYE

201 VCDIPQCSEV ECMTCNGESY RGPMDHTESG KTCQRWDQQT PHRHKFLPER

251 YPDKGFDDNY CRNPDGKPRP WCYTLDPDTP WEYCAIKTCA HSAVNETDVP

301 METTECIQGQ GEGYRGTSNT IWNGIPCQRW DSQYPHKHDI TPENFKCKDL

351 RENYCRNPDG AESPWCFTTD PNIRVGYCSQ IPKCDVSSGQ DCYRGNGKNY

401 MGNLSKTRSG LTCSMWDKNM EDLHRHIFWE PDASKLNKNY CRNPDDDAHG

451 PWCYTGNPLI PWDYCPISRC EGDTTPTIVN LDHPVISCAK TKQLRVVNGI

501 PTQTTVGWMV SLKYRNKHIC GGSLIKESWV LTARQCFPAR NKDLKDYEAW

551 LGIHDVHERG EEKRKQILNI SQLVYGPEGS DLVLLKLARP AILDNFVSTI

601 DLPSYGCTIP EKTTCSIYGW GYTGLINADG LLRVAHLYIM GNEKCSQHHQ

651 GKVTLNESEL CAGAEKIGSG PCEGDYGGPL ICEQHKMRMV LGVIVPGRGC

701 AIPNRPGIFV RVAYYAKWIH KVILTYKL
```

Rat HGF (SEQ ID NO: 4)

```
  1 MWVTKLLPAL LLQHVLLHLL LLPIAIPYAE GHKKRRNTIH EFKKSAKTTL
 51 IKIDPALKIK TKKVNTADQC ANRCTRNNGL PFTCKAFVFD KARKQCLWFP
101 FNSMSSGVKK EFGHEFDLYE NKDYIRNCII GKGRSYKGTV SITKSGIKCQ
151 PWSSMIPHEH SFLPSSYRGK DLQENYCRNP RGEEGGPWCF TSNPEVRYEV
201 CDIPQCSEVE CMTCNGESYR GLMDHTESGK ICQRWDHQTP HRHKFLPERY
251 PDKGFDDNYC RNPDGQPRPW CYTLDPHTRW EYCAIKTCAD NTVNDTDVPM
301 ETTECIQGQG EGYRGTANTI WNGIPCQRWD SQYPHKHDMT PENFKCKDLR
351 ENYCRNPDGS ESPWCFTTDP NIRVGYCSQI PNCDMSNGQD CYRGNGKNYM
401 GNLSQTRSGL TCSMWNKNME DLHRHIFWEP DASKLNENYC RNPDDDAHGP
451 WCYTGNPLIP WDYCPISRCE GDTTPTIVNL DHPVISCAKT KQLRVVNGIP
501 TRTNVGWMIS LRYRNKHICG GSLIKESWVL TARQCFPSRD LKDYEAWLGI
551 HDVHGRGEEK RKQVLNVSQL VYGPEGSDLV LMKLARPAVL DDFVNTIDLP
601 NYGCTIPEKT SCSVYGWGYT GLINYDGLLR VAHLYIMGNE KCSQHHRGKV
651 TLNESEICAG AEKIGSGPCE GDYGGPLVCE QHKMRMVLGV IVPGRGCAIP
701 NRPGIFVRVA YYAKWIHKII LTYKVPES
```

Human HGFR (SEQ ID NO: 5)

```
   1 MKAPAVLAPG ILVLLFTLVQ RSNGECKEAL AKSEMNVNMK YQLPNFTAET
  51 PIQNVILHEH HIFLGATNYI YVLNEEDLQK VAEYKTGPVL EHPDCFPCQD
 101 CSSKANLSGG VWKDNINMAL VVDTYYDDQL ISCGSVNRGT CQRHVFPHNH
 151 TADIQSEVHC IFSPQIEEPS QCPDCVVSAL GAKVLSSVKD RFINFFVGNT
 201 INSSYFPDHP LHSISVRRLK ETKDGFMFLT DQSYIDVLPE FRDSYPIKYV
 251 HAFESNNFIY FLTVQRETLD AQTFHTRIIR FCSINSGLHS YMEMPLECIL
 301 TEKRKKRSTK KEVFNILQAA YVSKPGAQLA RQIGASLNDD ILFGVFAQSK
 351 PDSAEPMDRS AMCAFPIKYV NDFFNKIVNK NNVRCLQHFY GPNHEHCFNR
 401 TLLRNSSGCE ARRDEYRTEF TTALQRVDLF MGQFSEVLLT SISTFIKGDL
 451 TIANLGTSEG RFMQVVVSRS GPSTPHVNFL LDSHPVSPEV IVEHTLNQNG
 501 YTLVITGKKI TKIPLNGLGC RHFQSCSQCL SAPPFVQCGW CHDKCVRSEE
 551 CLSGTWTQQI CLPAIYKVFP NSAPLEGGTR LTICGWDFGF RRNNKFDLKK
 601 TRVLLGNESC TLTLSESTMN TLKCTVGPAM NKHFNMSIII SNGHGTTQYS
 651 TFSYVDPVIT SISPKYGPMA GGTLLTLTGN YLNSGNSRHI SIGGKTCTLK
 701 SVSNSILECY TPAQTISTEF AVKLKIDLAN RETSIFSYRE DPIVYEIHPT
 751 KSFISGGSTI TGVGKNLNSV SVPRMVINVH EAGRNFTVAC QHRSNSEIIC
 801 CTTPSLQQLN LQLPLKTKAF FMLDGILSKY FDLIYVHNPV FKPFEKPVMI
 851 SMGNENVLEI KGNDIDPEAV KGEVLKVGNK SCENIHLHSE AVLCTVPNDL
 901 LKLNSELNIE WKQAISSTVL GKVIVQPDQN FTGLIAGVVS ISTALLLLLG
 951 FFLWLKKRKQ IKDLGSELVR YDARVHTPHL DRLVSARSVS PTTEMVSNES
1001 VDYRATFPED QFPNSSQNGS CRQVQYPLTD MSPILTSGDS DISSPLLQNT
1051 VHIDLSALNP ELVQAVQHVV IGPSSLIVHF NEVIGRGHFG CVYHGTLLDN
1101 DGKKIHCAVK SLNRITDIGE VSQFLTEGII MKDFSHPNVL SLLGICLRSE
```

-continued

```
1151 GSPLVVLPYM KHGDLRNFIR NETHNPTVKD LIGFGLQVAK GMKYLASKKF

1201 VHRDLAARNC MLDEKFTVKV ADFGLARDMY DKEYYSVHNK TGAKLPVKWM

1251 ALESLQTQKF TTKSDVWSFG VLLWELMTRG APPYPDVNTF DITVYLLQGR

1301 RLLQPEYCPD PLYEVMLKCW HPKAEMRPSF SELVSRISAI FSTFIGEHYV

1351 HVNATYVNVK CVAPYPSLLS SEDNADDEVD TRPASFWETS

Chimpanzee HGFR
                                                       (SEQ ID NO: 6)
   1 MKAPAVLAPG ILVLLFTLVQ RSNGECKEAL AKSEMNVNMK YQLPNFTAET

51 PIQNVILHEH HIFLGATNYI YVLNEEDLQK VAEYKTGPVL EHPDCFPCQD

101 CSSKANLSGG VWKDNINMAL VVDTYYDDQL ISCGSVNRGT CQRHVFPHNH

151 TADIQSEVHC IFSPQIEEPS QCPDCVVSAL GAKVLSSVKD RFINFFVGNT

201 INSSYFPDHP LHSISVRRLK ETKDGFMFLT DQSYIDVLPE FRDSYPIKYV

251 HAFESNNFIY FLTVQRETLD AQTFHTRIIR FCSINSGLHS YMEMPLECIL

301 TEKRKKRSTK KEVFNILQAA YVSKPGAQLA RQIGASLNDD ILFGVFAQSK

351 PDSAEPMDRS AMCAFPIKYV NDFFNKIVNK NNVRCLQHFY GPNHEHCFNR

401 TLLRNSSSCE ARRDEYRTEF TTALQRVDLF MGQFSEVLLT SISTFIKGDL

451 TIANLGTSEG RFMQVVVSRS GPSTPHVNFL LDSHPVSPEV IVEHTLNQNG

501 YTLVVTGKKI TKIPLNGLGC RHFQSCSQCL SAPPFVQCGW CHDKCVRSEE

551 CLSGTWTQQI CLPAIYKVFP NSAPLEGGTR LTICGWDFGF RRNNKFDLKK

601 TRVLLGNESC TLTLSESTMN TLKCTVGPAM NKHFNMSIII SNGHGTTQYS

651 TFSYVDPVIT SISPKYGPMA GGTLLTLTGN YLNSGNSRHI SIGGKTCTLK

701 SVSNSILECY TPAQTISTEF AVKLKIDLAN RETSIFSYRE DPIVYEIHPT

751 KSFISTWWKE PLNIVSFLFC FASGGSTITG VGKNLNSVSV PRMVINVHEA

801 GRNFTVACQH RSNSEIICCT TPSLQQLNLQ LPLKTKAFFM LDGILSKYFD

851 LIYVHNPVFK PFEKPVMISM GNENVLEIKG NDIDPEAVKG EVLKVGNKSC

901 ENIHLHSEAV LCTVPNDLLK LNSELNIEWK QAISSTVLGK VIVQPDQNFT

951 GLIAGVVSIS IALLLLLGFF LWLKKRKQIK DLGSELVRYD ARVHTPHLDR

1001 LVSARSVSPT TEMVSNESVD YRATFPEDQF PNSSQNGSCR QVQYPLTDMS

1051 PILTSGDSDI SSPLLQNTVH IDLSALNPEL VQAVQHVVIG PSSLIVHFNE

1101 VIGRGHFGCV YHGTLLDNDG KKIHCAVKSL NRITDIGEVS QFLTEGIIMK

1151 DFSHPNVLSL LGICLRSEGS PLVVLPYMKH GDLRNFIRNE THNPTVKDLI

1201 GFGLQVAKGM KYLASKKFVH RDLAARNCML DEKFTVKVAD FGLARDMYDK

1251 EYYSVHNKTG AKLPVKWMAL ESLQTQKFTT KSDVWSFGVL LWELMTRGAP

1301 PYPDVNTFDI TVYLLQGRRL LQPEYCPDPL YEVMLKCWHP KAEMRPSFSE

1351 LVSRISAIFS TFIGEHYVHV NATYVNVKCV APYPSLLSSE DNADDEVDTR

1401 PASFWETS

Mouse HGFR
                                                       (SEQ ID NO: 7)
   1 MKAPTVLAPG ILVLLLSLVQ RSHGECKEAL VKSEMNVNMK YQLPNFTAET

51 PIQNVVLHGH HIYLGATNYI YVLNDKDLQK VSEFKTGPVL EHPDCLPCRD

101 CSSKANSSGG VWKDNINMAL LVDTYYDDQL ISCGSVNRGT CQRHVLPPDN

151 SADIQSEVHC MFSPEEESGQ CPDCVVSALG AKVLLSEKDR FINFFVGNTI

201 NSSYPPGYSL HSISVRRLKE TQDGFKFLTD QSYIDVLPEF LDSYPIKYIH
```

-continued

```
 251 AFESNHFIYF LTVQKETLDA QTFHTRIIRF CSVDSGLHSY MEMPLECILT

301 EKRRKRSTRE EVFNILQAAY VSKPGANLAK QIGASPSDDI LFGVFAQSKP

351 DSAEPVNRSA VCAFPIKYVN DFFNKIVNKN NVRCLQHFYG PNHEHCFNRT

401 LLRNSSGCEA RSDEYRTEFT TALQRVDLFM GRLNQVLLTS ISTFIKGDLT

451 IANLGTSEGR FMQVVLSRTA HLTPHVNFLL DSHPVSPEVI VEHPSNQNGY

501 TLVVTGKKIT KIPLNGLGCG HFQSCSQCLS APYFIQCGWC HNQCVRFDEC

551 PSGTWTQEIC LPAVYKVFPT SAPLEGGTVL TICGWDFGFR KNNKFDLRKT

601 KVLLGNESCT LTLSESTTNT LKCTVGPAMS EHFNVSVIIS NSRETTQYSA

651 FSYVDPVITS ISPRYGPQAG GTLLTLTGKY LNSGNSRHIS IGGKTCTLKS

701 VSDSILECYT PAQTTSDEFP VKLKIDLANR ETSSFSYRED PVVYEIHPTK

751 SFISGGSTIT GIGKTLNSVS LPKLVIDVHE VGVNYTVACQ HRSNSEIICC

801 TTPSLKQLGL QLPLKTKAFF LLDGILSKHF DLTYVHNPVF EPFEKPVMIS

851 MGNENVVEIK GNNIDPEAVK GEVLKVGNQS CESLHWHSGA VLCTVPSDLL

901 KLNSELNIEW KQAVSSTVLG KVIVQPDQNF AGLIIGAVSI SVVVLLLSGL

951 FLWMRKRKHK DLGSELVRYD ARVHTPHLDR LVSARSVSPT TEMVSNESVD

1001 YRATFPEDQF PNSSQNGACR QVQYPLTDLS PILTSGDSDI SSPLLQNTVH

1051 IDLSALNPEL VQAVQHVVIG PSSLIVHFNE VIGRGHFGCV YHGTLLDNDG

1101 KKIHCAVKSL NRITDIEEVS QFLTEGIIMK DFSHPNVLSL LGICLRSEGS

1151 PLVVLPYMKH GDLRNFIRNE THNPTVKDLI GFGLQVAKGM KYLASKKFVH

1201 RDLAARNCML DEKFTVKVAD FGLARDMYDK EYYSVHNKTG AKLPVKWMAL

1251 ESLQTQKFTT KSDVWSFGVL LWELMTRGAP PYPDVNTFDI TIYLLQGRRL

1301 LQPEYCPDAL YEVMLKCWHP KAEMRPSFSE LVSRISSIFS TFIGEHYVHV

1351 NATYVNVKCV APYPSLLPSQ DNIDGEGNT

Rat HGFR
                                                   (SEQ ID NO: 8)
   1 MKAPTALAPG ILLLLLTLAQ RSHGECKEAL VKSEMNVNMK YQLPNFTAET

51 PIQNVVLHGH HIYLGATNYI YVLNDKDLQK VSEFKTGPVV EHPDCFPCQD

101 CSSKANVSGG VWKDNVNMAL LVDTYYDDQL ISCGSVNRGT CQRHVLPPDN

151 AADIQSEVHC MFSPLAEEES GQCPDCVVSA LGAKVLLSEK DRFINFFVGN

201 TINSSYPPDY SLHSISVRRL KETQDGFKFL TDQSYIDVLG EFRDSYPIKY

251 IHAFESNHFI YFLTVQKETL DAQTFHTRII RFCSVDSGLH SYMEMPLECI

301 LTEKRRKRST REEVFNILQA AYVSKPGANL AKQIGASPYD DILYGVFAQS

351 KPDSAEPMNR SAVCAFPIKY VNDFFNKIVN KNNVRCLQHF YGPNHEHCFN

401 RTLLRNSSGC EVRSDEYRTE FTTALQAVDL FMGRLNHVLL TSISTFIKGD

451 LTIANLGTSE GRFMQVVLSR TAHFTPHVNF LLDSHPVSPE VIVEHPSNQN

501 GYTLVVTGKK ITKIPLNGLG CGHFQSCSQC LSAPYFIQCG WCHNRCVHSN

551 ECPSGTWTQE ICLPAVYKVF PTSAPLEGGT MLTICGWDFG FKKNNKFDLR

601 KTKVLLGNES CTLTLSESTT NTLKCTVGPA MSEHFNVSVI VSNSRETTQY

651 SAFSYVDPVI TSISPRYGPH AGGTLLTLTG KYLNSGNSRH ISIGGKTCTL

701 KSVSDSILEC YTPGHTVSAE FPVKLKIDLA DRVTSSFSYG EDPFVSEIHP

751 TKSFISGGST ITGIGKNLNS VSTPKLVIEV HDVGVNYTVA CQHRSSSEII
```

```
-continued
 801  CCTTPSLQQL  DLQLPLKTKA  FFLLDGILSK  HFDLTYVHDP  MFKPFEKPVM

851  ISMGNENVVE  IKGDDIDPEA  VKGEVLKVGN  KSCENLHWHS  EALLCTVPSD

901  LLKLNGGELN  IEWKQAVSST  VLGKVIVQPD  QNFAGLIIGA  VSISVVVLLV

951  SGLFLWLRKR  KHKDLGSELV  RYDARVHTPH  LDRLVSARSV  SPTTEMVSNE

1001  SVDYRATFPE  DQFPNSSQNG  ACRQVQYPLT  DLSPILTSGD  SDISSPLLQN

1051  TVHIDLSALN  PELVQAVQHV  VIGPSSLIVH  FNEVIGRGHF  GCVYHGTLLD

1101  SDGKKIHCAV  KSLNRITDIE  EVSQFLTEGI  IMKDFSHPNV  LSLLGICLRS

1151  EGSPLVVLPY  MKHGDLRNFI  RNETHNPTVK  DLIGFGLQVA  KGMKYLASKK

1201  FVHRDLAARN  CMLDEKFTVK  VADFGLARDM  YDKEYYSVHN  KTGAKLPVKW

1251  MALESLQTQK  FTTKSDVWSF  GVLLWELMTR  GAPPYPDVNT  FDITIYLLQG

1301  RRLLQPEYCP  DALYEVMLKC  WHPKAEMRPS  FSELVSRISS  IFSTFIGEHY

1351  VHVNATYVNV  KCVAPYPSLL  PSQDNIDGEA  NT
```

Exemplary regions of HGFR include:

| Region | 52..487 |
|---|---|
| | /region_name="semaphorin domain" |
| | /note="Sema" |
| | /db_xref="CDD:25341" |
| Region | 519..561 |
| and | /region_name="domain found in Plexins, Semaphorins Integrins" |
| | /note="PSI" |
| | /db_xref="CDD:25325" |
| Region | 563..656 |
| Plexins | /region_name="First repeat of the IPT domain of and Cell Surface Receptors (PCSR)" |
| | /note="IPT_plexin_repeat1" |
| | /db_xref="CDD:27712" |
| Region | 657..740 |
| Plexins | /region_name="Second repeat of the IPT domain of and Cell Surface Receptors (PCSR)" |
| | /note="IPT_plexin_repeat2" |
| | /db_xref="CDD:27711" |
| Region | 742..837 |
| Plexins | /region_name="Third repeat of the IPT domain of and Cell Surface Receptors (PCSR)" |
| | /note="IPT_plexin_repeat3" |
| | /db_xref="CDD:27713" |
| Region | 839..932 |
| Surface | /region_name="IPT domain of Plexins and Cell Receptors (PCSR) and related proteins" |
| | /note="IPT_PCSR" |
| | /db_xref="CDD:27705" |

In some embodiments, HGF, and biologically active fragments thereof are provided as purified polypeptides. Purified polypeptides include polypeptides that are generated in vitro (e.g., by in vitro translation or by use of an automated polypeptide synthesizer) and polypeptides that are initially expressed in a cell (e.g., a prokaryotic cell, a eukaryotic cell, an insect cell, a yeast cell, a mammalian cell, a plant cell) and subsequently purified. Cells that express a purified polypeptide can include cells that encode an endogenous gene, cells transduced with an expression vector encoding a polypeptide, and cells that are experimentally manipulated to induce expression of an endogenous gene that is not typically expressed in that cell type (e.g., gene activation technology). In some embodiments, polypeptides are fusion proteins (e.g., an HGFR-glutathione-S-transferase fusion) that may include a protease cleavage site to allow cleavage and separation of the fusion protein into separate polypeptides. In some embodiments, a polypeptide can include an amino acid sequence that facilitates purification of the polypeptide (e.g., a multiple histidine tag, a FLAG tag, etc). Methods for isolating proteins from cells or polypeptides that are expressed by cells, include affinity purification, size exclusion chromatography, high performance liquid chromatography, and other chromatographic purification methods. The polypeptides can be post-translationally modified, e.g., glycosylated.

Purified HGF (e.g., purified human HGF) can be obtained from a mammalian cell line stably transfected with a cDNA encoding the human HGF polypeptide listed herein as SEQ ID NO:2 and secreting mature HGF as described, e.g., in U.S. Pat. No. 5,686,292 to Schwall, or Naka et al., Journal of Biol. Chem., 267(28):20114-20119, (1992). In some embodiments, HGF can be a single chain variant that lacks mitogenic activity but retains high affinity receptor binding, as described in Lokker et al, EMBO J., 11(7):2503-2510, (1992).

II. HGF and HGFR HGF/HGFR Modulators

A variety of agents can be used as a HGF/HGFR modulator to treat pathologies related to the lymphatic system, e.g., induced lymphedema, lymphangiomas, tumor lymphangiogenesis, or tumor metastasis. The agent may be any type of compound that can be administered to a subject (e.g., antibodies, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like). In one embodiment, the HGF/HGFR modulator is a biologic, e.g., a protein having a molecular weight of between 5-300 kDa.

For example, a HGF/HGFR modulator may inhibit binding of HGF to an HGFR or may prevent HGF-mediated NF-κB activation. A typical HGF/HGFR modulator can bind to HGFR, e.g., a single chain variant of HGF that lacks mitogenic activity but retains high affinity receptor binding (see, e.g., Lokker et al, EMBO J., 11(7):2503-2510, (1992)). A HGF/HGFR modulator that binds to HGF may alter the conformation of HGF, hinder binding of HGF to HGFR, or otherwise decrease the affinity of HGF for a HGFR or prevent the interaction between HGF and a HGFR.

A HGF/HGFR modulator (e.g., an antibody) may bind to HGF or to a HGFR with a $K_d$ of less than $10^{-6}$, $10^{-7}$, $10^{-8}$, $10^{-9}$, or $10^{-10}$ M. In one embodiment, the HGF/HGFR modulator binds to HGF with an affinity at least 5, 10, 20, 50, 100, 200, 500, or 1000 better than its affinity for hepatocyte growth factor-like/macrophage stimulating protein (HGF1/MSP). In one embodiment, the HGF/HGFR modulator binds to HGF or HGFR with an affinity at least 5, 10, 20, 50, 100, 200, 500, or 1000-fold better than its affinity for the macrophage stimulating 1 receptor (RON) (e.g., NP_002438). A preferred HGF/HGFR modulator specifically binds HGF or HGFR, such as a HGF or HGFR specific antibody.

Exemplary HGF protein molecules include human HGF (e.g., NP_001010932, shown as SEQ ID NO:1)), Chimpanzee HGF (e.g., XP_519174, shown as SEQ ID NO:2), mouse HGF (e.g., CAA51054, shown as SEQ ID NO:3), and Rat HGF (e.g., 1602237A, shown as SEQ ID NO:4). Also included are proteins that include an amino acid sequence at least 90, 92, 95, 97, 98, 99% identical and completely identical to the mature processed region of the aforementioned HGF proteins (e.g., an amino acid sequence at least 90, 92, 95, 97, 98, 99% identical or completely identical to amino acids 25-1390 of SEQ ID NO:1 and proteins encoded by a nucleic acid that hybridizes under high stringency conditions to a human, chimp, mouse, or rat gene encoding a naturally occurring HGF protein. Preferably, a HGF protein, in its processed mature form, is capable of providing at least one HGF activity, e.g., binding to HGFR.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

As used herein, the term "hybridizes under high stringency conditions" describes conditions for hybridization and washing. Guidance for performing hybridization reactions can be found in *Current Protocols in Molecular Biology*, John Wiley & Sons, N.Y. (1989), 6.3.1-6.3.6, which is incorporated by reference. Aqueous and nonaqueous methods are described in that reference and either can be used. High stringency hybridization conditions include hybridization in 6×SSC at about 45° C., followed by one or more washes in 0.2×SSC, 0.1% SDS at 65° C., or substantially similar conditions.

Exemplary HGF/HGFR modulators include antibodies that bind to HGF or HGFR and soluble forms of the HGFR that compete with cell surface HGFR for binding to HGF. An example of a soluble form of the HGFR is an Fc fusion protein that includes at least a portion of the extracellular domain of HGFR (e.g., a soluble HGF-binding fragment of HGFR), referred to as HGFR-Fc (see e.g., Mark et al., Journal of Biol. Chem., 267(36):26166-26171, (1992)). Other soluble forms of HGFR, e.g., forms that do not include an Fc domain, can also be used. Antibody HGF/HGFR modulators are further discussed below. Other types of HGF/HGFR modulators, e.g., small molecules, nucleic acid or nucleic acid-based aptamers, and peptides, can be isolated by screening, e.g., as described in Jhaveri et al. *Nat. Biotechnol.* 18:1293 and U.S. Pat. No. 5,223,409. Exemplary assays for determining if an agent binds to HGF or HGFR and for determining if an agent modulates a HGF/HGFR interaction are described, e.g., in U.S. Pat. No. 6,468,529 to Schwall et al.

An exemplary soluble form of the HGFR protein includes a region of the HGFR protein that binds to HGF, e.g., an extracellular domain, e.g., domain of in the extracellular region. This region can be physically associated, e.g., fused to another amino acid sequence, e.g., an Fc domain, at its N- or C-terminus. The region from HGFR can be spaced by a linker from the heterologous amino acid sequence. Michieli et al. (2005), Cancer Cell, 6:61-73, describes an exemplary HGFR fusion protein.

A. Antibodies

Exemplary HGF/HGFR modulators include antibodies that bind to HGF and/or HGFR. In one embodiment, the antibody inhibits the interaction between HGF and a HGFR, e.g., by physically blocking the interaction, decreasing the affinity of HGF and/or HGFR for its counterpart, disrupting or destabilizing HGF complexes, sequestering HGF or a HGFR, or targeting HGF or HGFR for degradation. In one embodiment, the antibody can bind to HGF or HGFR at an epitope that includes one or more amino acid residues that participate in the HGF/HGFR binding interface. Such amino acid residues can be identified, e.g., by alanine scanning. In another embodiment, the antibody can bind to residues that do not participate in the HGF/HGFR binding. For example, the antibody can alter a conformation of HGF or HGFR and thereby reduce binding affinity, or the antibody may sterically hinder HGF/HGFR binding. The antibody may bind to the α subunit or the β subunit of HGF.

In addition to antibodies that bind to HGF and/or HGFR, other antibodies can be used. In one embodiment, the antibody can prevent activation of a HGF/HGFR mediated event or activity. For example, it is possible to use an antibody to α9 integrin, which is upregulated by HGF. For example, certain antibodies to α9 can inhibit HGF induced migration of cells.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')$_2$ fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FRs and CDRs has been precisely defined (see, e.g., Kabat, E. A., et al. (1991) *Sequences of Proteins of Immunological Interest, Fifth Edition*, US Department of Health and Human Services, NIH Publication No. 91-3242; and Chothia, C. et al. (1987) *J. Mol. Biol.* 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules. Immunoglobulin domains typically contain two β-sheets formed of about seven β-strands, and a conserved disulfide bond (see, e.g., A. F. Williams and A. N. Barclay (1988) *Ann. Rev Immunol.* 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with HGF or HGFR.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

Antibodies that bind to HGF or a HGFR can be generated by a variety of means, including immunization, e.g., using an animal, or in vitro methods such as phage display. All or part of HGF or HGFR can be used as an immunogen or as a target for selection. For example, HGF or a fragment thereof or HGFR or a fragment thereof, can be used as an immunogen. In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Accordingly, by using hybridoma technology, at least partly human, antigen-specific monoclonal antibodies with the desired specificity can be produced and selected. See, e.g., XENOMOUSE™, Green et al. (1994) Nat. Gen. 7:13-21; US 2003-0070185; U.S. Pat. No. 5,789,650; and WO 96/34096.

Non-human antibodies to HGF and HGFR can also be produced, e.g., in a rodent. The non-human antibody can be humanized, e.g., as described in EP 239 400; U.S. Pat. Nos. 6,602,503; 5,693,761; and 6,407,213, deimmunized, or otherwise modified to make it effectively human.

EP 239 400 (Winter et al.) describes altering antibodies by substitution (within a given variable region) of their complementarity determining regions (CDRs) for one species with those from another. Typically, CDRs of a non-human (e.g., murine) antibody are substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody. Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693, 762; 5,693,761; 5,585,089; and 5,530,101; Tempest et al. (1991) *Biotechnology* 9:266-271 and U.S. Pat. No. 6,407, 213.

Fully human monoclonal antibodies that bind to HGF and HGFR can be produced, e.g., using in vitro-primed human splenocytes, as described by Boerner et al. (1991) *J. Immunol.* 147:86-95. They may be prepared by repertoire cloning as described by Persson et al. (1991) *Proc. Nat. Acad. Sci. USA* 88:2432-2436 or by Huang and Stollar (1991) *J. Immunol. Methods* 141:227-236; also U.S. Pat. No. 5,798,230. Large nonimmunized human phage display libraries may also be used to isolate high affinity antibodies that can be developed as human therapeutics using standard phage technology (see, e.g., Hoogenboom et al. (1998) *Immunotechnology* 4:1-20; Hoogenboom et al. (2000) *Immunol Today* 2:371-378; and US 2003-0232333).

Antibodies and other proteins described herein can be produced in prokaryotic and eukaryotic cells. In one embodiment, the antibodies (e.g., scFv's) are expressed in a yeast cell such as Pichia (see, e.g., Powers et al. (2001) *J. Immunol. Methods* 251:123-35), *Hanseula*, or *Saccharomyces*.

Antibodies, particularly full length antibodies, e.g., IgGs, can be produced in mammalian cells. Exemplary mammalian host cells for recombinant expression include Chinese Hamster Ovary (CHO cells) (including dihydrofolate reductase-negative CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell can be a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr⁻ host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr– CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies (and Fc fusions) may also include modifications, e.g., modifications that alter Fc function, e.g., to decrease or remove interaction with an Fc receptor or with C1q, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some proteins that include an Fc domain, the antibody/protein production system may be designed to synthesize antibodies or other proteins in which the Fc region is glycosylated. For example, the Fc domain of IgG molecules is glycosylated at asparagine 297 in the CH2 domain. The Fc domain can also include other eukaryotic post-translational modifications. In other cases, the protein is produced in a form that is not glycosylated.

Antibodies and other proteins can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the protein of interest, e.g., an antibody or Fc fusion protein. The protein can be purified from the milk, or for some applications, used directly.

Methods described in the context of antibodies can be adapted to other proteins, e.g., Fc fusions and soluble receptor fragments.

B. Variants of HGF

In some embodiments, HGF proteins can be HGF variants that are resistant to proteolytic cleavage by enzymes that are capable of in vivo conversion of HGF into its two-chain form. The variants are preferably stabilized in single-chain form by site directed mutagenesis within a region recognized by an enzyme capable of converting HGF into its two-chain form. These HGF variants retain substantially full receptor binding affinity of the corresponding wild-type HGF, but do not activate the HGFR. In one embodiment, HGF variants can have enhanced receptor binding affinity relative to the corresponding wild-type HGF but be unable to activate the HGFR. Such compounds are competitive antagonists of the corresponding wild-type HGF and, when present in sufficient concentration, are capable of inhibiting the binding of wild-type HGF to HGFR. See, e.g., Lokker et al, EMBO J., 11(7):2503-2510, (1992) and U.S. Pat. No. 5,316,921 to Godowski et al. Accordingly they can be used as HGF/HGFR antagonists.

C. Peptides

In some embodiments, the HGF/HGFR modulator can be a peptide of 32 amino acids or less that independently binds to but does not activate a target molecule (e.g., HGFR). Some such peptides can include one or more disulfide bonds. Other peptides, so-called "linear peptides," are devoid of cysteines. In one embodiment, the peptides are artificial, i.e., not present in Nature or not present in a protein encoded by one or more genomes of interest, e.g., the human genome. Synthetic peptides may have little or no structure in solution (e.g., unstructured), heterogeneous structures (e.g., alternative conformations or "loosely structured), or a singular native structure (e.g., cooperatively folded). Some synthetic peptides adopt a particular structure when bound to a target molecule. Some exemplary synthetic peptides are so-called "cyclic peptides" that have at least a disulfide bond and, for example, a loop of about 4 to 12 non-cysteine residues. Exemplary peptides are less than 28, 24, 20, or 18 amino acids in length.

Peptide sequences that independently bind HGFR can be identified by any of a variety of methods. For example, they can be selected from a display library or an array of peptides. After identification, such peptides can be produced synthetically or by recombinant means. The sequences can be incorporated (e.g., inserted, appended, or attached) into longer sequences.

The techniques discussed in Kay et al., *Phage Display of Peptides and Proteins: A Laboratory Manual* (Academic Press, Inc., San Diego 1996) and U.S. Pat. No. 5,223,409 are useful for preparing a library of potential binders corresponding to the selected parental template. Peptide display libraries can be prepared according to such techniques, and screened for peptides that bind to and inhibit HGFR.

In addition, phage libraries or selected populations from phage libraries can be counter-selected, e.g., by counter-selection with an HGFR binding domain that lacks a SEMA (semaphorin) domain or a PSI (plexin/semaphorin/integrin) domain, both of which contribute to HGF binding. Such procedures can be used to discard peptides that do not contact the HGF binding site.

Peptides can also be synthesized using alternative backbones, e.g., a peptoid backbone, e.g., to produce a compound which has increased protease resistance. In particular this method can be used to make a compound that binds to and inhibits activation of HGFR and is not cleaved, e.g., by serum proteases.

A polypeptide that inhibits HGFR activation can be associated with (e.g., conjugated to) a polymer, e.g., a substantially non-antigenic polymers, such as polyalkylene oxides or polyethylene oxides. Suitable polymers will vary substantially by weight. Polymers having molecular number average weights ranging from about 200 to about 35,000 (or about 1,000 to about 15,000, and 2,000 to about 12,500) can be used. A plurality of polymer moieties can be attached to one polypeptide, e.g., at least two, three, or four such moieties, e.g., having an average molecular weight of about 2,000 to 7,000 Daltons.

For example, the polypeptide can be conjugated to a water soluble polymer, e.g., hydrophilic polyvinyl polymers, e.g. polyvinylalcohol and polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Other compounds can also be attached to the same polymer, e.g., a cytotoxin, a label, or another targeting agent or an unrelated agent. Mono-activated, alkoxy-terminated polyalkylene oxides (PAO's), e.g., monomethoxy-terminated polyethylene glycols (mPEG's); $C_{1-4}$ alkyl-terminated polymers; and bis-activated polyethylene oxides (glycols) can be used for crosslinking See, e.g., U.S. Pat. No. 5,951,974.

D. Nucleic Acid Antagonists

In certain implementations, nucleic acid antagonists are used to decrease expression of an endogenous gene encoding HGF, a HGFR, integrin α9, or stanniocalcin 1. In one embodiment, the nucleic acid antagonist is an siRNA that targets mRNA encoding HGF or a HGFR. Other types of antagonistic nucleic acids can also be used, e.g., a dsRNA, a ribozyme, a triple-helix former, or an antisense nucleic acid. In some embodiments, nucleic acid antagonists can be directed to downstream effector targets of HGFR activation (e.g., human α9 integrin, an exemplary sequence of which is listed under Genbank No. NM_002207).

siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) Proc. Natl. Acad. Sci. USA 97:6499-6503; Billy et al. (2001) Proc. Natl. Sci. USA 98:14428-14433; Elbashir et al. (2001) Nature. 411:494-8; Yang et al. (2002) Proc. Natl. Acad. Sci. USA 99:9942-9947; Siolas et al. (2005), Nat. Biotechnol. 23(2):227-31; 20040086884; U.S. 20030166282; 20030143204; 20040038278; and 20030224432.

Anti-sense agents can include, for example, from about 8 to about 80 nucleobases (i.e., from about 8 to about 80 nucleotides), e.g., about 8 to about 50 nucleobases, or about 12 to about 30 nucleobases. Anti-sense compounds include ribozymes, external guide sequence (EGS) oligonucleotides (oligozymes), and other short catalytic RNAs or catalytic oligonucleotides which hybridize to the target nucleic acid and modulate its expression. Anti-sense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA (e.g., an mRNA encoding HGF or HGFR) can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding HGF or HGFR. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$—$(C_1$-$C_{12})$ alkylaminocytosines and $N^4,N^4$—$(C_1$-$C_{12})$ dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—$(C_1$-$C_{12})$ alkylaminopurines and $N^6,N^6$—$(C_1$-$C_{12})$ dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine Derivatives of any of the aforementioned modified nucleobases are also appropriate. Substituents of any of the preceding compounds may include $C_1$-$C_{30}$ alkyl, $C_2$-$C_{30}$ alkenyl, $C_2$-$C_{30}$ alkynyl, aryl, aralkyl, heteroaryl, halo, amino, amido, nitro, thio, sulfonyl, carboxyl, alkoxy, alkylcarbonyl, alkoxycarbonyl, and the like.

Descriptions of other types of nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

E. Artificial Transcription Factors

Artificial transcription factors can also be used to regulate expression of HGF, a HGFR, integrin α9, or stanniocalcin 1. The artificial transcription factor can be designed or selected from a library, e.g., for ability to bind to a sequence in an endogenous gene encoding HGF or HGFR, e.g., in a regulatory region, e.g., the promoter. For example, the artificial transcription factor can be prepared by selection in vitro (e.g., using phage display, U.S. Pat. No. 6,534,261) or in vivo, or by design based on a recognition code (see, e.g., WO 00/42219 and U.S. Pat. No. 6,511,808). See, e.g., Rebar et al. (1996) *Methods Enzymol* 267:129; Greisman and Pabo (1997) *Science* 275:657; Isalan et al. (2001) *Nat. Biotechnol* 19:656; and Wu et al. (1995) *Proc. Natl. Acad. Sci. USA* 92:344 for, among other things, methods for creating libraries of varied zinc finger domains.

Optionally, an artificial transcription factor can be fused to a transcriptional regulatory domain, e.g., an activation domain to activate transcription or a repression domain to repress transcription. In particular, repression domains can be used to decrease expression of endogenous genes encoding HGF or HGFR. The artificial transcription factor can itself be encoded by a heterologous nucleic acid that is delivered to a cell or the protein itself can be delivered to a cell (see, e.g., U.S. Pat. No. 6,534,261). The heterologous nucleic acid that includes a sequence encoding the artificial transcription factor can be operably linked to an inducible promoter, e.g., to enable fine control of the level of the artificial transcription factor in the cell, e.g., an endothelial cell.

F. Pharmaceutical Compositions

A HGF/HGFR modulator (e.g., an antibody or soluble HGFR protein, e.g., a HGFR extracellular region fused to a Fc) can be formulated as a pharmaceutical composition, e.g., for administration to a subject to a pathology related to the lymphatic system (e.g., a disorder described herein, such as lymphedema, lymphatic filariasis, lymphangiomas, tumor lymphangiogenesis, or tumor metastasis). Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (see, e.g., Berge, S. M., et al. (1977) *J. Pharm. Sci.* 66:1-19).

The HGF/HGFR modulator can be formulated according to standard methods. Pharmaceutical formulation is a well-established art, and is further described, e.g., in Gennaro (ed.), Remington: The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

In one embodiment, the HGF/HGFR modulator (e.g., an antibody or HGFR-Fc) can be formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

The pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form can depend on the intended mode of administration and therapeutic application. Typically compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the HGF/HGFR modulator may be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., *Sustained and Controlled Release Drug Delivery Systems*, J. R. Robinson, ed., Marcel Dekker, Inc., New York, 1978.

A HGF/HGFR modulator (e.g., an antibody or soluble HGFR protein) can be modified, e.g., with a moiety that improves its stabilization and/or retention in circulation, e.g., in blood, serum, or other tissues, e.g., by at least 1.5, 2, 5, 10, or 50 fold.

For example, the HGF/HGFR modulator (e.g., an antibody or soluble HGFR protein) can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used.

For example, a HGF/HGFR modulator can be conjugated to a water soluble polymer, e.g., a hydrophilic polyvinyl polymer, e.g., polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; and branched or unbranched polysaccharides.

When the HGF/HGFR modulator (e.g., an antibody or soluble HGFR protein) is used in combination with a second agent, the two agents can be formulated separately or together. For example, the respective pharmaceutical compositions can be mixed, e.g., just prior to administration, and administered together or can be administered separately, e.g., at the same or different times.

The lymphatic vascular system plays a pivotal role in tissue fluid homeostasis, which affects and is affected by a number of pathologies including, e.g., cancer cell metastasis; acquired lymphedema, e.g., induced by surgery, radiation therapy, or infection; skin conditions, e.g., epidermolysis caused by aging or excessive exposure to ultra-violet light. In addition, tumor metastasis occurs primarily through the lymphatic system, and the extent of lymph node involvement is a key prognostic factor for severity of disease. Lymphangiogenesis and the quantity of intratumoral lymphatic vessels in primary tumors have been correlated with tumor metastasis in animal experiments, for example, in breast cancer. (Skobe et al., Nature Medicine 7(2):192-198 (2001)). Intratumoral lymphatic vasculature can play an important role in the metastasis of many tumor types such as breast, colon, lung, thyroid, gastric, squamous cell cancers, mesotheliomas, osteosarcomas, and neuroblastomas.

G. Administration

The HGF/HGFR modulator (e.g., an antibody or soluble HGFR protein) or other agent can be administered to a subject, e.g., a human subject, by a variety of methods. For many applications, the route of administration is one of: intravenous injection or infusion (IV), subcutaneous injection (SC), intraperitoneally (IP), or intramuscular injection. The HGF/HGFR modulator can be administered as a fixed dose, or a dose adjusted for the subject's weight (e.g., a mg/kg dose).

The dose can also be chosen to reduce or avoid production of antibodies against the HGF/HGFR modulator.

The route and/or mode of administration of the can also be tailored for the individual case, e.g., by monitoring the subject, e.g., using tomographic imaging, lymphangiography, and standard parameters associated with the particular disease, e.g., criteria for assessing lymphatic and lymphatic system-related disorders.

Dosage regimens are adjusted to provide the desired response, e.g., a therapeutic response or a combinatorial therapeutic effect. Generally, any combination of doses (either separate or co-formulated) of the HGF/HGFR modulator (e.g., an antibody) (and optionally a second agent) can be used in order to provide a subject with the agent in bioavailable quantities. For example, doses in the range of 1 mg/kg-100 mg/kg, 0.5-20 mg/kg, or 1-10 mg/kg can be administered.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with the other agent.

The HGF/HGFR modulator may be administered at least once between about 10 minutes to about 48 hours, more preferably between about 10 minutes and 24 hours, more preferably within 3 hours, after the onset of symptoms or manifestation of a lymphatic or lymphatic system-related disorder. For example, the agent may be administered to a patient suffering or at risk for lymphedema. Single or multiple dosages may be given. Alternatively, or in addition, the HGF/HGFR modulator agent may be administered via continuous infusion. The treatment can continue for days, weeks, months or even years so as to adequately modulate lymphangiogenesis in lymphatic or lymphatic system related disorders.

The HGF/HGFR modulator can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

If a subject is at risk for developing a disorder described herein (e.g., filariasis) or another lymphatic system-related disorder, the HGF/HGFR modulator can be administered before the onset of the condition as a preventative measure. The duration of such preventative treatment can be a single dosage of the HGF/HGFR modulator or the treatment may continue (e.g., multiple dosages), for example, a subject at risk for a disorder described herein may be treated with the HGF/HGFR modulator for days, weeks, months, or even years so as to prevent the injury from occurring.

A pharmaceutical composition may include a "therapeutically effective amount" of an agent described herein. Such effective amounts can be determined based on the effect of the administered agent, or the combinatorial effect of agents if more than one agent is used. A therapeutically effective amount of an agent may also vary according to factors such as the disease state, age, sex, and weight of the individual, and the ability of the compound to elicit a desired response in the individual, e.g., amelioration of at least one disorder parameter or amelioration of at least one symptom of the disorder. A therapeutically effective amount is also one in which any toxic or detrimental effects of the composition is outweighed by the therapeutically beneficial effects.

An antagonist of HGF/HGFR can be used to treat cancer. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, prostate, ovary as well as adenocarcinomas which include malignancies such as most colon cancers, rectal cancer, renal-cell carcinoma, liver cancer, non-small cell carcinoma of the lung, cancer of the small intestine and so forth. Metastatic lesions of the aforementioned cancers, and particularly metastatic forms of these cancers, can also be treated or prevented using the methods and compositions described herein.

The method can be used to treat malignancies of the various organ systems, such as those affecting lung, breast, lymphoid, gastrointestinal (e.g., colon), and genitourinary tract, prostate, ovary, pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. Exemplary solid tumors that can be treated include: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

The term "carcinoma" is recognized by those skilled in the art and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is recognized by those skilled in the art and refers to malignant tumors of mesenchymal derivation.

H. Devices and Kits

Pharmaceutical compositions that include the HGF/HGFR modulator (e.g., an antibody or soluble HGFR) can be administered with a medical device. The device can designed with features such as portability, room temperature storage, and ease of use so that it can be used in emergency situations, e.g., by an untrained subject or by emergency personnel in the field, removed to medical facilities and other medical equipment. The device can include, e.g., one or more housings for storing pharmaceutical preparations that include HGF/HGFR modulator, and can be configured to deliver one or more unit doses of the HGF/HGFR modulator.

For example, the pharmaceutical composition can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other devices, implants, delivery systems, and modules are also known.

A HGF/HGFR modulator (e.g., an antibody or soluble HGFR protein) can be provided in a kit. In one embodiment, the kit includes (a) a container that contains a composition that includes a HGF/HGFR modulator, and optionally (b) informational material. The informational material can be descriptive, instructional, marketing or other material that relates to the methods described herein and/or the use of the agents for therapeutic benefit. In one embodiment, the kit also includes a second agent for treating lymphatic and lymphatic system-related disorders. For example, the kit includes a first container that contains a composition that includes the HGF/HGFR modulator, and a second container that includes the second agent.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the HGF/HGFR modulator (e.g., an antibody or soluble HGFR protein), e.g., in a suitable dose, dosage form, or mode of administration (e.g., a dose, dosage form, or mode of administration described herein), to treat a subject who has had or who is at risk for a lymphatic or lymphatic system-related disorder. The information can be provided in a variety of formats, include printed text, computer readable material, video recording, or audio recording, or as information that provides a link or address to substantive material.

In addition to the HGF/HGFR modulator, the composition in the kit can include other ingredients, such as a solvent or buffer, a stabilizer, or a preservative. The HGF/HGFR modulator can be provided in any form, e.g., liquid, dried or lyophilized form, preferably substantially pure and/or sterile. When the agents are provided in a liquid solution, the liquid solution preferably is an aqueous solution. When the agents are provided in a dried form, reconstitution generally is achieved by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage, e.g., a unit that includes both the HGF/HGFR modulator and the second agent, e.g., in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with one or both of the agents or can be empty, but suitable for loading.

III. Methods of Screening for Modulators of HGF/HGFR Pathway Activity

Screening of putative modulators of expression of HGF/HGFR pathway (e.g., HGF, HGFR, integrin α9 and stanniocalcin 1) can be carried out by determining the effect of the modulators on HGF or HGFR promoter activity in vitro or in vivo. For example, a nucleic acid that includes a HGFR promoter (e.g., of the human, monkey or mouse HGFR gene) or regulatory region thereof, e.g., Gambarotta et al. (1994), J. Biol. Chem., 269(17):12852-12857 or e.g., a HGF promoter (e.g., of the human, monkey or mouse HGF gene) or regulatory region thereof, e.g., Bell et al. (1998), J. Biol. Chem., 273(12):6900-6908 can be operably linked to a nucleic acid that encodes a reporter polypeptide, e.g., one of the reporter polypeptides described below (e.g., enhanced green fluorescent protein). Other promoters that can be used include those of other genes modulated by HGF/HGFR pathway activity, e.g., integrin α9 and stanniocalcin 1. The nucleic acid including the target promoter operably linked to the reporter nucleic acid can be introduced into cells in culture and/or be used to generate a transgenic animal, allowing evaluation of promoter activity in vivo. In some embodiments, a transgenic animal can also be evaluated for other phenotypes (e.g., induction or repression of gene expression in skin) affected by administration of an HGF/HGFR modulator.

A. Evaluating Effects of Putative HGF/HGFR Modulators on Skin

Methods disclosed herein allow evaluating a compound for its effect on the expression of HGF or HGFR or other target gene in an experimental subject. In some embodiments, the effect of a compound on skin (e.g., a therapeutic compound for a skin condition) can be evaluated in the same experimental subject in which expression is determined. The effect on skin is usually determined as an effect on the expression of a gene under the control of a skin-metabolism-related promoter. Such promoters include those which control the expression and/or synthesis of: a product which is a component of the skin, e.g., the dermis or epidermis; a product which affects hydration or nutrition of the skin; a product which promotes the synthesis, or degradation, of components of the skin; a product which affects the vasculature of the skin; a product which affects hair follicle metabolism; a product which affects skin glandular structures; a product which affects subcutaneous musculature; a product which affects adipose tissue; or a product which affects cutaneous nerves.

Methods of the invention are useful for evaluating a compound for an effect on a parameter related to the appearance or health of the skin, for example, the elasticity of the skin, the propensity of the skin to wrinkle, the ability of the skin to retain fluids, e.g., water or an oil, the ability of the skin to resist or repair damage, e.g., light or UV induced damage, the metabolism of hair follicles including growth cycling or pigment deposition, or subcutaneous muscle tone and function. Generally, effects on these parameters will be evaluated indirectly, e.g., by the effect on the expression of a reporter gene under the control of a promoter which is normally coupled to a gene which encodes a product which affects any of the these parameters.

Transgenic Animals

Transgenic animals which can be used in the methods of the invention include non-human mammals, such as pigs, e.g., mini-pigs; or rodents, e.g., mice, rats, or guinea pigs, e.g., hairless mice (described in, for example, Begona M. et al. (1994) Proc. Natl. Acad. Sci. 91:7717-7721), nude mice, senescence accelerated mice (described in, for example, Takeda et al. (1991) L. Am. Geriatr. Soc. 39:911-19), or transgenic mutant mice which exhibit a phenotype of accelerated aging. One or more, and preferably essentially all, of the cells of the animal include a transgene. The transgenic animals can be homozygous or heterozygous for the transgene. Mice are a preferred subject animal.

Many methods of making transgenic animals, e.g., mice, are known in the art. One exemplary approach is described below.

Procedures for embryo manipulation and microinjection are described in, for example, Manipulating the Mouse Embryo (Cold Spring Harbor Laboratory Press, Cold Spring Harbor, N.Y., 1986, the contents of which are incorporated herein by reference). Mouse zygotes can be collected from six week old females that have been super ovulated with pregnant mares serum (PMS) followed 48 hours later with human chorionic gonadotropin. Primed females are placed with males and checked for vaginal plugs on the following morning. Pseudo pregnant females are selected for estrus, placed with proved sterile vasectomized males and used as recipients. Zygotes are collected and cumulus cells removed. Furthermore, blastocysts can be harvested. Pronuclear embryos are recovered from female mice mated to males. Females are treated with pregnant mare serum, PMS, to induce follicular growth and human chorionic gonadotropin, hCG, to induce ovulation. Embryos are recovered in a Dulbecco's modified phosphate buffered saline (DPBS) and maintained in Dulbecco's modified essential medium (DMEM) supplemented with 10% fetal bovine serum.

Microinjection of a transgenic construct can be performed using standard micro manipulators attached to a microscope. For instance, embryos are typically held in 100 microliter drops of DPBS under oil while being microinjected. DNA solution is microinjected into the male pronucleus. Successful injection is monitored by swelling of the pronucleus. Recombinant ES cells can be injected into blastocysts, using similar techniques. Immediately after injection embryos are transferred to recipient females, e.g. mature mice mated to vasectomized male mice. In a general protocol, recipient females are anesthetized, paralumbar incisions are made to expose the oviducts, and the embryos are transformed into the ampullary region of the oviducts. The body wall is sutured and the skin closed with wound clips.

Screening for the Presence of the Targeting Construct

Transgenic animals can be identified after birth by standard protocols. DNA from tail tissue can be screened for the presence of the targeting construct using southern blots and/or PCR. Offspring that appear to be mosaics are then crossed to each other if they are believed to carry the targeting construct in their germ line to generate homozygous transgenic animals. If it is unclear whether the offspring will have germ line transmission, they can be crossed with a parental or other strain and the offspring screened for heterozygosity. The heterozygotes are identified by southern blots and/or PCR amplification of the DNA.

The heterozygotes can then be crossed with each other to generate homozygous transgenic offspring. Homozygotes may be identified by southern blotting of equivalent amounts of genomic DNA from mice that are the product of this cross, as well as mice that are known heterozygotes and wild type mice. Probes to screen the southern blots can be designed as set forth above.

Other means of identifying and characterizing the transgenic offspring are known in the art. For example, northern blots can be used to probe the mRNA for the presence or absence of transcripts encoding the reporter gene. In addition, western blots can be used to assess the level of expression of the transgene in various tissues of these offspring by probing the western blot with an antibody against the protein encoded by the transgene, or an antibody against the marker gene product, where this gene is expressed. Finally, in situ analysis (such as fixing the cells and labeling with antibody) and/or FACS (fluorescence activated cell sorting) analysis of various cells from the offspring can be performed using suitable antibodies to look for the presence or absence of the transgene product. Transgenic animals can be generated that have two separate transgenes with distinct promoters operably linked to detectably distinct reporters, e.g., by interbreeding mice transgenic for the individual promoter-reporter transgenes.

Other transgenic animals can be used in methods of the invention. Methods for the preparation of a variety of animals are known in the art. A protocol for the production of a transgenic pig can be found in White and Yannoutsos, Current Topics in Complement Research: 64th Forum in Immunology, pp. 88-94; U.S. Pat. No. 5,523,226; U.S. Pat. No. 5,573,933; PCT Application WO93/25071; and PCT Application WO95/04744. A protocol for the production of a transgenic rat can be found in Bader and Ganten, Clinical and Experimental Pharmacology and Physiology, Supp. 3:S81-S87, 1996. A protocol for the production of a transgenic cow can be found in Transgenic Animal Technology, A Handbook, 1994, ed., Carl A. Pinkert, Academic Press, Inc. A protocol for the production of a transgenic sheep can be found in Transgenic Animal Technology, A Handbook, 1994, ed., Carl A. Pinkert, Academic Press, Inc.

Reporter Genes

Promoter activity can be assayed by coupling a reporter gene to a promoter of interest (e.g., the HGF, HGFR, integrin α9 or stanniocalcin 1 promoter). The reporter gene can be any gene which encodes a detectable product, preferably one which can be detected with relative ease, e.g., a gene product which is fluorescent, or which catalyzes a reaction which can be determined by formation of a colored, fluorescent, or luminescent product. For example, the reporter gene can encode an enzyme, e.g., an enzyme which produces a detectable product, e.g., a colored, fluorescent, luminescent product. Reporter genes are known in the art and include a β-galactosidase gene, a luciferase gene, a green fluorescent protein gene, a cyan fluorescent protein, a yellow fluorescent protein, a red fluorescent protein, an alkaline phosphatase gene, a horseradish peroxidase gene, a β-lactamase gene, or a chloramphenicol acetyl transferase gene. Reporter genes are described in, for example, Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989.

IV. Diagnostic Assays

A. Nucleic Acid and Protein Detection

Arrays are useful molecular tools for characterizing a sample, e.g., a sample from a subject. For example, an array having capture probes for multiple genes, including probes for HGF, HGFR, integrin α9 and stanniocalcin 1 nucleic acids, or for multiple proteins. Arrays can have many addresses, e.g., locatable sites, on a substrate. The featured arrays can be configured in a variety of formats, non-limiting examples of which are described below.

The substrate can be opaque, translucent, or transparent. The addresses can be distributed, on the substrate in one dimension, e.g., a linear array; in two dimensions, e.g., a planar array; or in three dimensions, e.g., a three dimensional array. The solid substrate may be of any convenient shape or form, e.g., square, rectangular, ovoid, or circular.

Arrays can be fabricated by a variety of methods, e.g., photolithographic methods (see, e.g., U.S. Pat. Nos. 5,143,854; 5,510,270; and 5,527,681), mechanical methods (e.g., directed-flow methods as described in U.S. Pat. No. 5,384,261), pin based methods (e.g., as described in U.S. Pat. No. 5,288,514), and bead based techniques (e.g., as described in PCT US/93/04145).

The capture probe can be a single-stranded nucleic acid, a double-stranded nucleic acid (e.g., which is denatured prior to or during hybridization), or a nucleic acid having a single-stranded region and a double-stranded region. Preferably, the capture probe is single-stranded. The capture probe can be selected by a variety of criteria, and preferably is designed by a computer program with optimization parameters. The capture probe can be selected to hybridize to a sequence rich (e.g., non-homopolymeric) region of the gene. The $T_m$ of the capture probe can be optimized by prudent selection of the complementarity region and length. Ideally, the $T_m$ of all capture probes on the array is similar, e.g., within 20, 10, 5, 3, or 2° C. of one another.

The isolated nucleic acid is preferably mRNA that can be isolated by routine methods, e.g., including DNase treatment to remove genomic DNA and hybridization to an oligo-dT coupled solid substrate (e.g., as described in *Current Protocols in Molecular Biology*, John Wiley & Sons, N.Y). The substrate is washed, and the mRNA is eluted.

The isolated mRNA can be reversed transcribed and optionally amplified, e.g., by reverse transcription polymerase chain reaction (RT-PCR), e.g., as described in (U.S. Pat. No. 4,683,202). The nucleic acid can be an amplification product, e.g., from PCR (U.S. Pat. Nos. 4,683,196 and 4,683,202); rolling circle amplification ("RCA," U.S. Pat. No. 5,714,320), isothermal RNA amplification or NASBA (U.S. Pat. Nos. 5,130,238; 5,409,818; and 5,554,517), and strand displacement amplification (U.S. Pat. No. 5,455,166). The nucleic acid can be labeled during amplification, e.g., by the incorporation of a labeled nucleotide. Examples of preferred labels include fluorescent labels, e.g., red-fluorescent dye Cy5™ (Amersham) or green-fluorescent dye Cy3™ (Amersham), and chemiluminescent labels, e.g., as described in U.S. Pat. No. 4,277,437. Alternatively, the nucleic acid can be labeled with biotin, and detected after hybridization with labeled streptavidin, e.g., streptavidin-phycoerythrin (Molecular Probes).

The labeled nucleic acid can be contacted to the array. In addition, a control nucleic acid or a reference nucleic acid can be contacted to the same array. The control nucleic acid or reference nucleic acid can be labeled with a label other than the sample nucleic acid, e.g., one with a different emission maximum. Labeled nucleic acids can be contacted to an array under hybridization conditions. The array can be washed, and then imaged to detect fluorescence at each address of the array.

The expression level of a HGF or HGFR protein can be determined using an antibody specific for the polypeptide (e.g., using a western blot or an ELISA assay). Moreover, the expression levels of multiple proteins, including HGF and HGFR, can be rapidly determined in parallel using a polypeptide array having antibody capture probes for each of the polypeptides. Antibodies specific for a polypeptide can be generated by a method described herein (see "Antibody Generation").

A low-density (96 well format) protein array has been developed in which proteins are spotted onto a nitrocellulose membrane (Ge (2000) *Nucleic Acids Res.* 28, e3, I-VII). A high-density protein array (e.g., 100,000 samples within 222×222 mm) used for antibody screening can be produced by spotting proteins onto polyvinylidene difluoride (PVDF) (Lueking et al. (1999) *Anal. Biochem.* 270:103-111). See also, e.g., Mendoza et al. (1999). *Biotechniques* 27:778-788; MacBeath and Schreiber (2000) *Science* 289:1760-1763; and De Wildt et al. (2000). *Nature Biotech.* 18:989-994. These art-known methods and others can be used to generate an array of antibodies for detecting the abundance of polypeptides in a sample. The sample can be labeled, e.g., biotinylated, for subsequent detection with streptavidin coupled to a fluorescent label. The array can then be scanned to measure binding at each address.

The nucleic acid and polypeptide arrays of the invention can be used in wide variety of applications. For example, the arrays can be used to analyze a patient sample. The sample is compared to data obtained previously, e.g., known clinical specimens or other patient samples. Further, the arrays can be used to characterize a cell culture sample, e.g., to determine a cellular state after varying a parameter, e.g., exposing the cell culture to an antigen, a transgene, or a test compound.

The expression data can be stored in a database, e.g., a relational database such as a SQL database (e.g., Oracle or Sybase database environments). The database can have multiple tables. For example, raw expression data can be stored in one table, wherein each column corresponds to a gene being assayed, e.g., an address or an array, and each row corresponds to a sample. A separate table can store identifiers and sample information, e.g., the batch number of the array used, date, and other quality control information.

Expression profiles obtained from gene expression analysis on an array can be used to compare samples and/or cells in a variety of states as described in Golub et al. ((1999) *Science* 286:531). In one embodiment, expression (e.g., mRNA expression or protein expression) information for a gene encoding HGF and/or a gene encoding HGFR are evaluated, e.g., by comparison a reference value, e.g., a reference value. Reference values can be obtained from a control, a reference subject. Reference values can also be obtained from statistical analysis, e.g., to provide a reference value for a cohort of subject, e.g., age and gender matched subject, e.g., normal subjects or subject who have or at risk for a lymphatic or lymphatic system-related disorder. Statistical similarity to a particular reference (e.g., to a reference for a risk-associated cohort) or a normal cohort can be used to provide an assessment (e.g., an indication of risk a lymphatic disorder) to a subject, e.g., a subject who has not a prior lymphatic disorder, a subject who has a risk for a lymphatic disorder (e.g., a genetic predisposition), or a subject who has had a lymphatic disorder.

Subjects suitable for treatment can also be evaluated for expression and/or activity of HGF/HGFR pathway activity, e.g., HGF expression, HGFR expression, integrin α9 expression and stanniocalcin 1 expression, as well as modification states or other parameters associated with these factors. In some embodiments, subjects can be identified as suitable for treatment if the expression and/or activity for HGF and/or HGFR is altered (e.g., elevated) relative to a reference, e.g., reference value, e.g., a reference value associated with normal.

Subjects who are being administered an agent described herein or other treatment for a lymphatic or lymphatic system-related disorder can be evaluated as described for expression and/or activity of HGF and/or HGFR. The subject can be evaluated at multiple times. e.g., at multiple times during a course of therapy, e.g., during a therapeutic regimen. Treatment of the subject can be modified depending on how the subject is responding to the therapy. For example, a reduction in HGF and/or HGFR expression or activity can be indicative of responsiveness if the agent being administered is an antagonist.

Particular effects mediated by an agent may show a difference (e.g., relative to an untreated subject, control subject, or other reference) that is statistically significant (e.g., P value<0.05 or 0.02). Statistical significance can be determined by any art known method. Exemplary statistical tests include: the Students T-test, Mann Whitney U non-parametric test, and Wilcoxon non-parametric statistical test. Some statistically significant relationships have a P value of less than 0.05 or 0.02.

B. Methods of Evaluating Genetic Material

There are numerous methods for evaluating genetic material to provide genetic information. These methods can be used to evaluate a genetic locus that includes a gene encoding HGF or a gene encoding HGFR, as well as other loci. The methods can be used to evaluate one or more nucleotides, e.g., a coding or non-coding region of the gene, e.g., in a regulatory region (e.g., a promoter, a region encoding an untranslated region or intron, and so forth).

Nucleic acid samples can analyzed using biophysical techniques (e.g., hybridization, electrophoresis, and so forth), sequencing, enzyme-based techniques, and combinations-thereof. For example, hybridization of sample nucleic acids to nucleic acid microarrays can be used to evaluate sequences in an mRNA population and to evaluate genetic polymorphisms. Other hybridization based techniques include sequence specific primer binding (e.g., PCR or LCR); Southern analysis of DNA, e.g., genomic DNA; Northern analysis of RNA, e.g., mRNA; fluorescent probe based techniques (see, e.g., Beaudet et al. (2001) *Genome Res.* 11(4):600-8); and allele specific amplification. Enzymatic techniques include restriction enzyme digestion; sequencing; and single base extension (SBE). These and other techniques are well known to those skilled in the art.

Electrophoretic techniques include capillary electrophoresis and Single-Strand Conformation Polymorphism (SSCP) detection (see, e.g., Myers et al. (1985) *Nature* 313:495-8 and Ganguly (2002) *Hum Mutat.* 19(4):334-42). Other biophysical methods include denaturing high pressure liquid chromatography (DHPLC).

In one embodiment, allele specific amplification technology that depends on selective PCR amplification may be used to obtain genetic information. Oligonucleotides used as primers for specific amplification may carry the mutation of interest in the center of the molecule (so that amplification depends on differential hybridization) (Gibbs et al. (1989) Nucl. Acids Res. 17:2437-2448) or at the extreme 3' end of one primer where, under appropriate conditions, mismatch can prevent, or reduce polymerase extension (Prossner (1993) Tibtech 11:238). In addition, it is possible to introduce a restriction site in the region of the mutation to create cleavage-based detection (Gasparini et al. (1992) Mol. Cell. Probes 6:1). In another embodiment, amplification can be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

Enzymatic methods for detecting sequences include amplification based-methods such as the polymerase chain reaction (PCR; Saiki, et al. (1985) Science 230:1350-1354) and ligase chain reaction (LCR; Wu. et al. (1989) Genomics 4:560-569; Barringer et al. (1990), Gene 1989:117-122; F. Barany (1991) Proc. Natl. Acad. Sci. USA 1988:189-193); transcription-based methods utilize RNA synthesis by RNA polymerases to amplify nucleic acid (U.S. Pat. Nos. 6,066,457; 6,132,997; and 5,716,785; Sarkar et al., (1989) Science 244:331-34; Stofler et al., (1988) Science 239:491); NASBA (U.S. Pat. Nos. 5,130,238; 5,409,818; and 5,554,517); rolling circle amplification (RCA; U.S. Pat. Nos. 5,854,033 and 6,143,495) and strand displacement amplification (SDA; U.S. Pat. Nos. 5,455,166 and 5,624,825). Amplification methods can be used in combination with other techniques.

Other enzymatic techniques include sequencing using polymerases, e.g., DNA polymerases and variations thereof such as single base extension technology. See, e.g., U.S. Pat. Nos. 6,294,336; 6,013,431; and 5,952,174.

Fluorescence based detection can also be used to detect nucleic acid polymorphisms. For example, different terminator ddNTPs can be labeled with different fluorescent dyes. A primer can be annealed near or immediately adjacent to a polymorphism, and the nucleotide at the polymorphic site can be detected by the type (e.g., "color") of the fluorescent dye that is incorporated.

Hybridization to microarrays can also be used to detect polymorphisms, including SNPs. For example, a set of different oligonucleotides, with the polymorphic nucleotide at varying positions with the oligonucleotides can be positioned on a nucleic acid array. The extent of hybridization as a function of position and hybridization to oligonucleotides specific for the other allele can be used to determine whether a particular polymorphism is present. See, e.g., U.S. Pat. No. 6,066,454.

In one implementation, hybridization probes can include one or more additional mismatches to destabilize duplex formation and sensitize the assay. The mismatch may be directly adjacent to the query position, or within 10, 7, 5, 4, 3, or 2 nucleotides of the query position. Hybridization probes can also be selected to have a particular $T_m$, e.g., between 45-60° C., 55-65° C., or 60-75° C. In a multiplex assay, $T_m$s can be selected to be within 5, 3, or 2° C. of each other.

It is also possible to directly sequence the nucleic acid for a particular genetic locus, e.g., by amplification and sequencing, or amplification, cloning and sequence. High throughput automated (e.g., capillary or microchip based) sequencing apparati can be used. In still other embodiments, the sequence of a protein of interest is analyzed to infer its genetic sequence. Methods of analyzing a protein sequence include protein sequencing, mass spectroscopy, sequence/epitope specific immunoglobulins, and protease digestion.

Any combination of the above methods can also be used. The above methods can be used to evaluate any genetic locus, e.g., in a method for analyzing genetic information from particular groups of individuals or in a method for analyzing a polymorphism associated with a lymphatic or lymphatic system-related disorder, e.g., in a gene encoding HGF, HGFR, integrin α9 or stanniocalcin 1.

C. In Vivo Imaging

HGFR HGF/HGFR binding agents (e.g., antibodies) can be used detecting the presence of HGF and/or HGFR in vivo (e.g., in vivo imaging in a subject), respectively. The method can be used to evaluate (e.g., diagnose, localize, or stage) a condition described herein, e.g., a lymphatic disorder or risk for such a disorder. The method includes: (i) administering to a subject (and optionally a control subject) a HGF/HGFR binding agent (e.g., an antibody that binds to HGF or HGFR), under conditions that allow interaction of the binding agent and HGF or HGFR to occur; and (ii) detecting the binding agent, for example, to locate or otherwise identify HGF or HGFR expressing cells. A statistically significant increase in the amount of the complex in the subject relative to the reference, e.g., the control subject or subject's baseline, can be a factor that may lead to a diagnosis of a lymphatic or lymphatic system-related disorder or risk for such a disorder.

Preferably, the HGF/HGFR binding agent used in the in vivo (and also in vitro) diagnostic methods is directly or indirectly labeled with a detectable substance to facilitate detection of the bound or unbound binding agent. Suitable detectable substances include various enzymes, prosthetic groups, fluorescent materials, luminescent materials and radioactive materials. In one embodiment, the HGF or HGFR binding protein is coupled to a radioactive ion, e.g., indium (111In), iodine (131I or 125I), yttrium (90Y), actinium (225Ac), bismuth (212Bi or 213Bi), sulfur (35S), carbon (14C), tritium (3H), rhodium (188Rh), or phosphorous (32P). In another embodiment, the HGF/HGFR binding protein is labeled with an NMR contrast agent.

In one aspect, the invention features a method of imaging vasculature (e.g., lymphatic vasculature) in a patient who is at risk for a lymphatic or lymphatic system-related disorder, or has such a disorder which is progressing. The method includes: providing an agent that binds to HGF or HGFR, e.g., an agent described herein, wherein the protein is physically associated to an imaging agent; administering the agent to a patient, e.g., with a risk for a lymphatic or lymphatic system-related disorder; and locating the agent within the patient, e.g., by imaging the patient, e.g., to detect HGF or HGFR expressing cells.

EXAMPLES

Example 1

HGFR is Expressed at a Higher Level in Lymphatic Endothelial Cells than in Blood Vascular Endothelial Cells and is Functional Quantitative real-time RT-PCR (QPCR) confirmed that three independently established lines of primary LEC expressed high levels of mRNA of the major lymphatic lineage markers Prox1 and LYVE-1 but expressed low levels of the blood vascular lineage marker Flt-1, relative to blood vascular endothelial cells (BVEC) (FIG. 1A-C). HGFR mRNA levels in LEC were measured by QPCR and found to be at more than 2-fold higher than levels in BVEC (FIG. 1D).

In addition, immunoprecipitation and western blot analyses demonstrated that HGFR protein expression was higher in LEC than in BVEC (FIG. 1E). Since treatment of LEC with 30 ng/ml HGF resulted in increased phosphorylation of HGFR (FIG. 1F), HGFR is functional in LEC. In sum, HGFR is expressed at a higher level in LEC than in BVEC and is activated when LEC are treated with HGF.

Example 2

Figure 2:
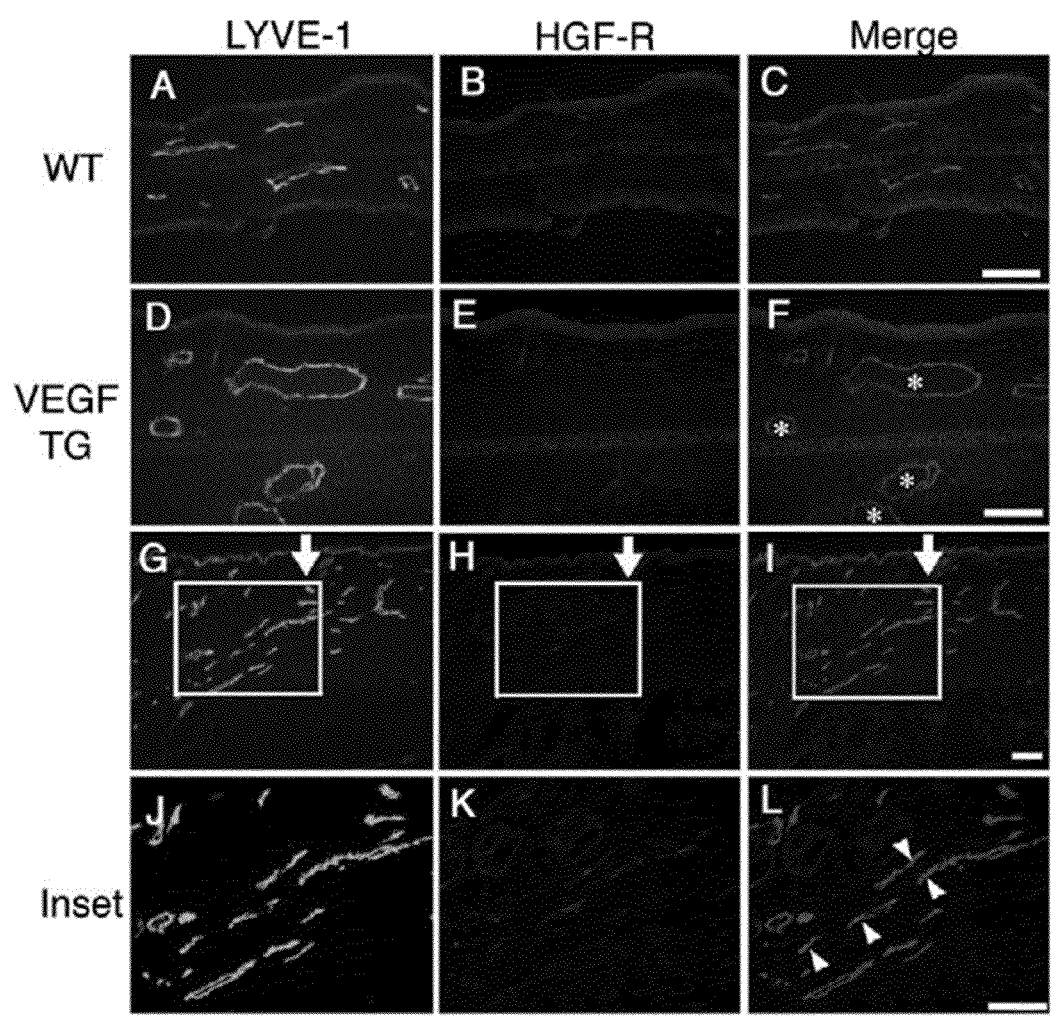
FIG. 2A-L show dual immunofluorescence staining for the lymphatic marker LYVE-1 (green) and for HGFR (red), in lymphatic vessels.

HGFR Expression is Expressed in Lymphatic Vessels During Inflammation and Tissue Repair In Vivo Differential immunofluorescence analyses of normal mouse skin were performed, using antibodies against HGFR and against the lymphatic-specific hyaluronan receptor LYVE-1. Little or no expression of HGFR was detected in quiescent lymphatic vessels in normal skin. In order to determine whether HGFR might be upregulated by lymphatic endothelium during pathological processes, we immunostained samples of chronically inflamed murine skin obtained from experimentally induced delayed-type hypersensitivity reactions in VEGF-A transgenic (VEGF-TG) mice that are characterized by lymphatic vessel enlargement and proliferation, Kunstfeld et al. (2004), Blood, 104(4):1048-1057. Seven days after induction of skin inflammation, enlarged LYVE-1-positive lymphatic vessels were detected in VEGF-TG mice but not in wild-type mice (FIG. 2A, D). LYVE-1-positive lymphatic vessels strongly expressed HGFR, whereas little or no HGFR expression was detected in the normal lymphatic vessels of wild-type mice (FIG. 2A-F).

Two to three weeks after experimentally-induced full-thickness skin wounds in mice, pronounced lymphangiogenesis is found within the granulation tissue. Double immunofluorescence analyses of wound tissue at day 21 after wounding revealed several LYVE-1-positive lymphatic vessels that also expressed HGFR (FIG. 2G-L).

Figure 3:
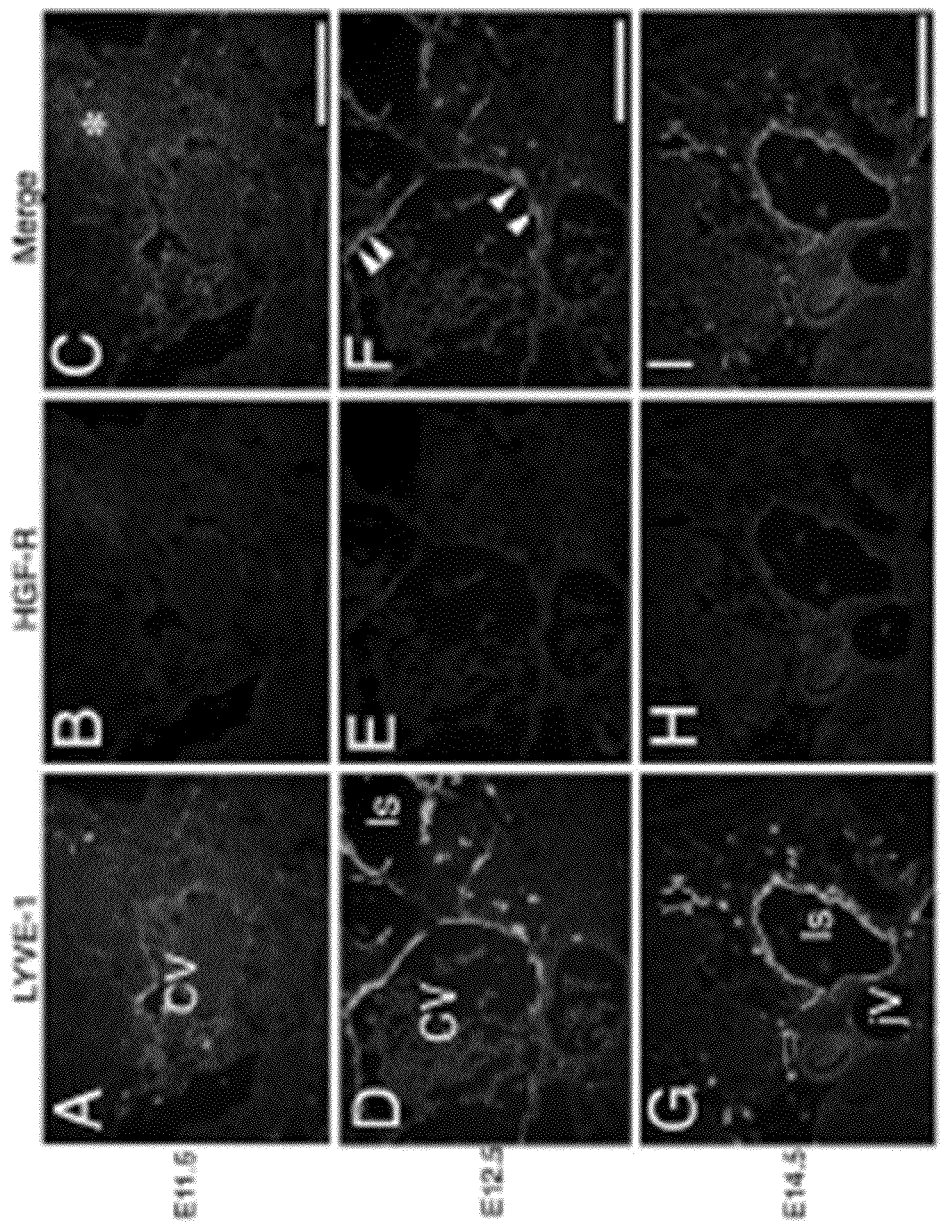
FIG. 3A-I show dual immunofluorescence for the lymphatic marker LYVE-1 (green) and HGFR (red) in endothelial cells of lymph sacs during mouse embryonic development.

To further characterize the possible role of HGFR during embryonic lymphatic vessel formation, mouse embryonic tissues were examined at embryonic days (E) 10.5 to 14.5 when active budding and proliferation of lymphatic vessel progenitors occurs. At E11.5, LYVE-1 expression was detected on endothelial cells of the anterior cardinal vein. These cells expressed little or no HGFR, whereas HGFR expression was already detected within the pharyngeal region of the foregut and in mesenchymal cells (FIG. 3A-C). However, at E12.5, HGFR expression was clearly detectable on LYVE-1-positive endothelial cells of the anterior cardinal vein (FIG. 3F: arrowheads), whereas only occasional HGFR expression was found on endothelial cells lining the primitive lymph sacs, overlapping with LYVE-1 reactivity (FIG. 3D-F). By E14.5, strong HGFR expression was detected on the vast majority of LYVE-1-positive lymphatic endothelial cells (FIG. 3G-I). At this stage, HGFR was still weakly expressed by endothelial cells lining the jugular vein and artery, which were LYVE-1-negative.

Example 3

HGF Directly Promotes LEC Proliferation and Migration

Figure 4:
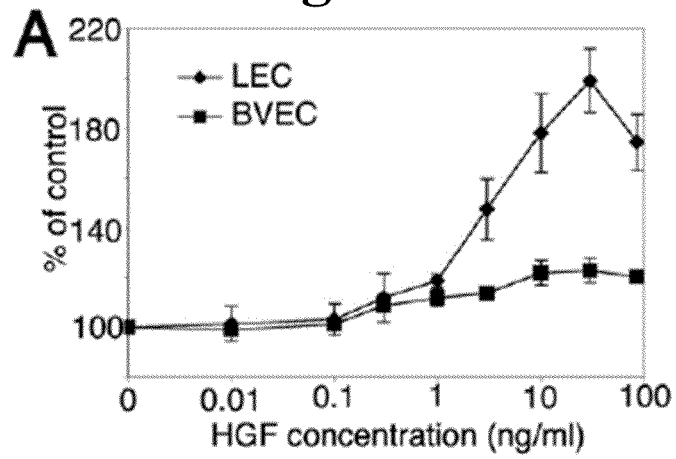
FIG. 4 shows data for lymphatic endothelial cell (LEC) proliferation (A and B) and migration assay (C) for LEC cells treated with HGF.
Figure 4:
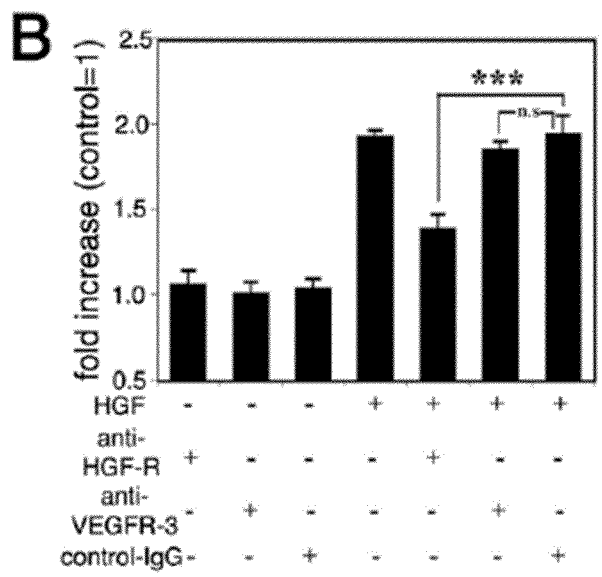
Figure 4:
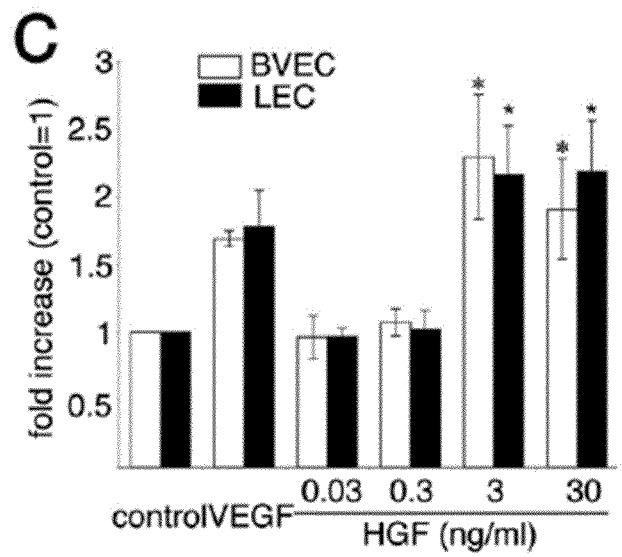

HGF is the only known ligand of HGFR and has been shown to induce proliferation and migration of human vascular endothelial cells (HVEC), e.g., Bussolino et al. (1992), J. Cell Biol., 119:629-641. To investigate whether the differential expression levels of HGFR by LEC versus BVEC might result in their differential response toward HGF stimulation, we next investigated the effects of HGF on LEC versus BVEC proliferation in vitro. HGF potently induced LEC proliferation with a minimal effective concentration of 1 ng/ml ($p<0.01$), as compared with untreated control cultures. Although HGF also induced BVEC proliferation at this concentration, the extent of growth stimulation was higher in LEC than in BVEC (FIG. 4A). Thus far, VEGF-C and VEGF-D are the only known growth factors that directly promote LEC proliferation via activation of the VEGF receptor-3 (VEGFR-3), e.g., Jussila and Alitalo (2002), Physiol Rev, 82:673-700, and effects of FGF-2 on lymphangiogenesis have been proposed to be the result of upregulation of VEGFR-3 ligands because they could be inhibited by blockade of the VEGFR-3 pathway, e.g., Chang et al. (2004), PNAS, 101:11658-11663; Kubo et al. (2002), PNAS, 99:8868-8873. To investigate whether HGF directly or indirectly stimulates LEC proliferation, we next treated LEC with HGF, in the presence or absence of blocking antibodies against VEGFR-3 or HGFR. Incubation of LEC with a HGFR blocking antibody potently blocked the stimulation of LEC proliferation by HGF ($p<0.001$), whereas incubation with a VEGFR-3 blocking antibody—at a dose that efficiently blocked growth stimulation by VEGF-C (data not shown)—or with control IgG did not affect HGF-induced proliferation (FIG. 4B). These results indicate that HGF-induced LEC proliferation occurs independently from activation of the VEGF-R3 pathway and is dependent upon efficient binding of HGF to its receptor.

Figure 5:
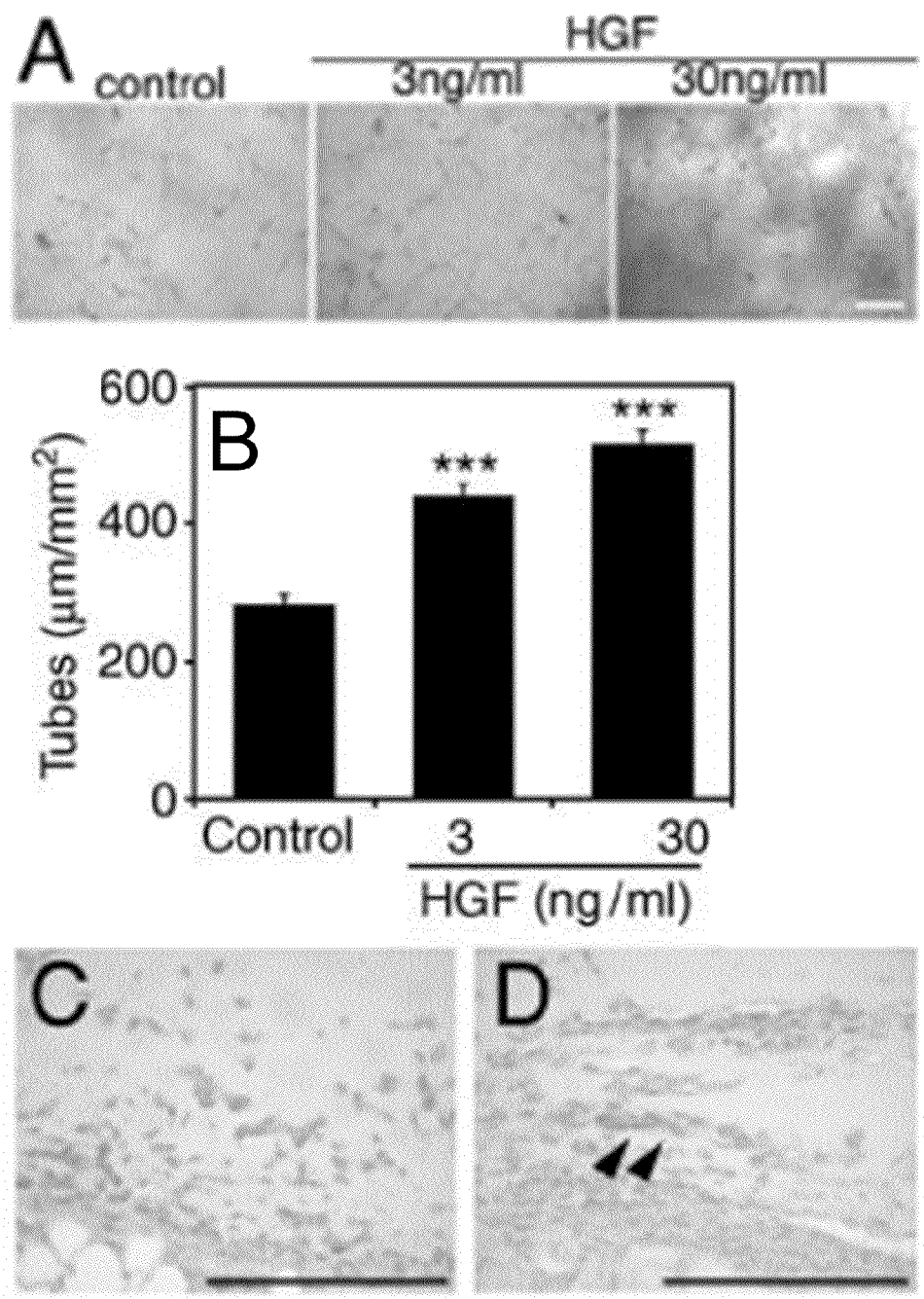
FIG. 5A D show data for LEC tube formation in vitro, in response to HGF and lymphatic vessel formation in vivo.

HGF treatment also dose-dependently promoted migration of LEC and BVEC, with a minimal effective concentration of 3 ng/ml (FIG. 4C). To investigate whether HGF stimulation might also promote the formation of lymphatic tubes in vitro, confluent LEC cultures were overlaid with type I collagen as previously described Hirakawa et al. (2003), Am. J. Pathol., 162:575-586. HGF potently induced cord formation by LEC with a minimal effective dose of 3 ng/ml ($p<0.001$), as compared with untreated control cultures (FIG. 5A, B).

Example 4

HGF Promotes Lymphatic Vessel Formation In Vivo

To investigate whether HGF might also induce lymphangiogenesis in vivo, we implanted matrigels with or without HGF subcutaneously into FVB mice as described in Hirakawa et al. (2003), Am. J. Pathol., 162:575-586. Immunostaining for the lymphatic-specific glycoprotein podoplanin, e.g., Schacht et al. (2003), EMBO J., 22:3546-3556, revealed pronounced formation of new lymphatic vessels within HGF-containing matrigels at day 7 after implantation, whereas no lymphatic vessels were observed within control matrigels (FIG. 5C,D).

Example 5

Figure 6:
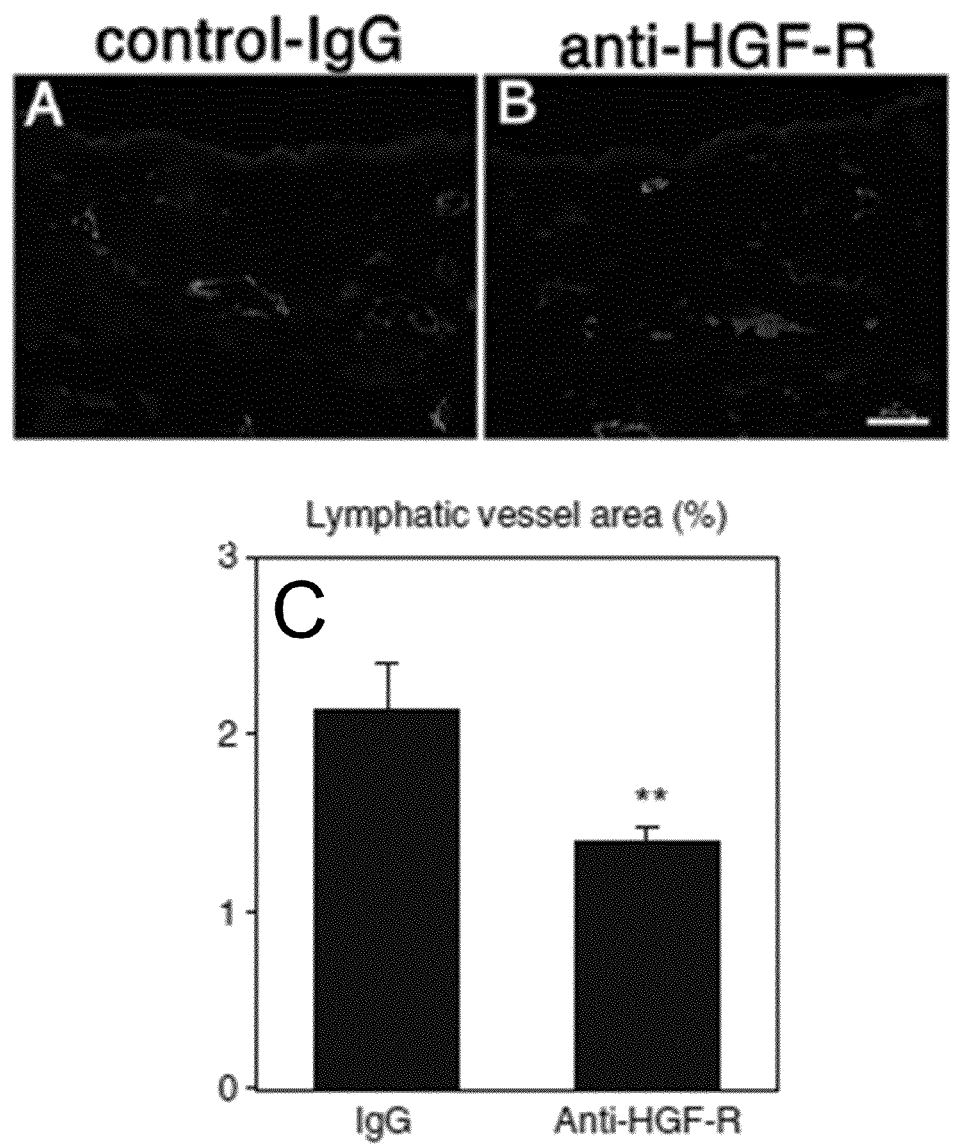
FIG. 6A-E show dual immunofluorescence staining of lymphatic vessels for LYVE-1 (green) and CD31 (red) after experimental skin inflammation.
Figure 6:
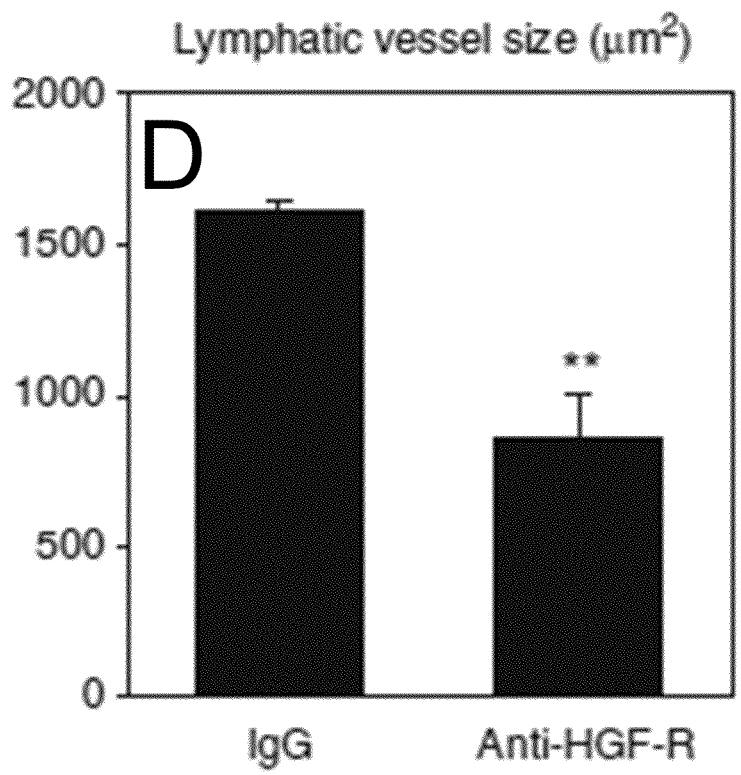
Figure 6:
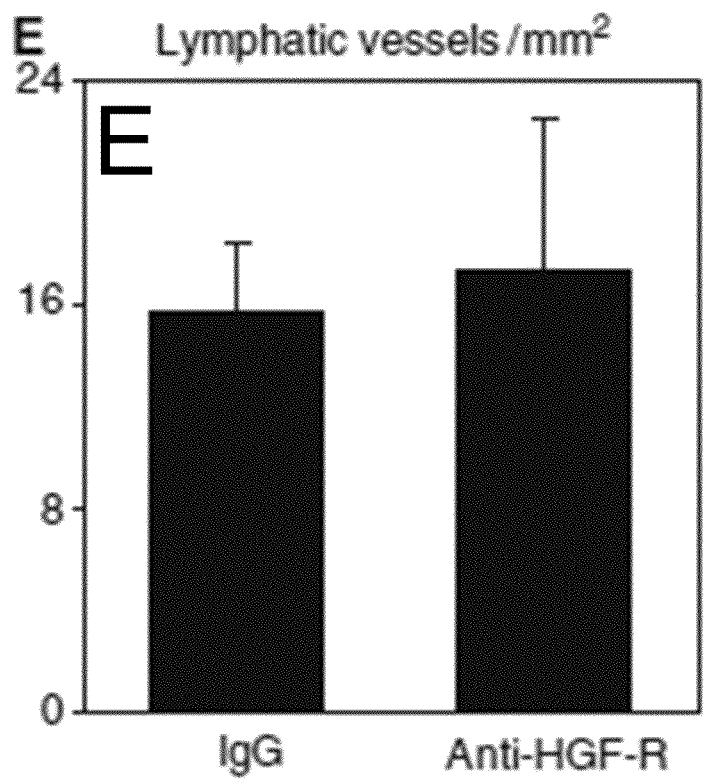

Systemic Blockade of HGFR Inhibits Lymphatic Vessel Enlargement During Experimental Skin Inflammation Because we found that HGFR was strongly expressed by the enlarged lymphatic vessels during experimental skin inflammation in mice, we next investigated whether HGF might directly contribute to lymphatic vessel enlargement in vivo. Delayed-type hypersensitivity reactions were induced by topical application to mouse ears as described Kunstfeld et al. (2004), Blood, 104(4):1048-1057. One day prior to induction of experimental inflammation, 100 μg of a blocking antibody against HGFR or an equal amount of control immunoglobulin G were injected intraperitoneally. Immunofluorescence analyses at 24 hours after induction of inflammation revealed a greatly reduced size of lymphatic vessels in mice that had received treatment with the HGF-R blocking antibody, as compared with mice that had received control IgG (FIG. 6A, B). Computer-assisted morphometric analyses of sections stained for LYVE-1 and CD31 demonstrated that the average size of lymphatic vessels, and the percentage of tissue area covered by lymphatic vessels, were significantly decreased after injection of the HGF-R blocking antibody (P<0.01), as compared with control IgG-treated mice (FIG. 6C, D). The density of lymphatic vessels was not significantly different between the two treatment groups (FIG. 6E).

Example 6

HGF Promotes LEC Migration Via Integrin α9

To define possible molecular mechanisms that might mediate the effects of HGF on LEC, two independent lines of LEC were incubated with or without 30 ng/ml HGF for 6 hours, followed by microarray analyses using the Affymetrix HU133v2™ arrays. We found that stanniocalcin 1 was one of the most highly up-regulated genes after HGF treatment. Moreover, the expression of the integrin alpha 9 was also significantly upregulated after HGF treatment. These results were confirmed by QPCR analysis (FIG. 7A).

Figure 7:
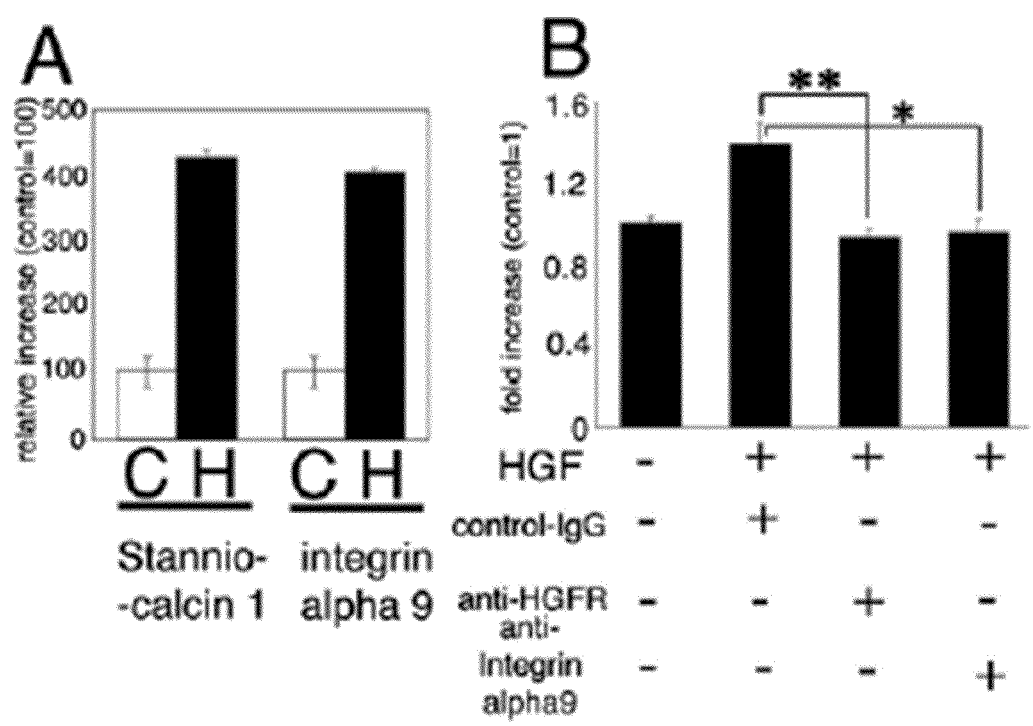
FIG. 7A and B show QPCR data for integrin α9 and stanniocalcin 1 mRNA levels in LEC after treatment with HGF.

Co-incubation of LEC with HGF in the presence or absence of a specific integrin alpha 9 blocking antibody revealed that blockade of the integrin alpha 9 partially blocked HGF-induced migration (p=0.0143), whereas incubation with a HGF-R blocking antibody completely inhibited the effect of HGF on LEC migration (p=0.0074) (FIG. 7B).

Example 7

HGF Promotes Lymphatic Vessel Formation In Vivo Independently of VEGF

Figure 8:
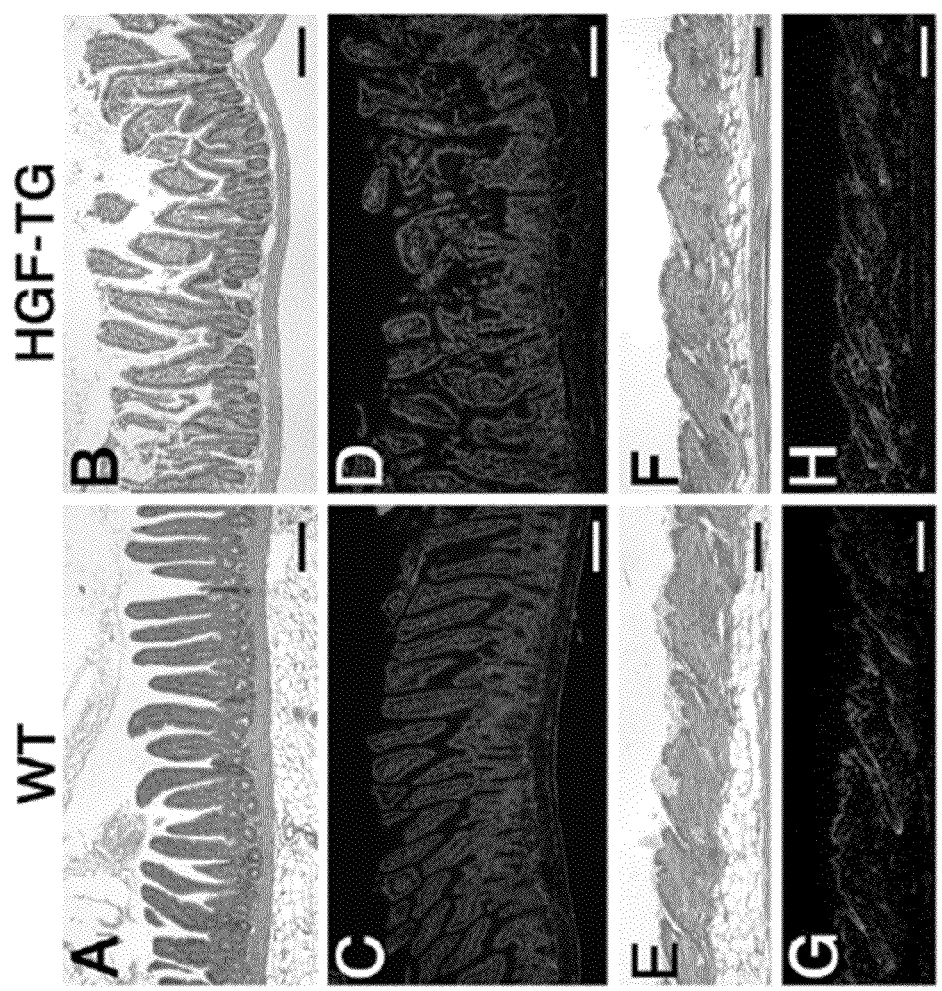
FIG. 8 shows representative histologic images (H&E stain and immunofluorescence to detect podoplanin) of the ileum in HGF transgenic (FIGS. 8 B,D,F,H) and wild-type mice (FIGS. 8 A,C,E,G). Scale bars: 100 µm.

To determine the effect of HGF overexpression in vivo, the lymphatic vasculature was investigated in previously established metallothionein I promoter-driven HGF transgenic mice (Takayama et al. (1996) Proc. Natl. Acad. Sci. USA, 93:5866-5871). The analysis focused on the skin and the small intestine where lymphatic vessels are most abundant and where abnormalities of the lymphatic system are most easily detected in genetic mouse models. Vascular enlargement was detected in the mucosa and submucosa of the ileum in HGF transgenic mice (FIG. 8B), as compared with wild-type mice (FIG. 8A). Immunofluorescence stains for the lymphatic-specific marker podoplanin revealed pronounced dilation of central lacteals and enlargement of lymphatic vessels in the submucosa of the ileum in HGF transgenic mice (FIG. 8C, D). Podoplanin stains also revealed an increased number and an enlargement of lymphatic vessels in the skin of HGF transgenic mice (FIG. 8G, H), whereas no major histological abnormalities were observed (FIG. 8E, F). Enhanced lymphatic vessel formation and enlargement were also observed in the duodenum and liver of HGF transgenic mice.

Figure 9:
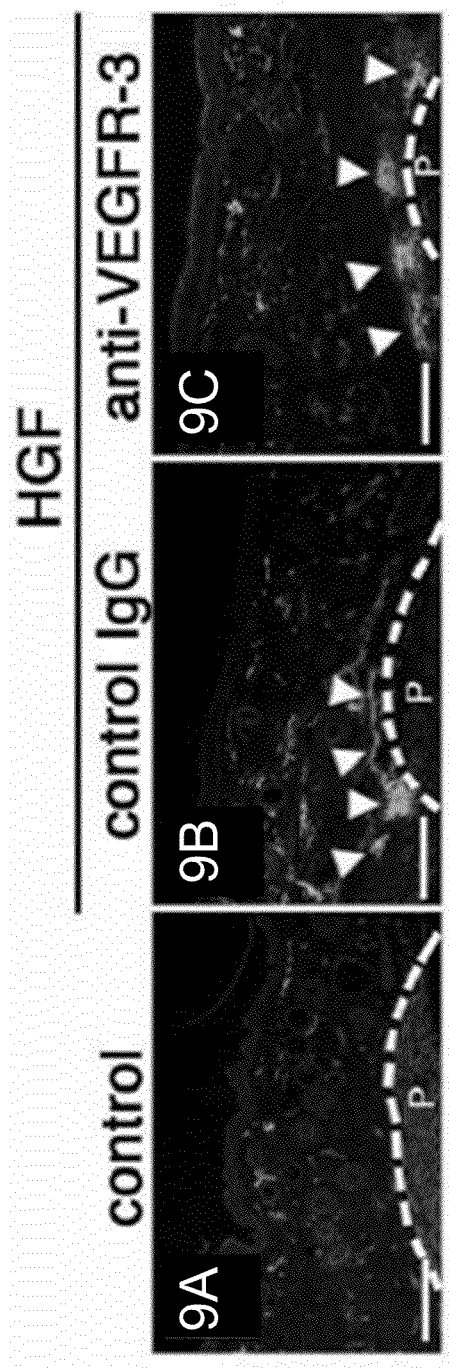
FIG. 9 shows double immunofluorescence analyses of mouse ear sections for LYVE-1 (green) and CD31 (red). Induction of LYVE-1-positive lymphatic vessel formation was observed at 14 days after implantation of HGF-containing slow-release pellets (9B and C; arrowheads) but not of control pellets (9A). Systemic treatment with a blocking anti-VEGFR-3 antibody (9C) did not inhibit HGF-induced lymphatic vessel formation, as compared with control IgG treatment (9B). Newly formed blood vessels were observed in all samples. P: Pellet. Scale bars: 100 µm.

To examine whether HGF promotes the formation of new lymphatic vessels directly or indirectly via the VEGFR-3 pathway, slow-release pellets (with or without HGF) were implanted subcutaneously into mouse ears, and mice were treated systemically with a blocking antibody against mouse VEGFR-3 or with control IgG. After 14 days, immunofluorescence stains for CD31 and LYVE-1 revealed pronounced lymphatic vessel formation surrounding HGF-containing pellets, but not surrounding control pellets (FIG. 9A-C). However, treatment with an anti-VEGFR-3 blocking antibody did not prevent lymphatic vessel formation induced by HGF (FIG. 9B, C). Mice implanted with HGF-containing pellets showed moderately enhanced formation of blood vessels.

The results shown in these examples indicate that HGF is a protein target for controlling lymphangiogenesis.

OTHER EMBODIMENTS

A number of embodiments of the invention have been described. Nevertheless, it will be understood that various modifications may be made without departing from the spirit and scope of the invention. For example, combinations of nucleic acid and antibody modulators of HGF and HGFR activity are contemplated. Accordingly, other embodiments are within the scope of the following claims.

What is claimed is:

1. A method of treating a subject diagnosed as having lymphedema, the method comprising:
   selecting a subject diagnosed as having lymphedema;
   administering to the subject a pharmaceutical composition comprising a purified nucleic acid molecule comprising a sequence that encodes a wildtype hepatocyte growth factor (HGF) protein in an amount sufficient to promote lymph vessel formation in the subject.

2. The method of claim 1, wherein the wildtype HGF protein is a wildtype human HGF protein.

3. The method of claim 1, wherein the pharmaceutical composition is administered by intravenous injection, subcutaneous injection, intramuscular injection, or intraperitoneal injection.

4. The method of claim 1, wherein the pharmaceutical composition is administered in a single dose.

5. The method of claim 1, wherein the pharmaceutical composition is administered in multiple doses.

6. The method of claim 1, wherein the pharmaceutical composition includes a pharmaceutically acceptable carrier.

7. A method of treating a subject diagnosed as having lymphedema, the method comprising:
   selecting a subject diagnosed as having lymphedema;
   administering to the subject a pharmaceutical composition comprising a purified nucleic acid molecule comprising a sequence that encodes a hepatocyte growth factor (HGF) protein comprising a sequence at least 90% identical to amino acids 55 to 728 of SEQ ID NO: 1 and having lymphangiogenic activity, in an amount sufficient to promote lymph vessel formation in the subject.

8. The method of claim 7, wherein the HGF protein comprises a sequence at least 92% identical to amino acids 55 to 728 of SEQ ID NO: 1.

9. The method of claim 8, wherein the HGF protein comprises a sequence at least 95% identical to amino acids 55 to 728 of SEQ ID NO: 1.

10. The method of claim 9, wherein the HGF protein comprises a sequence at least 97% identical to amino acids 55 to 728 of SEQ ID NO: 1.

11. The method of claim 10, wherein the HGF protein comprises a sequence at least 99% identical to amino acids 55 to 728 of SEQ ID NO: 1.

12. The method of claim 11, wherein the HGF protein comprises amino acids 55 to 728 of SEQ ID NO: 1.

13. The method of claim 7, wherein the pharmaceutical composition is administered by intravenous injection, subcutaneous injection, intramuscular injection, or intraperitoneal injection.

14. The method of claim 7, wherein the pharmaceutical composition is administered in a single dose.

15. The method of claim 7, wherein the pharmaceutical composition is administered in multiple doses.

16. The method of claim 7, wherein the pharmaceutical composition includes a pharmaceutically acceptable carrier.

* * * * *

SEQUENCE LISTING

```
<160> NUMBER OF SEQ ID NOS: 8

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
```

```
                65                  70                  75                  80
Pro Phe Thr Cys Lys Ala Phe Val Phe Asp Lys Ala Arg Lys Gln Cys
                    85                  90                  95
Leu Trp Phe Pro Phe Asn Ser Met Ser Ser Gly Val Lys Lys Glu Phe
                100                 105                 110
Gly His Glu Phe Asp Leu Tyr Glu Asn Lys Asp Tyr Ile Arg Asn Cys
                115                 120                 125
Ile Ile Gly Lys Gly Arg Ser Tyr Lys Gly Thr Val Ser Ile Thr Lys
130                 135                 140
Ser Gly Ile Lys Cys Gln Pro Trp Ser Ser Met Ile Pro His Glu His
145                 150                 155                 160
Ser Phe Leu Pro Ser Ser Tyr Arg Gly Lys Asp Leu Gln Glu Asn Tyr
                165                 170                 175
Cys Arg Asn Pro Arg Gly Glu Glu Gly Gly Pro Trp Cys Phe Thr Ser
                180                 185                 190
Asn Pro Glu Val Arg Tyr Glu Val Cys Asp Ile Pro Gln Cys Ser Glu
                195                 200                 205
Val Glu Cys Met Thr Cys Asn Gly Glu Ser Tyr Arg Gly Leu Met Asp
210                 215                 220
His Thr Glu Ser Gly Lys Ile Cys Gln Arg Trp Asp His Gln Thr Pro
225                 230                 235                 240
His Arg His Lys Phe Leu Pro Glu Arg Tyr Pro Asp Lys Gly Phe Asp
                245                 250                 255
Asp Asn Tyr Cys Arg Asn Pro Asp Gly Gln Pro Arg Pro Trp Cys Tyr
                260                 265                 270
Thr Leu Asp Pro His Thr Arg Trp Glu Tyr Cys Ala Ile Lys Thr Cys
                275                 280                 285
Ala Asp Asn Thr Met Asn Asp Thr Asp Val Pro Leu Glu Thr Thr Glu
290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                325                 330                 335
His Asp Met Thr Pro Glu Asn Phe Lys Cys Lys Asp Leu Arg Glu Asn
                340                 345                 350
Tyr Cys Arg Asn Pro Asp Gly Ser Glu Ser Pro Trp Cys Phe Thr Thr
                355                 360                 365
Asp Pro Asn Ile Arg Val Gly Tyr Cys Ser Gln Ile Pro Asn Cys Asp
                370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                405                 410                 415
Lys Asn Met Glu Asp Leu His Arg His Ile Phe Trp Glu Pro Asp Ala
                420                 425                 430
Ser Lys Leu Asn Glu Asn Tyr Cys Arg Asn Pro Asp Asp Asp Ala His
                435                 440                 445
Gly Pro Trp Cys Tyr Thr Gly Asn Pro Leu Ile Pro Trp Asp Tyr Cys
                450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                485                 490                 495
```

Asn Gly Ile Pro Thr Arg Thr Asn Ile Gly Trp Met Val Ser Leu Arg
            500                 505                 510

Tyr Arg Asn Lys His Ile Cys Gly Ser Leu Ile Lys Glu Ser Trp
            515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
                580                 585                 590

Phe Val Ser Thr Ile Asp Leu Pro Asn Tyr Gly Cys Thr Ile Pro Glu
                595                 600                 605

Lys Thr Ser Cys Ser Val Tyr Gly Trp Gly Tyr Thr Gly Leu Ile Asn
            610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
                660                 665                 670

Tyr Gly Gly Pro Leu Val Cys Glu Gln His Lys Met Arg Met Val Leu
            675                 680                 685

Gly Val Ile Val Pro Gly Arg Gly Cys Ala Ile Pro Asn Arg Pro Gly
            690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 696
<212> TYPE: PRT
<213> ORGANISM: Pan troglodytes

<400> SEQUENCE: 2

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys His Glu Thr Phe Gly
        115                 120                 125

Arg Phe Leu Pro Ser Ser Tyr Arg Gly Lys Asp Leu Gln Glu Asn Tyr

-continued

```
            130                 135                 140
Cys Arg Asn Pro Arg Gly Glu Glu Gly Gly Pro Trp Cys Phe Thr Ser
145                 150                 155                 160
Asn Pro Glu Val Arg Tyr Glu Val Cys Asp Ile Pro Gln Cys Ser Glu
                    165                 170                 175
Val Glu Cys Met Thr Cys Asn Gly Glu Ser Tyr Arg Gly Leu Met Asp
                180                 185                 190
His Thr Glu Ser Gly Lys Ile Cys Gln Arg Trp Asp His Gln Thr Pro
                195                 200                 205
His Arg His Lys Phe Leu Pro Glu Arg Tyr Pro Asp Lys Gly Phe Asp
            210                 215                 220
Asp Asn Tyr Cys Arg Asn Pro Asp Gly Gln Pro Arg Pro Trp Cys Tyr
225                 230                 235                 240
Thr Leu Asp Pro His Thr Arg Trp Glu Tyr Cys Ala Ile Lys Thr Cys
                    245                 250                 255
Ala Asp Asn Thr Met Asn Asp Thr Asp Val Pro Leu Glu Thr Thr Glu
                260                 265                 270
Cys Ile Gln Gly Gln Gly Glu Gly Tyr Arg Gly Thr Val Asn Thr Ile
                275                 280                 285
Trp Asn Gly Ile Pro Cys Gln Arg Trp Asp Ser Gln Tyr Pro His Glu
            290                 295                 300
His Asp Met Thr Pro Glu Asn Phe Lys Cys Lys Asp Leu Arg Glu Asn
305                 310                 315                 320
Tyr Cys Arg Asn Pro Asp Gly Ser Glu Ser Pro Trp Cys Phe Thr Thr
                    325                 330                 335
Asp Pro Asn Ile Arg Val Gly Tyr Cys Ser Gln Ile Pro Asn Cys Asp
                340                 345                 350
Met Ser His Gly Gln Asp Cys Tyr Arg Gly Asn Gly Lys Asn Tyr Met
                355                 360                 365
Gly Asn Leu Ser Gln Thr Arg Ser Gly Leu Thr Cys Ser Met Trp Asp
            370                 375                 380
Lys Asn Met Glu Asp Leu His Arg His Ile Phe Trp Glu Pro Asp Ala
385                 390                 395                 400
Ser Lys Leu Asn Glu Asn Tyr Cys Arg Asn Pro Asp Asp Asp Ala His
                    405                 410                 415
Gly Pro Trp Cys Tyr Thr Gly Asn Pro Leu Ile Pro Trp Asp Tyr Cys
                420                 425                 430
Pro Ile Ser Arg Cys Glu Gly Asp Thr Thr Pro Thr Ile Val Asn Leu
                435                 440                 445
Asp His Pro Val Ile Ser Cys Ala Lys Thr Lys Gln Leu Arg Val Val
            450                 455                 460
Asn Gly Ile Pro Thr Arg Thr Asn Val Gly Trp Met Val Ser Leu Arg
465                 470                 475                 480
Tyr Arg Asn Lys His Ile Cys Gly Gly Ser Leu Ile Lys Glu Ser Trp
                    485                 490                 495
Val Leu Thr Ala Arg Gln Cys Phe Pro Ser Arg Asp Leu Lys Asp Tyr
                500                 505                 510
Glu Ala Trp Leu Gly Ile His Asp Val His Gly Arg Gly Asp Glu Lys
                515                 520                 525
Cys Lys Gln Val Leu Asn Val Ser Gln Leu Val Tyr Gly Pro Glu Gly
            530                 535                 540
Ser Asp Leu Val Leu Met Lys Leu Ala Arg Pro Ala Val Leu Asp Asp
545                 550                 555                 560
```

```
Phe Val Ser Thr Ile Asp Leu Pro Asn Tyr Gly Cys Thr Ile Pro Glu
                565                 570                 575

Lys Thr Ser Cys Ser Val Tyr Gly Trp Gly Tyr Thr Gly Leu Ile Asn
                580                 585                 590

Tyr Asp Gly Leu Leu Arg Val Ala His Leu Tyr Ile Met Gly Asn Glu
            595                 600                 605

Lys Cys Ser Gln His His Arg Gly Lys Val Thr Leu Asn Glu Ser Glu
            610                 615                 620

Ile Cys Ala Gly Ala Glu Lys Ile Gly Ser Gly Pro Cys Glu Gly Asp
625                 630                 635                 640

Tyr Gly Gly Pro Leu Val Cys Glu Gln His Lys Met Arg Met Val Leu
                645                 650                 655

Gly Val Ile Val Pro Gly Arg Gly Cys Ala Ile Pro Asn Arg Pro Gly
                660                 665                 670

Ile Phe Val Arg Val Ala Tyr Tyr Ala Lys Trp Ile His Lys Ile Ile
            675                 680                 685

Leu Thr Tyr Lys Val Pro Gln Ser
            690                 695

<210> SEQ ID NO 3
<211> LENGTH: 728
<212> TYPE: PRT
<213> ORGANISM: Mus musculus

<400> SEQUENCE: 3

Met Met Trp Gly Thr Lys Leu Leu Pro Val Leu Leu Leu Gln His Val
  1               5                  10                  15

Leu Leu His Leu Leu Leu His Val Ala Ile Pro Tyr Ala Glu Gly
            20                  25                  30

Gln Lys Lys Arg Arg Asn Thr Leu His Glu Phe Lys Lys Ser Ala Lys
            35                  40                  45

Thr Thr Leu Thr Lys Glu Asp Pro Leu Leu Lys Ile Lys Thr Lys Lys
        50                  55                  60

Val Asn Ser Ala Asp Glu Cys Ala Asn Arg Cys Ile Arg Asn Arg Gly
 65                  70                  75                  80

Phe Thr Phe Thr Cys Lys Ala Phe Val Phe Asp Lys Ser Arg Lys Arg
                85                  90                  95

Cys Tyr Trp Tyr Pro Phe Asn Ser Met Ser Ser Gly Val Lys Lys Gly
            100                 105                 110

Phe Gly His Glu Phe Asp Leu Tyr Glu Asn Lys Asp Tyr Ile Arg Asn
            115                 120                 125

Cys Ile Ile Gly Lys Gly Gly Ser Tyr Lys Gly Thr Val Ser Ile Thr
        130                 135                 140

Lys Ser Gly Ile Lys Cys Gln Pro Trp Asn Ser Met Ile Pro His Glu
145                 150                 155                 160

His Ser Phe Leu Pro Ser Ser Tyr Arg Gly Lys Asp Leu Gln Glu Asn
                165                 170                 175

Tyr Cys Arg Asn Pro Arg Gly Glu Glu Gly Gly Pro Trp Cys Phe Thr
            180                 185                 190

Ser Asn Pro Glu Val Arg Tyr Glu Val Cys Asp Ile Pro Gln Cys Ser
            195                 200                 205

Glu Val Glu Cys Met Thr Cys Asn Gly Glu Ser Tyr Arg Gly Pro Met
        210                 215                 220

Asp His Thr Glu Ser Gly Lys Thr Cys Gln Arg Trp Asp Gln Gln Thr
```

-continued

```
            225                 230                 235                 240
        Pro His Arg His Lys Phe Leu Pro Glu Arg Tyr Pro Asp Lys Gly Phe
                        245                 250                 255

Asp Asp Asn Tyr Cys Arg Asn Pro Asp Gly Lys Pro Arg Pro Trp Cys
                        260                 265                 270

Tyr Thr Leu Asp Pro Asp Thr Pro Trp Glu Tyr Cys Ala Ile Lys Thr
                        275                 280                 285

Cys Ala His Ser Ala Val Asn Glu Thr Asp Val Pro Met Glu Thr Thr
        290                 295                 300

Glu Cys Ile Gln Gly Gln Gly Glu Gly Tyr Arg Gly Thr Ser Asn Thr
        305                 310                 315                 320

Ile Trp Asn Gly Ile Pro Cys Gln Arg Trp Asp Ser Gln Tyr Pro His
                        325                 330                 335

Lys His Asp Ile Thr Pro Glu Asn Phe Lys Cys Lys Asp Leu Arg Glu
                        340                 345                 350

Asn Tyr Cys Arg Asn Pro Asp Gly Ala Glu Ser Pro Trp Cys Phe Thr
                        355                 360                 365

Thr Asp Pro Asn Ile Arg Val Gly Tyr Cys Ser Gln Ile Pro Lys Cys
        370                 375                 380

Asp Val Ser Ser Gly Gln Asp Cys Tyr Arg Gly Asn Gly Lys Asn Tyr
        385                 390                 395                 400

Met Gly Asn Leu Ser Lys Thr Arg Ser Gly Leu Thr Cys Ser Met Trp
                        405                 410                 415

Asp Lys Asn Met Glu Asp Leu His Arg His Ile Phe Trp Glu Pro Asp
                        420                 425                 430

Ala Ser Lys Leu Asn Lys Asn Tyr Cys Arg Asn Pro Asp Asp Asp Ala
                        435                 440                 445

His Gly Pro Trp Cys Tyr Thr Gly Asn Pro Leu Ile Pro Trp Asp Tyr
                        450                 455                 460

Cys Pro Ile Ser Arg Cys Glu Gly Asp Thr Thr Pro Thr Ile Val Asn
        465                 470                 475                 480

Leu Asp His Pro Val Ile Ser Cys Ala Lys Thr Lys Gln Leu Arg Val
                        485                 490                 495

Val Asn Gly Ile Pro Thr Gln Thr Thr Val Gly Trp Met Val Ser Leu
                        500                 505                 510

Lys Tyr Arg Asn Lys His Ile Cys Gly Gly Ser Leu Ile Lys Glu Ser
                        515                 520                 525

Trp Val Leu Thr Ala Arg Gln Cys Phe Pro Ala Arg Asn Lys Asp Leu
                        530                 535                 540

Lys Asp Tyr Glu Ala Trp Leu Gly Ile His Asp Val His Glu Arg Gly
        545                 550                 555                 560

Glu Glu Lys Arg Lys Gln Ile Leu Asn Ile Ser Gln Leu Val Tyr Gly
                        565                 570                 575

Pro Glu Gly Ser Asp Leu Val Leu Leu Lys Leu Ala Arg Pro Ala Ile
                        580                 585                 590

Leu Asp Asn Phe Val Ser Thr Ile Asp Leu Pro Ser Tyr Gly Cys Thr
                        595                 600                 605

Ile Pro Glu Lys Thr Thr Cys Ser Ile Tyr Gly Trp Gly Tyr Thr Gly
                        610                 615                 620

Leu Ile Asn Ala Asp Gly Leu Leu Arg Val Ala His Leu Tyr Ile Met
        625                 630                 635                 640

Gly Asn Glu Lys Cys Ser Gln His His Gln Gly Lys Val Thr Leu Asn
                        645                 650                 655
```

-continued

```
Glu Ser Glu Leu Cys Ala Gly Ala Glu Lys Ile Gly Ser Gly Pro Cys
            660                 665                 670

Glu Gly Asp Tyr Gly Gly Pro Leu Ile Cys Glu Gln His Lys Met Arg
        675                 680                 685

Met Val Leu Gly Val Ile Val Pro Gly Arg Gly Cys Ala Ile Pro Asn
690                 695                 700

Arg Pro Gly Ile Phe Val Arg Val Ala Tyr Tyr Ala Lys Trp Ile His
705                 710                 715                 720

Lys Val Ile Leu Thr Tyr Lys Leu
                725

<210> SEQ ID NO 4
<211> LENGTH: 728
<212> TYPE: PRT
<213> ORGANISM: Rattus norvegicus

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly His
            20                  25                  30

Lys Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Asn Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Val Asn Asp Thr Asp Val Pro Met Glu Thr Thr Glu
```

```
              290                 295                 300
Cys Ile Gln Gly Gln Gly Glu Gly Tyr Arg Gly Thr Ala Asn Thr Ile
305                 310                 315                 320

Trp Asn Gly Ile Pro Cys Gln Arg Trp Asp Ser Gln Tyr Pro His Lys
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser Asn Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asn
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Val Gly Trp Met Ile Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Glu Glu Lys
545                 550                 555                 560

Arg Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Asn Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720
```

Leu Thr Tyr Lys Val Pro Glu Ser
                725

<210> SEQ ID NO 5
<211> LENGTH: 1390
<212> TYPE: PRT
<213> ORGANISM: Homo sapiens

<400> SEQUENCE: 5

Met Lys Ala Pro Ala Val Leu Ala Pro Gly Ile Leu Val Leu Leu Phe
 1               5                   10                  15

Thr Leu Val Gln Arg Ser Asn Gly Glu Cys Lys Glu Ala Leu Ala Lys
             20                  25                  30

Ser Glu Met Asn Val Asn Met Lys Tyr Gln Leu Pro Asn Phe Thr Ala
         35                  40                  45

Glu Thr Pro Ile Gln Asn Val Ile Leu His Glu His His Ile Phe Leu
     50                  55                  60

Gly Ala Thr Asn Tyr Ile Tyr Val Leu Asn Glu Glu Asp Leu Gln Lys
 65                  70                  75                  80

Val Ala Glu Tyr Lys Thr Gly Pro Val Leu Glu His Pro Asp Cys Phe
                 85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys

```
            355                 360                 365
Tyr Val Asn Asp Phe Phe Asn Lys Ile Val Asn Lys Asn Asn Val Arg
            370                 375                 380

Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
                405                 410                 415

Arg Thr Glu Phe Thr Thr Ala Leu Gln Arg Val Asp Leu Phe Met Gly
                420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Ile Thr Gly Lys Lys Ile Thr Lys
                500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
                580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
                660                 665                 670

Thr Leu Leu Thr Leu Thr Gly Asn Tyr Leu Asn Ser Gly Asn Ser Arg
                675                 680                 685

His Ile Ser Ile Gly Gly Lys Thr Cys Thr Leu Lys Ser Val Ser Asn
                690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
                740                 745                 750

Phe Ile Ser Gly Gly Ser Thr Ile Thr Gly Val Gly Lys Asn Leu Asn
                755                 760                 765

Ser Val Ser Val Pro Arg Met Val Ile Asn Val His Glu Ala Gly Arg
770                 775                 780
```

-continued

```
Asn Phe Thr Val Ala Cys Gln His Arg Ser Asn Ser Glu Ile Ile Cys
785                 790                 795                 800

Cys Thr Thr Pro Ser Leu Gln Gln Leu Asn Leu Gln Leu Pro Leu Lys
            805                 810                 815

Thr Lys Ala Phe Phe Met Leu Asp Gly Ile Leu Ser Lys Tyr Phe Asp
        820                 825                 830

Leu Ile Tyr Val His Asn Pro Val Phe Lys Pro Phe Glu Lys Pro Val
            835                 840                 845

Met Ile Ser Met Gly Asn Glu Asn Val Leu Glu Ile Lys Gly Asn Asp
        850                 855                 860

Ile Asp Pro Glu Ala Val Lys Gly Glu Val Leu Lys Val Gly Asn Lys
865                 870                 875                 880

Ser Cys Glu Asn Ile His Leu His Ser Glu Ala Val Leu Cys Thr Val
                885                 890                 895

Pro Asn Asp Leu Leu Lys Leu Asn Ser Glu Leu Asn Ile Glu Trp Lys
            900                 905                 910

Gln Ala Ile Ser Ser Thr Val Leu Gly Lys Val Ile Val Gln Pro Asp
        915                 920                 925

Gln Asn Phe Thr Gly Leu Ile Ala Gly Val Val Ser Ile Ser Thr Ala
    930                 935                 940

Leu Leu Leu Leu Leu Gly Phe Phe Leu Trp Leu Lys Lys Arg Lys Gln
945                 950                 955                 960

Ile Lys Asp Leu Gly Ser Glu Leu Val Arg Tyr Asp Ala Arg Val His
            965                 970                 975

Thr Pro His Leu Asp Arg Leu Val Ser Ala Arg Ser Val Ser Pro Thr
        980                 985                 990

Thr Glu Met Val Ser Asn Glu Ser Val Asp Tyr Arg Ala Thr Phe Pro
    995                 1000                1005

Glu Asp Gln Phe Pro Asn Ser Ser Gln Asn Gly Ser Cys Arg Gln Val
    1010                1015                1020

Gln Tyr Pro Leu Thr Asp Met Ser Pro Ile Leu Thr Ser Gly Asp Ser
1025                1030                1035                1040

Asp Ile Ser Ser Pro Leu Leu Gln Asn Thr Val His Ile Asp Leu Ser
            1045                1050                1055

Ala Leu Asn Pro Glu Leu Val Gln Ala Val Gln His Val Val Ile Gly
            1060                1065                1070

Pro Ser Ser Leu Ile Val His Phe Asn Glu Val Ile Gly Arg Gly His
            1075                1080                1085

Phe Gly Cys Val Tyr His Gly Thr Leu Leu Asp Asn Asp Gly Lys Lys
    1090                1095                1100

Ile His Cys Ala Val Lys Ser Leu Asn Arg Ile Thr Asp Ile Gly Glu
1105                1110                1115                1120

Val Ser Gln Phe Leu Thr Glu Gly Ile Ile Met Lys Asp Phe Ser His
            1125                1130                1135

Pro Asn Val Leu Ser Leu Leu Gly Ile Cys Leu Arg Ser Glu Gly Ser
            1140                1145                1150

Pro Leu Val Val Leu Pro Tyr Met Lys His Gly Asp Leu Arg Asn Phe
    1155                1160                1165

Ile Arg Asn Glu Thr His Asn Pro Thr Val Lys Asp Leu Ile Gly Phe
        1170                1175                1180

Gly Leu Gln Val Ala Lys Gly Met Lys Tyr Leu Ala Ser Lys Lys Phe
1185                1190                1195                1200
```

Val His Arg Asp Leu Ala Ala Arg Asn Cys Met Leu Asp Glu Lys Phe
                1205                1210                1215

Thr Val Lys Val Ala Asp Phe Gly Leu Ala Arg Asp Met Tyr Asp Lys
        1220                1225                1230

Glu Tyr Tyr Ser Val His Asn Lys Thr Gly Ala Lys Leu Pro Val Lys
            1235                1240                1245

Trp Met Ala Leu Glu Ser Leu Gln Thr Gln Lys Phe Thr Thr Lys Ser
        1250                1255                1260

Asp Val Trp Ser Phe Gly Val Leu Leu Trp Glu Leu Met Thr Arg Gly
1265                1270                1275                1280

Ala Pro Pro Tyr Pro Asp Val Asn Thr Phe Asp Ile Thr Val Tyr Leu
                1285                1290                1295

Leu Gln Gly Arg Arg Leu Leu Gln Pro Glu Tyr Cys Pro Asp Pro Leu
            1300                1305                1310

Tyr Glu Val Met Leu Lys Cys Trp His Pro Lys Ala Glu Met Arg Pro
        1315                1320                1325

Ser Phe Ser Glu Leu Val Ser Arg Ile Ser Ala Ile Phe Ser Thr Phe
    1330                1335                1340

Ile Gly Glu His Tyr Val His Val Asn Ala Thr Tyr Val Asn Val Lys
1345                1350                1355                1360

Cys Val Ala Pro Tyr Pro Ser Leu Leu Ser Ser Glu Asp Asn Ala Asp
                1365                1370                1375

Asp Glu Val Asp Thr Arg Pro Ala Ser Phe Trp Glu Thr Ser
            1380                1385                1390

<210> SEQ ID NO 6
<211> LENGTH: 1408
<212> TYPE: PRT
<213> ORGANISM: Pan troglodytes

<400> SEQUENCE: 6

Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

```
Ile Asn Phe Phe Val Gly Asn Thr Ile Asn Ser Ser Tyr Phe Pro Asp
            195                 200                 205

His Pro Leu His Ser Ile Ser Val Arg Arg Leu Lys Glu Thr Lys Asp
            210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
        290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
            355                 360                 365

Tyr Val Asn Asp Phe Phe Asn Lys Ile Val Asn Lys Asn Asn Val Arg
        370                 375                 380

Cys Leu Gln His Phe Tyr Gly Pro Asn His Glu His Cys Phe Asn Arg
385                 390                 395                 400

Thr Leu Leu Arg Asn Ser Ser Ser Cys Glu Ala Arg Arg Asp Glu Tyr
                405                 410                 415

Arg Thr Glu Phe Thr Thr Ala Leu Gln Arg Val Asp Leu Phe Met Gly
            420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
                485                 490                 495

Asn Gln Asn Gly Tyr Thr Leu Val Val Thr Gly Lys Lys Ile Thr Lys
            500                 505                 510

Ile Pro Leu Asn Gly Leu Gly Cys Arg His Phe Gln Ser Cys Ser Gln
        515                 520                 525

Cys Leu Ser Ala Pro Pro Phe Val Gln Cys Gly Trp Cys His Asp Lys
        530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
        595                 600                 605
```

-continued

```
Ser Cys Thr Leu Thr Leu Ser Glu Ser Thr Met Asn Thr Leu Lys Cys
610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
        675                 680                 685

His Ile Ser Ile Gly Gly Lys Thr Cys Thr Leu Lys Ser Val Ser Asn
690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
        755                 760                 765

Phe Cys Phe Ala Ser Gly Gly Ser Thr Ile Thr Gly Val Gly Lys Asn
770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
                805                 810                 815

Ile Cys Cys Thr Thr Pro Ser Leu Gln Gln Leu Asn Leu Gln Leu Pro
            820                 825                 830

Leu Lys Thr Lys Ala Phe Phe Met Leu Asp Gly Ile Leu Ser Lys Tyr
        835                 840                 845

Phe Asp Leu Ile Tyr Val His Asn Pro Val Phe Lys Pro Phe Glu Lys
850                 855                 860

Pro Val Met Ile Ser Met Gly Asn Glu Asn Val Leu Glu Ile Lys Gly
865                 870                 875                 880

Asn Asp Ile Asp Pro Glu Ala Val Lys Gly Glu Val Leu Lys Val Gly
                885                 890                 895

Asn Lys Ser Cys Glu Asn Ile His Leu His Ser Glu Ala Val Leu Cys
            900                 905                 910

Thr Val Pro Asn Asp Leu Leu Lys Leu Asn Ser Glu Leu Asn Ile Glu
        915                 920                 925

Trp Lys Gln Ala Ile Ser Ser Thr Val Leu Gly Lys Val Ile Val Gln
930                 935                 940

Pro Asp Gln Asn Phe Thr Gly Leu Ile Ala Gly Val Val Ser Ile Ser
945                 950                 955                 960

Ile Ala Leu Leu Leu Leu Leu Gly Phe Phe Leu Trp Leu Lys Lys Arg
                965                 970                 975

Lys Gln Ile Lys Asp Leu Gly Ser Glu Leu Val Arg Tyr Asp Ala Arg
            980                 985                 990

Val His Thr Pro His Leu Asp Arg Leu Val Ser Ala Arg Ser Val Ser
        995                 1000                1005

Pro Thr Thr Glu Met Val Ser Asn Glu Ser Val Asp Tyr Arg Ala Thr
        1010                1015                1020

Phe Pro Glu Asp Gln Phe Pro Asn Ser Ser Gln Asn Gly Ser Cys Arg
```

Gln Val Gln Tyr Pro Leu Thr Asp Met Ser Pro Ile Leu Thr Ser Gly
1025                1030                1035                1040

Asp Ser Asp Ile Ser Ser Pro Leu Leu Gln Asn Thr Val His Ile Asp
        1045                1050                1055

Leu Ser Ala Leu Asn Pro Glu Leu Val Gln Ala Val Gln His Val Val
    1060                1065                1070

Ile Gly Pro Ser Ser Leu Ile Val His Phe Asn Glu Val Ile Gly Arg
1075                1080                1085

Gly His Phe Gly Cys Val Tyr His Gly Thr Leu Leu Asp Asn Asp Gly
    1090                1095                1100

Lys Lys Ile His Cys Ala Val Lys Ser Leu Asn Arg Ile Thr Asp Ile
1105                1110                1115                1120

Gly Glu Val Ser Gln Phe Leu Thr Glu Gly Ile Ile Met Lys Asp Phe
        1125                1130                1135

Ser His Pro Asn Val Leu Ser Leu Leu Gly Ile Cys Leu Arg Ser Glu
    1140                1145                1150

Gly Ser Pro Leu Val Val Leu Pro Tyr Met Lys His Gly Asp Leu Arg
1155                1160                1165

Asn Phe Ile Arg Asn Glu Thr His Asn Pro Thr Val Lys Asp Leu Ile
1170                1175                1180

Gly Phe Gly Leu Gln Val Ala Lys Gly Met Lys Tyr Leu Ala Ser Lys
1185                1190                1195                1200

Lys Phe Val His Arg Asp Leu Ala Ala Arg Asn Cys Met Leu Asp Glu
        1205                1210                1215

Lys Phe Thr Val Lys Val Ala Asp Phe Gly Leu Ala Arg Asp Met Tyr
    1220                1225                1230

Asp Lys Glu Tyr Tyr Ser Val His Asn Lys Thr Gly Ala Lys Leu Pro
        1235                1240                1245

Val Lys Trp Met Ala Leu Glu Ser Leu Gln Thr Gln Lys Phe Thr Thr
1250                1255                1260

Lys Ser Asp Val Trp Ser Phe Gly Val Leu Leu Trp Glu Leu Met Thr
1265                1270                1275                1280

Arg Gly Ala Pro Pro Tyr Pro Asp Val Asn Thr Phe Asp Ile Thr Val
        1285                1290                1295

Tyr Leu Leu Gln Gly Arg Arg Leu Leu Gln Pro Glu Tyr Cys Pro Asp
    1300                1305                1310

Pro Leu Tyr Glu Val Met Leu Lys Cys Trp His Pro Lys Ala Glu Met
        1315                1320                1325

Arg Pro Ser Phe Ser Glu Leu Val Ser Arg Ile Ser Ala Ile Phe Ser
1330                1335                1340

Thr Phe Ile Gly Glu His Tyr Val His Val Asn Ala Thr Tyr Val Asn
1345                1350                1355                1360

Val Lys Cys Val Ala Pro Tyr Pro Ser Leu Leu Ser Ser Glu Asp Asn
        1365                1370                1375

Ala Asp Asp Glu Val Asp Thr Arg Pro Ala Ser Phe Trp Glu Thr Ser
    1380                1385                1390

1395                1400                1405

<210> SEQ ID NO 7
<211> LENGTH: 1379
<212> TYPE: PRT
<213> ORGANISM: Mus musculus

<400> SEQUENCE: 7

-continued

```
Met Lys Ala Pro Thr Val Leu Ala Pro Gly Ile Leu Val Leu Leu Leu
  1               5                  10                  15

Ser Leu Val Gln Arg Ser His Gly Glu Cys Lys Glu Ala Leu Val Lys
             20                  25                  30

Ser Glu Met Asn Val Asn Met Lys Tyr Gln Leu Pro Asn Phe Thr Ala
             35                  40                  45

Glu Thr Pro Ile Gln Asn Val Val Leu His Gly His His Ile Tyr Leu
 50                  55                  60

Gly Ala Thr Asn Tyr Ile Tyr Val Leu Asn Asp Lys Asp Leu Gln Lys
 65                  70                  75                  80

Val Ser Glu Phe Lys Thr Gly Pro Val Leu Glu His Pro Asp Cys Leu
             85                  90                  95

Pro Cys Arg Asp Cys Ser Ser Lys Ala Asn Ser Ser Gly Gly Val Trp
            100                 105                 110

Lys Asp Asn Ile Asn Met Ala Leu Leu Val Asp Thr Tyr Tyr Asp Asp
            115                 120                 125

Gln Leu Ile Ser Cys Gly Ser Val Asn Arg Gly Thr Cys Gln Arg His
        130                 135                 140

Val Leu Pro Pro Asp Asn Ser Ala Asp Ile Gln Ser Glu Val His Cys
145                 150                 155                 160

Met Phe Ser Pro Glu Glu Ser Gly Gln Cys Pro Asp Cys Val Val
                165                 170                 175

Ser Ala Leu Gly Ala Lys Val Leu Leu Ser Glu Lys Asp Arg Phe Ile
            180                 185                 190

Asn Phe Phe Val Gly Asn Thr Ile Asn Ser Ser Tyr Pro Pro Gly Tyr
        195                 200                 205

Ser Leu His Ser Ile Ser Val Arg Arg Leu Lys Glu Thr Gln Asp Gly
    210                 215                 220

Phe Lys Phe Leu Thr Asp Gln Ser Tyr Ile Asp Val Leu Pro Glu Phe
225                 230                 235                 240

Leu Asp Ser Tyr Pro Ile Lys Tyr Ile His Ala Phe Glu Ser Asn His
                245                 250                 255

Phe Ile Tyr Phe Leu Thr Val Gln Lys Glu Thr Leu Asp Ala Gln Thr
            260                 265                 270

Phe His Thr Arg Ile Ile Arg Phe Cys Ser Val Asp Ser Gly Leu His
    275                 280                 285

Ser Tyr Met Glu Met Pro Leu Glu Cys Ile Leu Thr Glu Lys Arg Arg
    290                 295                 300

Lys Arg Ser Thr Arg Glu Glu Val Phe Asn Ile Leu Gln Ala Ala Tyr
305                 310                 315                 320

Val Ser Lys Pro Gly Ala Asn Leu Ala Lys Gln Ile Gly Ala Ser Pro
            325                 330                 335

Ser Asp Asp Ile Leu Phe Gly Val Phe Ala Gln Ser Lys Pro Asp Ser
            340                 345                 350

Ala Glu Pro Val Asn Arg Ser Ala Val Cys Ala Phe Pro Ile Lys Tyr
            355                 360                 365

Val Asn Asp Phe Phe Asn Lys Ile Val Asn Lys Asn Asn Val Arg Cys
370                 375                 380

Leu Gln His Phe Tyr Gly Pro Asn His Glu His Cys Phe Asn Arg Thr
385                 390                 395                 400

Leu Leu Arg Asn Ser Ser Gly Cys Glu Ala Arg Ser Asp Glu Tyr Arg
            405                 410                 415

Thr Glu Phe Thr Thr Ala Leu Gln Arg Val Asp Leu Phe Met Gly Arg
```

```
                420             425             430
Leu Asn Gln Val Leu Leu Thr Ser Ile Ser Thr Phe Ile Lys Gly Asp
            435             440             445
Leu Thr Ile Ala Asn Leu Gly Thr Ser Glu Gly Arg Phe Met Gln Val
        450             455             460
Val Leu Ser Arg Thr Ala His Leu Thr Pro His Val Asn Phe Leu Leu
465             470             475             480
Asp Ser His Pro Val Ser Pro Glu Val Ile Val Glu His Pro Ser Asn
                485             490             495
Gln Asn Gly Tyr Thr Leu Val Val Thr Gly Lys Lys Ile Thr Lys Ile
            500             505             510
Pro Leu Asn Gly Leu Gly Cys Gly His Phe Gln Ser Cys Ser Gln Cys
        515             520             525
Leu Ser Ala Pro Tyr Phe Ile Gln Cys Gly Trp Cys His Asn Gln Cys
        530             535             540
Val Arg Phe Asp Glu Cys Pro Ser Gly Thr Trp Thr Gln Glu Ile Cys
545             550             555             560
Leu Pro Ala Val Tyr Lys Val Phe Pro Thr Ser Ala Pro Leu Glu Gly
                565             570             575
Gly Thr Val Leu Thr Ile Cys Gly Trp Asp Phe Gly Phe Arg Lys Asn
            580             585             590
Asn Lys Phe Asp Leu Arg Lys Thr Lys Val Leu Leu Gly Asn Glu Ser
        595             600             605
Cys Thr Leu Thr Leu Ser Glu Ser Thr Thr Asn Thr Leu Lys Cys Thr
        610             615             620
Val Gly Pro Ala Met Ser Glu His Phe Asn Val Ser Val Ile Ile Ser
625             630             635             640
Asn Ser Arg Glu Thr Thr Gln Tyr Ser Ala Phe Ser Tyr Val Asp Pro
                645             650             655
Val Ile Thr Ser Ile Ser Pro Arg Tyr Gly Pro Gln Ala Gly Gly Thr
            660             665             670
Leu Leu Thr Leu Thr Gly Lys Tyr Leu Asn Ser Gly Asn Ser Arg His
        675             680             685
Ile Ser Ile Gly Gly Lys Thr Cys Thr Leu Lys Ser Val Ser Asp Ser
        690             695             700
Ile Leu Glu Cys Tyr Thr Pro Ala Gln Thr Thr Ser Asp Glu Phe Pro
705             710             715             720
Val Lys Leu Lys Ile Asp Leu Ala Asn Arg Glu Thr Ser Ser Phe Ser
                725             730             735
Tyr Arg Glu Asp Pro Val Val Tyr Glu Ile His Pro Thr Lys Ser Phe
            740             745             750
Ile Ser Gly Gly Ser Thr Ile Thr Gly Ile Gly Lys Thr Leu Asn Ser
        755             760             765
Val Ser Leu Pro Lys Leu Val Ile Asp Val His Glu Val Gly Val Asn
        770             775             780
Tyr Thr Val Ala Cys Gln His Arg Ser Asn Ser Glu Ile Ile Cys Cys
785             790             795             800
Thr Thr Pro Ser Leu Lys Gln Leu Gly Leu Gln Leu Pro Leu Lys Thr
                805             810             815
Lys Ala Phe Phe Leu Leu Asp Gly Ile Leu Ser Lys His Phe Asp Leu
            820             825             830
Thr Tyr Val His Asn Pro Val Phe Glu Pro Phe Glu Lys Pro Val Met
        835             840             845
```

-continued

```
Ile Ser Met Gly Asn Glu Asn Val Glu Ile Lys Gly Asn Asn Ile
850                 855                 860

Asp Pro Glu Ala Val Lys Gly Glu Val Leu Lys Val Gly Asn Gln Ser
865                 870                 875                 880

Cys Glu Ser Leu His Trp His Ser Gly Ala Val Leu Cys Thr Val Pro
                885                 890                 895

Ser Asp Leu Leu Lys Leu Asn Ser Glu Leu Asn Ile Glu Trp Lys Gln
                900                 905                 910

Ala Val Ser Ser Thr Val Leu Gly Lys Val Ile Val Gln Pro Asp Gln
                915                 920                 925

Asn Phe Ala Gly Leu Ile Ile Gly Ala Val Ser Ile Ser Val Val Val
930                 935                 940

Leu Leu Leu Ser Gly Leu Phe Leu Trp Met Arg Lys Arg Lys His Lys
945                 950                 955                 960

Asp Leu Gly Ser Glu Leu Val Arg Tyr Asp Ala Arg Val His Thr Pro
                965                 970                 975

His Leu Asp Arg Leu Val Ser Ala Arg Ser Val Ser Pro Thr Thr Glu
                980                 985                 990

Met Val Ser Asn Glu Ser Val Asp Tyr Arg Ala Thr Phe Pro Glu Asp
                995                 1000                1005

Gln Phe Pro Asn Ser Ser Gln Asn Gly Ala Cys Arg Gln Val Gln Tyr
        1010                1015                1020

Pro Leu Thr Asp Leu Ser Pro Ile Leu Thr Ser Gly Asp Ser Asp Ile
1025                1030                1035                1040

Ser Ser Pro Leu Leu Gln Asn Thr Val His Ile Asp Leu Ser Ala Leu
        1045                1050                1055

Asn Pro Glu Leu Val Gln Ala Val Gln His Val Val Ile Gly Pro Ser
        1060                1065                1070

Ser Leu Ile Val His Phe Asn Glu Val Ile Gly Arg Gly His Phe Gly
        1075                1080                1085

Cys Val Tyr His Gly Thr Leu Leu Asp Asn Asp Gly Lys Lys Ile His
        1090                1095                1100

Cys Ala Val Lys Ser Leu Asn Arg Ile Thr Asp Ile Glu Glu Val Ser
1105                1110                1115                1120

Gln Phe Leu Thr Glu Gly Ile Ile Met Lys Asp Phe Ser His Pro Asn
        1125                1130                1135

Val Leu Ser Leu Leu Gly Ile Cys Leu Arg Ser Glu Gly Ser Pro Leu
        1140                1145                1150

Val Val Leu Pro Tyr Met Lys His Gly Asp Leu Arg Asn Phe Ile Arg
        1155                1160                1165

Asn Glu Thr His Asn Pro Thr Val Lys Asp Leu Ile Gly Phe Gly Leu
1170                1175                1180

Gln Val Ala Lys Gly Met Lys Tyr Leu Ala Ser Lys Lys Phe Val His
1185                1190                1195                1200

Arg Asp Leu Ala Ala Arg Asn Cys Met Leu Asp Glu Lys Phe Thr Val
        1205                1210                1215

Lys Val Ala Asp Phe Gly Leu Ala Arg Asp Met Tyr Asp Lys Glu Tyr
        1220                1225                1230

Tyr Ser Val His Asn Lys Thr Gly Ala Lys Leu Pro Val Lys Trp Met
        1235                1240                1245

Ala Leu Glu Ser Leu Gln Thr Gln Lys Phe Thr Thr Lys Ser Asp Val
        1250                1255                1260
```

```
Trp Ser Phe Gly Val Leu Leu Trp Glu Leu Met Thr Arg Gly Ala Pro
1265                1270                1275                1280

Pro Tyr Pro Asp Val Asn Thr Phe Asp Ile Thr Ile Tyr Leu Leu Gln
            1285                1290                1295

Gly Arg Arg Leu Leu Gln Pro Glu Tyr Cys Pro Asp Ala Leu Tyr Glu
        1300                1305                1310

Val Met Leu Lys Cys Trp His Pro Lys Ala Glu Met Arg Pro Ser Phe
    1315                1320                1325

Ser Glu Leu Val Ser Arg Ile Ser Ser Ile Phe Ser Thr Phe Ile Gly
    1330                1335                1340

Glu His Tyr Val His Val Asn Ala Thr Tyr Val Asn Val Lys Cys Val
1345                1350                1355                1360

Ala Pro Tyr Pro Ser Leu Leu Pro Ser Gln Asp Asn Ile Asp Gly Glu
            1365                1370                1375

Gly Asn Thr

<210> SEQ ID NO 8
<211> LENGTH: 1382
<212> TYPE: PRT
<213> ORGANISM: Rattus norvegicus

<400> SEQUENCE: 8

Met Lys Ala Pro Thr Ala Leu Ala Pro Gly Ile Leu Leu Leu Leu Leu
1               5                   10                  15

Thr Leu Ala Gln Arg Ser His Gly Glu Cys Lys Glu Ala Leu Val Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Val Leu His Gly His His Ile Tyr Leu
    50                  55                  60

Gly Ala Thr Asn Tyr Ile Tyr Val Leu Asn Asp Lys Asp Leu Gln Lys
65                  70                  75                  80

Val Ser Glu Phe Lys Thr Gly Pro Val Val Glu His Pro Asp Cys Phe
                85                  90                  95

Pro Cys Gln Asp Cys Ser Ser Lys Ala Asn Val Ser Gly Gly Val Trp
            100                 105                 110

Lys Asp Asn Val Asn Met Ala Leu Leu Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Leu Pro Pro Asp Asn Ala Ala Asp Ile Gln Ser Glu Val His Cys
145                 150                 155                 160

Met Phe Ser Pro Leu Ala Glu Glu Ser Gly Gln Cys Pro Asp Cys
                165                 170                 175

Val Val Ser Ala Leu Gly Ala Lys Val Leu Ser Glu Lys Asp Arg
            180                 185                 190

Phe Ile Asn Phe Phe Val Gly Asn Thr Ile Asn Ser Ser Tyr Pro Pro
        195                 200                 205

Asp Tyr Ser Leu His Ser Ile Ser Val Arg Arg Leu Lys Glu Thr Gln
    210                 215                 220

Asp Gly Phe Lys Phe Leu Thr Asp Gln Ser Tyr Ile Asp Val Leu Gly
225                 230                 235                 240

Glu Phe Arg Asp Ser Tyr Pro Ile Lys Tyr Ile His Ala Phe Glu Ser
                245                 250                 255
```

```
Asn His Phe Ile Tyr Phe Leu Thr Val Gln Lys Glu Thr Leu Asp Ala
            260                 265                 270

Gln Thr Phe His Thr Arg Ile Ile Arg Phe Cys Ser Val Asp Ser Gly
        275                 280                 285

Leu His Ser Tyr Met Glu Met Pro Leu Glu Cys Ile Leu Thr Glu Lys
        290                 295                 300

Arg Arg Lys Arg Ser Thr Arg Glu Glu Val Phe Asn Ile Leu Gln Ala
305                 310                 315                 320

Ala Tyr Val Ser Lys Pro Gly Ala Asn Leu Ala Lys Gln Ile Gly Ala
                325                 330                 335

Ser Pro Tyr Asp Asp Ile Leu Tyr Gly Val Phe Ala Gln Ser Lys Pro
            340                 345                 350

Asp Ser Ala Glu Pro Met Asn Arg Ser Ala Val Cys Ala Phe Pro Ile
        355                 360                 365

Lys Tyr Val Asn Asp Phe Phe Asn Lys Ile Val Asn Lys Asn Asn Val
        370                 375                 380

Arg Cys Leu Gln His Phe Tyr Gly Pro Asn His Glu His Cys Phe Asn
385                 390                 395                 400

Arg Thr Leu Leu Arg Asn Ser Ser Gly Cys Glu Val Arg Ser Asp Glu
                405                 410                 415

Tyr Arg Thr Glu Phe Thr Thr Ala Leu Gln Ala Val Asp Leu Phe Met
            420                 425                 430

Gly Arg Leu Asn His Val Leu Leu Thr Ser Ile Ser Thr Phe Ile Lys
        435                 440                 445

Gly Asp Leu Thr Ile Ala Asn Leu Gly Thr Ser Glu Gly Arg Phe Met
        450                 455                 460

Gln Val Val Leu Ser Arg Thr Ala His Phe Thr Pro His Val Asn Phe
465                 470                 475                 480

Leu Leu Asp Ser His Pro Val Ser Pro Glu Val Ile Val Glu His Pro
                485                 490                 495

Ser Asn Gln Asn Gly Tyr Thr Leu Val Val Thr Gly Lys Lys Ile Thr
            500                 505                 510

Lys Ile Pro Leu Asn Gly Leu Gly Cys Gly His Phe Gln Ser Cys Ser
        515                 520                 525

Gln Cys Leu Ser Ala Pro Tyr Phe Ile Gln Cys Gly Trp Cys His Asn
        530                 535                 540

Arg Cys Val His Ser Asn Glu Cys Pro Ser Gly Thr Trp Thr Gln Glu
545                 550                 555                 560

Ile Cys Leu Pro Ala Val Tyr Lys Val Phe Pro Thr Ser Ala Pro Leu
                565                 570                 575

Glu Gly Gly Thr Met Leu Thr Ile Cys Gly Trp Asp Phe Gly Phe Lys
            580                 585                 590

Lys Asn Asn Lys Phe Asp Leu Arg Lys Thr Lys Val Leu Leu Gly Asn
        595                 600                 605

Glu Ser Cys Thr Leu Thr Leu Ser Glu Ser Thr Thr Asn Thr Leu Lys
        610                 615                 620

Cys Thr Val Gly Pro Ala Met Ser Glu His Phe Asn Val Ser Val Ile
625                 630                 635                 640

Val Ser Asn Ser Arg Glu Thr Thr Gln Tyr Ser Ala Phe Ser Tyr Val
                645                 650                 655

Asp Pro Val Ile Thr Ser Ile Ser Pro Arg Tyr Gly Pro His Ala Gly
            660                 665                 670

Gly Thr Leu Leu Thr Leu Thr Gly Lys Tyr Leu Asn Ser Gly Asn Ser
```

-continued

```
            675                 680                 685
Arg His Ile Ser Ile Gly Gly Lys Thr Cys Thr Leu Lys Ser Val Ser
690                 695                 700

Asp Ser Ile Leu Glu Cys Tyr Thr Pro Gly His Thr Val Ser Ala Glu
705                 710                 715                 720

Phe Pro Val Lys Leu Lys Ile Asp Leu Ala Asp Arg Val Thr Ser Ser
                725                 730                 735

Phe Ser Tyr Gly Glu Asp Pro Phe Val Ser Glu Ile His Pro Thr Lys
                740                 745                 750

Ser Phe Ile Ser Gly Gly Ser Thr Ile Thr Gly Ile Gly Lys Asn Leu
                755                 760                 765

Asn Ser Val Ser Thr Pro Lys Leu Val Ile Glu Val His Asp Val Gly
770                 775                 780

Val Asn Tyr Thr Val Ala Cys Gln His Arg Ser Ser Glu Ile Ile
785                 790                 795                 800

Cys Cys Thr Thr Pro Ser Leu Gln Gln Leu Asp Leu Gln Leu Pro Leu
                805                 810                 815

Lys Thr Lys Ala Phe Phe Leu Leu Asp Gly Ile Leu Ser Lys His Phe
                820                 825                 830

Asp Leu Thr Tyr Val His Asp Pro Met Phe Lys Pro Phe Glu Lys Pro
                835                 840                 845

Val Met Ile Ser Met Gly Asn Glu Asn Val Val Glu Ile Lys Gly Asp
850                 855                 860

Asp Ile Asp Pro Glu Ala Val Lys Gly Glu Val Leu Lys Val Gly Asn
865                 870                 875                 880

Lys Ser Cys Glu Asn Leu His Trp His Ser Glu Ala Leu Leu Cys Thr
                885                 890                 895

Val Pro Ser Asp Leu Leu Lys Leu Asn Gly Gly Glu Leu Asn Ile Glu
                900                 905                 910

Trp Lys Gln Ala Val Ser Ser Thr Val Leu Gly Lys Val Ile Val Gln
                915                 920                 925

Pro Asp Gln Asn Phe Ala Gly Leu Ile Ile Gly Ala Val Ser Ile Ser
                930                 935                 940

Val Val Val Leu Leu Val Ser Gly Leu Phe Leu Trp Leu Arg Lys Arg
945                 950                 955                 960

Lys His Lys Asp Leu Gly Ser Glu Leu Val Arg Tyr Asp Ala Arg Val
                965                 970                 975

His Thr Pro His Leu Asp Arg Leu Val Ser Ala Arg Ser Val Ser Pro
                980                 985                 990

Thr Thr Glu Met Val Ser Asn Glu Ser Val Asp Tyr Arg Ala Thr Phe
            995                 1000                1005

Pro Glu Asp Gln Phe Pro Asn Ser Ser Gln Asn Gly Ala Cys Arg Gln
            1010                1015                1020

Val Gln Tyr Pro Leu Thr Asp Leu Ser Pro Ile Leu Thr Ser Gly Asp
1025                1030                1035                1040

Ser Asp Ile Ser Ser Pro Leu Leu Gln Asn Thr Val His Ile Asp Leu
                1045                1050                1055

Ser Ala Leu Asn Pro Glu Leu Val Gln Ala Val Gln His Val Val Ile
            1060                1065                1070

Gly Pro Ser Ser Leu Ile Val His Phe Asn Glu Val Ile Gly Arg Gly
            1075                1080                1085

His Phe Gly Cys Val Tyr His Gly Thr Leu Leu Asp Ser Asp Gly Lys
            1090                1095                1100
```

```
Lys Ile His Cys Ala Val Lys Ser Leu Asn Arg Ile Thr Asp Ile Glu
1105                1110                1115                1120

Glu Val Ser Gln Phe Leu Thr Glu Gly Ile Ile Met Lys Asp Phe Ser
            1125                1130                1135

His Pro Asn Val Leu Ser Leu Leu Gly Ile Cys Leu Arg Ser Glu Gly
        1140                1145                1150

Ser Pro Leu Val Val Leu Pro Tyr Met Lys His Gly Asp Leu Arg Asn
        1155                1160                1165

Phe Ile Arg Asn Glu Thr His Asn Pro Thr Val Lys Asp Leu Ile Gly
    1170                1175                1180

Phe Gly Leu Gln Val Ala Lys Gly Met Lys Tyr Leu Ala Ser Lys Lys
1185                1190                1195                1200

Phe Val His Arg Asp Leu Ala Ala Arg Asn Cys Met Leu Asp Glu Lys
                1205                1210                1215

Phe Thr Val Lys Val Ala Asp Phe Gly Leu Ala Arg Asp Met Tyr Asp
                1220                1225                1230

Lys Glu Tyr Tyr Ser Val His Asn Lys Thr Gly Ala Lys Leu Pro Val
            1235                1240                1245

Lys Trp Met Ala Leu Glu Ser Leu Gln Thr Gln Lys Phe Thr Thr Lys
        1250                1255                1260

Ser Asp Val Trp Ser Phe Gly Val Leu Leu Trp Glu Leu Met Thr Arg
1265                1270                1275                1280

Gly Ala Pro Pro Tyr Pro Asp Val Asn Thr Phe Asp Ile Thr Ile Tyr
                1285                1290                1295

Leu Leu Gln Gly Arg Arg Leu Leu Gln Pro Glu Tyr Cys Pro Asp Ala
            1300                1305                1310

Leu Tyr Glu Val Met Leu Lys Cys Trp His Pro Lys Ala Glu Met Arg
        1315                1320                1325

Pro Ser Phe Ser Glu Leu Val Ser Arg Ile Ser Ser Ile Phe Ser Thr
    1330                1335                1340

Phe Ile Gly Glu His Tyr Val His Val Asn Ala Thr Tyr Val Asn Val
1345                1350                1355                1360

Lys Cys Val Ala Pro Tyr Pro Ser Leu Leu Pro Ser Gln Asp Asn Ile
                1365                1370                1375

Asp Gly Glu Ala Asn Thr
            1380
```